US009045454B2

(12) United States Patent
Sui et al.

(10) Patent No.: US 9,045,454 B2
(45) Date of Patent: *Jun. 2, 2015

(54) BICYCLIC PYRROLE DERIVATIVES USEFUL AS AGONISTS OF GPR120

(71) Applicant: Janssen Pharmaceutica NV, Beerse (BE)

(72) Inventors: Zhihua Sui, Norristown, PA (US); Michael P. Winters, Morgantown, PA (US)

(73) Assignee: Jansen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/200,097

(22) Filed: Mar. 7, 2014

(65) Prior Publication Data

US 2014/0275182 A1   Sep. 18, 2014

Related U.S. Application Data

(60) Provisional application No. 61/783,158, filed on Mar. 14, 2013.

(51) Int. Cl.
*C07D 401/04* (2006.01)
*C07D 207/333* (2006.01)
*A61K 31/40* (2006.01)
*C07D 207/337* (2006.01)

(52) U.S. Cl.
CPC .......... *C07D 401/04* (2013.01); *C07D 207/333* (2013.01); *C07D 207/337* (2013.01); *A61K 31/40* (2013.01)

(58) Field of Classification Search
CPC .......................... C07D 207/333; A61K 31/40
USPC .......................................... 548/562; 514/427
See application file for complete search history.

(56) References Cited

U.S. PATENT DOCUMENTS

2011/0313003 A1   12/2011   Shi et al.

FOREIGN PATENT DOCUMENTS

| EP | 1559422 A1 | 8/2005 |
|---|---|---|
| EP | 1731505 A1 | 12/2006 |
| EP | 2151236 A1 | 2/2010 |
| WO | WO 2004/063155 A1 | 7/2004 |
| WO | WO 2005/063729 A1 | 7/2005 |
| WO | WO 2005/066136 A1 | 7/2005 |
| WO | WO 2008/030520 A1 | 3/2008 |
| WO | WO 2008/030618 A1 | 8/2008 |
| WO | WO 2008/103501 A1 | 8/2008 |
| WO | WO 2009/117421 A2 | 9/2009 |
| WO | WO 2010/048207 A2 | 4/2010 |
| WO | WO 2010/080537 A1 | 7/2010 |
| WO | WO 2010/104195 A1 | 9/2010 |
| WO | WO 2011/094890 A1 | 8/2011 |
| WO | WO 2011/159297 A1 | 12/2011 |

OTHER PUBLICATIONS

U.S. Appl. No. 14/200,108, filed Mar. 2014, Sui et al.*
Adachi et al., "Free fatty acids administered into the colon promote the secretion of glucagon-like peptide-1 and insulin.", Biochem. Biophys. Res. Commun., 2006, pp. 332-337, vol. 340.
American Diabetes Association, "Economic Costs of Diabetes in the U.S. in 2007", Diabetes Care, 2008 ,pp. 1-20, vol. 31.
American Diabetes Association. DiabetesPro: Health Professional Resources and Statistics. Fact Sheet. 2014.
Bell, G.I. and Polonsky, K.S., "Diabetes mellitus and genetically programmed defects in β cell function", Nature, Dec. 13, 2001, pp. 788-791, vol. 414.
Fukuda et al., "Directed Lithiation of N-Benzenesulfonyl-3-bromopyrrole. Electrophile-Controlled Regioselective Functionalization via Dynamic Equilibrium between C-2 and C-5 Lithio Species.", Organic Letters, 2010, pp. 2734-2737, vol. 12(12).
Gotoh et al., "The regulation of adipogenesis through GPR120.", Biochem. Biophys. Res. Commun., 2007, pp. 591-597, vol. 354.
Hara et al., "Novel selective ligands for free fatty acid receptors GPR120 and GPR40.", Naunyn-Schmied Arc. Pharmacol., 2009, pp. 247-255, vol. 380.
Hirasawa et al., "Free fatty acids regulate gut incretin glucagon-like peptide-1 secretion through GPR120", Nature Med, 2005, pp. 90-94, vol. 11(1).
Ishikawa et al., "Cesium Fluroide-Mediated Claisen Rearrangements of Phenyl Propargyl Esters: Effect of a Substituent on the Phenyl Ring on the Rearrangement[1].", Heterocycles, 1994, pp. 371-380, vol. 39(1).
Itoh et al., "Free fatty acids regulate insulin secretion from pancreatic β cells through GPR40", Nature, Mar. 13, 2003, pp. 173-176, vol. 422.
Knop et al., "Incretin-Based Therapy of Type 2 Diabetes Mellitus.", Curr.Protein Pept. Sci., 2009, pp. 46-55, vol. 10.
Moller, D.E., "New Drug Targets for type 2 diabetes and the metabolic syndrome.", Nature, Dec. 13, 2001, pp. 821-827, vol. 414.
Nathan, D.M., "Initial Management of Glycemia in Type 2 Diabetes Mellitus", N. Engl. J. Med., Oct. 24, 2002, pp. 1342-1349, vol. 347(17).
Steneberg et al., "The FFA receptor GPR40 links hyperinsulinemia, hepatic steatosis and impaired glucose homeostasis in mouse"., Cell Metab, Apr. 2005, pp. 245-258, vol. 1.
Turner et al., "Glycemic Control With Diet, Sulfonylurea, Metformin or Insulin in Patients With Type 2 Diabetes Mellitus.", JAMA, Jun. 2, 1999, pp. 2005-2012, vol. 281(21).
Wild et al., "Global Prevalence of Diabetes", Diabetes Care, May 2004, pp. 1047-1053, vol. 27(5).
Sun et al., "Structure-Activity Relationships of GPR120 Agonists Based on a Docking Simulation.", *Molecular Pharmaceology*, Nov. 1, 2010, pp. 804-810, vol. 78(5), XP0055122562.
International Search Report and Written Opinion of the International Searching Authority relating to International Patent Application No. PCT/US2014/021762, which corresponds to U.S. Appl. No. 14/200,114. Date of Mailing: May 21, 2014.

(Continued)

Primary Examiner — Michael Barker
(74) Attorney, Agent, or Firm — Jeremy K. McKown

(57) ABSTRACT

The present invention is directed to bicyclic pyrrole derivatives, pharmaceutical compositions containing them and their use in the treatment of disorders and conditions modulated by GPR120. More particularly, the compounds of the present invention are agonists of GPR120, useful in the treatment of, such as for example, Type II diabetes mellitus.

22 Claims, No Drawings

(56) References Cited

OTHER PUBLICATIONS

International Search Report and Written Opinion of the International Searching Authority relating to International Patent Application No. PCT/US2014/021775, which corresponds to U.S. Appl. No. 14/200,127. Date of Mailing: May 15, 2014.
International Search Report and Written Opinion of the International Searching Authority relating to International Patent Application No. PCT/US2014/021740, which corresponds to U.S. Appl. No. 14/200,097. Date of Mailing: May 23, 2014.
International Search Report and Written Opinion of the International Searching Authority relating to International Patent Application No. PCT/US2014/021732, which corresponds to U.S. Appl. No. 14/200,108. Date of Mailing: May 20, 2014.
Partial International Search Report relating to International Patent Application No. PCT/2014/021790. Date of Mailing: Jun. 24, 2014.

* cited by examiner

BICYCLIC PYRROLE DERIVATIVES USEFUL AS AGONISTS OF GPR120

CROSS REFERENCE TO RELATED APPLICATIONS

This application claims the benefit of U.S. Provisional Application 61/783,158, filed on Mar. 14, 2013, which is incorporated by reference herein in its entirety.

FIELD OF THE INVENTION

The present invention is directed to bicyclic pyrrole derivatives, pharmaceutical compositions containing them and their use in the treatment of disorders and conditions modulated by GPR120. More particularly, the compounds of the present invention are agonists of GPR120, useful in the treatment of related diseases and disorders, such as for example, Type II diabetes mellitus.

BACKGROUND OF THE INVENTION

A diabetes mellitus epidemic is unfolding across the globe with the World Health Organization (WHO) reporting a worldwide prevalence of 177 million patients with diabetes. It is estimated that the incidence of all forms of diabetes totals approximately 2.8% of the world population. The number of newly diagnosed diabetic patients is increasing by 4-5% per year. The total number of people with diabetes worldwide is projected to rise to 366 million (4.4% prevalence) in 2030. Type 2 diabetes accounts for approximately 95% of all diabetes cases. Long-term complications of type 2 diabetes include atherosclerosis, heart disease, stroke, end-stage renal disease, retinopathy leading to blindness, nerve damage, sexual dysfunction, frequent infections, and difficult-to-treat foot ulcers, sometimes resulting in lower limb amputation. Diabetics are twice as likely to develop cardiovascular disease or have a stroke, 2 to 6 times more likely to have transient ischemic attacks, and 15 to 40 times more likely to require lower-limb amputation compared with the general population. The total estimated cost of diabetes in 2007 in the US was $174 billion, including $116 billion in medical expenditures. The largest components of medical expenditures attributed to diabetes are hospital inpatient care (50% of total cost), diabetes medication and supplies (12%), retail prescriptions to treat complications of diabetes (11%), and physician office visits (9%). This may be related to the lack of durable efficacy of current drug therapies for Type 2 diabetes (>50% Type 2 patients are not reaching the targeted blood glucose control with current oral medications after 5 years of treatment). There is a general consensus that a considerable need exists for improved awareness, diagnosis and new, more effective, drug therapies for diabetes.

GLP-1 is secreted from specific cells in the colon according to a meal and is a key regulator of glucose homeostasis, linking the gut, brain and pancreas. GLP-1 potentiates insulin secretion, reduces glucagon secretion and preserves β-cell function whilst also improving satiety. Levels of post-prandial GLP-1 are reduced in type 2 diabetics and dramatically elevated according to gastric by-pass surgery, contributing to the amelioration of type 2 diabetes in these patients. Approaches that prolong the half-life of GLP-1 (JANUVIA (Merck), GALVUS (Novartis)) or activate the GLP-1 receptor (BYETTA (Amylin)) have been recently approved for use in type 2 diabetes.

Hyperinsulinemia in patients with type 2 diabetes mellitus results from peripheral insulin resistance, coupled with inadequate pancreatic insulin secretion and elevated glucagon levels. There is a strong correlation between obesity and peripheral insulin resistance and hyperinsulinemia. Accumulation of free fatty acids in insulin responsive tissues other than fat (i.e. muscle and liver) results in tissue insulin resistance. Additionally, free fatty acids have a direct effect on the pancreas and in the colon and further stimulate glucose-dependent insulin secretion and GLP-1 release with acute exposure whereas chronic exposure of free fatty acids impairs insulin secretion and becomes toxic to the β-cell. In the liver, hyperinsulinemia per se has been linked to exacerbating insulin resistance by increasing liver fatty acid accumulation and hepatic glucose output creating a vicious cycle of disease progression. Current therapeutic strategies only partially address the complex pathology of free fatty acids in the exacerbation of diabetes. Agents that target both liver and pancreas function, directly or indirectly via GLP-1 release, either individually or in combination with current treatment, could significantly improve blood glucose control while maintaining β-cell function. Agents that potentiate GLP-1 release also have the ability to reduce weight, providing additional benefits.

GPR120 is a seven transmembrane g-protein coupled receptor (GPCR) that is predominantly expressed in the intestine and adipose. GPR120 functions as a receptor for long chain free fatty acids (FFAs). Acute FFA stimulation of GPR120 in GLP-1 expressing cell-lines amplifies GLP-1 release. Administration of α-linolenic acid into the colon of mice increases GLP-1 and potentiates insulin release according to a glucose challenge. In contrast to agonists of GPR40, the existing literature suggests that a GPR120 agonist would potentiate insulin secretion and reduce glucagon indirectly via GLP-1 release. GPR120 is also expressed in adipose, with expression induced during differentiation. Inhibition of GPR120 expression in 3T3-L1 adipocytes has been shown to reduce adipocyte differentiation. The role of the receptor in the adipose or in the taste cells of the tongue where it has also been found remains unclear.

GPR120 is a Gq coupled GPCR that acts a receptor for long chain fatty acids. It belongs to a family of lipid binding GPCRs that include GPR 40, 41, 43. Functionally, GPR120s closest homolog is GPR40. The cloned rat and mouse GPR120 receptors have been cloned and have >85% homology with the human receptor. GPR120 signals through Gq to elevate intracellular Ca+2 levels as well as activate MAP kinase signal transduction cascades. GPR120's activation of calcium flux and PKC activation is most likely how FFAs contribute to the release GLP-1 in the L-cell.

Although relatively little is known about GPR120 due to lack of potent, selective pharmacological tools or a documented metabolic phenotype of GPR120 knockout mice, the potential to elevate GLP-1 from a small-molecule perspective is attractive as a novel approach to unmet medical need in the treatment of type 2 diabetes mellitus and related disorders. The beneficial effects of elevating GLP-1 are already well validated in the clinic and in addition to improved glucose homeostasis, offer the potential of weight loss. Thus it is theorized that GPR120 agonists may be complementary to existing diabetes therapies that affect liver insulin sensitivity and those that preserve β-cell function.

There remains a need for GPR120 agonists for the treatment of disorders including, but not limited to obesity, Type II diabetes mellitus, dyslipidemia, and the like.

SUMMARY OF THE INVENTION

The present invention is directed to compounds of formula (I)

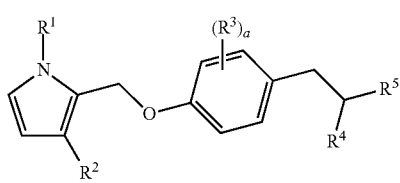

wherein $R^1$ is selected from the group consisting of phenyl and pyridinyl; wherein the phenyl or pyridinyl is optionally substituted with one to three substituents independently selected from the group consisting of halogen, cyano, carboxy, —C(O)O—($C_{1-4}$alkyl), —C(O)—($C_{1-4}$alkyl), $C_{1-4}$alkyl, fluoro substituted $C_{1-4}$alkyl, $C_{1-4}$alkoxy and fluoro substituted $C_{1-4}$alkoxy;

$R^2$ is selected from the group consisting of hydrogen, halogen, cyano, $C_{1-4}$alkyl and fluoro substituted $C_{1-4}$alkyl;

a is in integer from 0 to 3;

each $R^3$ is independently selected from the group consisting of halogen, $C_{1-4}$alkyl, fluoro substituted $C_{1-4}$alkyl, and cyano;

provided that when a is 2 or 3, then only one $R^3$ can be cyano;

$R^4$ is selected from the group consisting of hydrogen and methyl;

$R^5$ is selected from the group consisting of $CH_2OH$ and $C(O)OH$;

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder modulated by GPR120 (selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders) comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder modulated by GPR120 (selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders). In another embodiment, the present invention is directed to a composition comprising a compound of formula (I) for the treatment of a disorder modulated by GPR120 (selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders).

Another example of the invention is the use of any of the compounds described herein in the preparation of a medicament for treating: (a) obesity, (b) obesity related disorders, (c) impaired oral glucose tolerance, (d) insulin resistance, (e) Type II diabetes mellitus, (f) metabolic syndrome, (g) metabolic syndrome X, (h) dyslipidemia, (i) elevated LDL, (j) elevated triglycerides, (k) obesity induced inflammation, (l) osteoporosis and (m) obesity related cardiovascular disorders, in a subject in need thereof. In another example, the present invention is directed to a compound as described herein for use in a methods for treating a disorder selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders, in a subject in need thereof.

DETAILED DESCRIPTION OF THE INVENTION

The present invention is directed to compounds of formula (I)

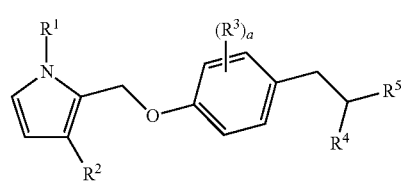

wherein $R^1$, $R^2$, a, $R^3$, $R^4$ and $R^5$ are as herein defined. The compounds of the present invention are GPR120 agonists useful in the treatment of related disorders and diseases, including, obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus or dyslipidemia.

In an embodiment, the present invention is directed to compounds of formula (I) wherein $R^1$ is selected from the group consisting of phenyl and pyridinyl; wherein the phenyl or pyridinyl is optionally substituted with one to two substituents independently selected from the group consisting of halogen, $C_{1-4}$alkyl, fluoro substituted $C_{1-4}$alkyl, $C_{1-4}$alkoxy and fluoro substituted $C_{1-4}$alkoxy. In another embodiment, the present invention is directed to compounds of formula (I) wherein $R^1$ is selected from the group consisting of phenyl and pyridinyl; wherein the phenyl is optionally substituted with one to two substituents independently selected from the group consisting of halogen, $C_{1-4}$alkyl, fluoro substituted $C_{1-4}$alkyl, $C_{1-4}$alkoxy and fluoro substituted $C_{1-4}$ alkoxy; and wherein the pyridinyl is optionally substituted with one substituent selected from the group consisting of $C_{1-4}$alkyl and $C_{1-4}$alkoxy. In another embodiment, the present invention is directed to compounds of formula (I) wherein $R^1$ is selected from the group consisting of phenyl and pyridin-3-yl; wherein the phenyl is optionally substituted with one to two substituents independently selected from the group consisting of halogen, $C_{1-2}$alkyl, fluoro substituted $C_{1-2}$alkyl, $C_{1-2}$alkoxy and fluoro substituted $C_{1-2}$alkoxy.

In another embodiment, the present invention is directed to compounds of formula (I) wherein $R^1$ is selected from the group consisting of phenyl, 4-chlorophenyl, 4-fluorophenyl, 4-bromophenyl, 4-methylphenyl, 4-ethylphenyl, 4-methoxyphenyl, 3-fluoro-4-chloro-phenyl, 3-fluoro-4-methyl-phenyl, 6-methyl-pyridin-3-yl, 6-ethyl-pyridin-3-yl and 6-methoxy-pyridin-3-yl.

In another embodiment, the present invention is directed to compounds of formula (I) wherein $R^1$ is selected from the group consisting of phenyl, 4-chlorophenyl, 4-bromophenyl, 4-methylphenyl, 4-ethylphenyl, 4-methoxyphenyl, 3-fluoro-4-chloro-phenyl, 3-fluoro-4-methyl-phenyl, 6-methyl-pyridin-3-yl, 6-ethyl-pyridin-3-yl and 6-methoxy-pyridin-3-yl. In another embodiment, the present invention is directed to compounds of formula (I) wherein $R^1$ is selected from the group consisting of phenyl, 4-chlorophenyl, 4-bromophenyl, 4-methylphenyl, 4-ethylphenyl, 4-methoxyphenyl, 6-methyl-pyridin-3-yl, 6-ethyl-pyridin-3-yl and 6-methoxy-pyridin-3-yl. In another embodiment, the present invention is directed to compounds of formula (I) wherein $R^1$ is selected from the group consisting of phenyl, 4-chlorophenyl, 4-methylphenyl, 4-ethylphenyl, 4-methoxyphenyl, 6-methyl-pyridin-3-yl, 6-ethyl-pyridin-3-yl and 6-methoxy-pyridin-3-yl. In another embodiment, the present invention is directed to compounds of formula (I) wherein $R^1$ is selected from the group consisting of 4-chlorophenyl, 4-methylphenyl, 4-ethylphenyl, 6-methyl-pyridin-3-yl and 6-ethyl-pyridin-3-yl.

In an embodiment, the present invention is directed to compounds of formula (I) wherein $R^2$ is selected from the group consisting of hydrogen, halogen, cyano, $C_{1-4}$alkyl and fluoro substituted $C_{1-4}$alkyl. In another embodiment, the present invention is directed to compounds of formula (I) wherein $R^2$ is selected from the group consisting of hydrogen, halogen, cyano, $C_{1-2}$alkyl and fluoro substituted $C_{1-2}$alkyl.

In another embodiment, the present invention is directed to compounds of formula (I) wherein $R^2$ is selected from the group consisting of hydrogen, chloro, bromo, cyano, trifluoromethyl and pentafluoroethyl. In another embodiment, the present invention is directed to compounds of formula (I) wherein $R^2$ is selected from the group consisting of hydrogen, chloro, bromo and trifluoromethyl. In another embodiment, the present invention is directed to compounds of formula (I) wherein $R^2$ is trifluoromethyl.

In an embodiment, the present invention is directed to compounds of formula (I) wherein $R^2$ is selected from the group consisting of halogen, $C_{1-4}$ alkyl and fluoro substituted $C_{1-4}$alkyl. In another embodiment, the present invention is directed to compounds of formula (I) wherein $R^2$ is selected from the group consisting of halogen, $C_{1-2}$alkyl and fluoro substituted $C_{1-2}$alkyl.

In another embodiment, the present invention is directed to compounds of formula (I) wherein $R^2$ is selected from the group consisting of chloro, bromo, cyano, trifluoromethyl and pentafluoroethyl. In another embodiment, the present invention is directed to compounds of formula (I) wherein $R^2$ is selected from the group consisting of chloro, bromo and trifluoromethyl.

In another embodiment, the present invention is directed to compounds of formula (I) wherein a is an integer from 0 to 2.

In another embodiment, the present invention is directed to compounds of formula (I) wherein a is an integer from 1 to 2. In another embodiment, the present invention is directed to compounds of formula (I) wherein a is 2.

In another embodiment, the present invention is directed to compounds of formula (I) wherein a is 2; and wherein the $R^3$ groups are bound at the 2- and 3- or at the 3- and 5-positions of the phenyl ring.

In an embodiment, the present invention is directed to compounds of formula (I) wherein each $R^3$ is independently selected from the group consisting of halogen and $C_{1-4}$alkyl. In another embodiment, the present invention is directed to compounds of formula (I) wherein each $R^3$ is independently selected from the group consisting of halogen and $C_{1-2}$alkyl.

In another embodiment, the present invention is directed to compounds of formula (I) wherein a is 2 and $R^3$ is selected from the group consisting of 2,3-difluoro, 2,3-dimethyl and 3,5-difluoro.

In another embodiment, the present invention is directed to compounds of formula (I) wherein a is 2 and $R^3$ is selected from the group consisting of 2,3-difluoro, 2,3-dimethyl and 3,5-difluoro. In another embodiment, the present invention is directed to compounds of formula (I) wherein a is 2 and $R^3$ is selected from the group consisting of 2,3-difluoro and 3,5-difluoro.

In another embodiment, the present invention is directed to compounds of formula (I) wherein $R^4$ is selected from the group consisting of hydrogen and methyl. In another embodiment, the present invention is directed to compounds of formula (I) wherein $R^4$ is hydrogen.

In another embodiment, the present invention is directed to compounds of formula (I) wherein $R^5$ is selected from the group consisting of —$CH_2OH$ and —$C(O)OH$. In another embodiment, the present invention is directed to compounds of formula (I) wherein $R^5$ is —$CH_2OH$. In another embodiment, the present invention is directed to compounds of formula (I) wherein $R^5$ is —$C(O)OH$.

Additional embodiments of the present invention, include those wherein the substituents selected for one or more of the variables defined herein (i.e. a, $R^1$, $R^2$, $R^3$, $R^4$, $R^5$, etc.) are independently selected to be any individual substituent or any subset of substituents selected from the complete list as defined herein.

In another embodiment of the present invention is any single compound or subset of compounds selected from the representative compounds listed in Tables 1 below. Representative compounds of the present invention are as listed in Table 1 below. Unless otherwise noted, wherein a stereogenic center is present in the listed compound, the compound was prepared as a mixture of stereo-isomers.

TABLE 1

Representative Compounds of Formula (I)

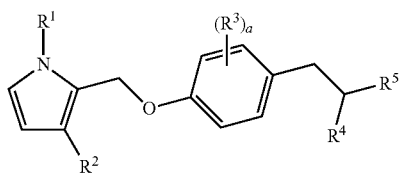

| ID No. | $R^1$ | $R^2$ | $(R^3)_a$ | $R^4$ | $R^5$ |
|---|---|---|---|---|---|
| 1 | 4-chlorophenyl | H | 2,3-dimethyl | H | C(O)OH |
| 2 | 4-ethylphenyl | H | 2,3-dimethyl | H | C(O)OH |
| 3 | 4-bromophenyl | H | 2,3-dimethyl | H | C(O)OH |

TABLE 1-continued

Representative Compounds of Formula (I)

| ID No. | $R^1$ | $R^2$ | $(R^3)_a$ | $R^4$ | $R^5$ |
|---|---|---|---|---|---|
| 4 | 4-chlorophenyl | H | 2,3-difluoro | H | C(O)OH |
| 5 | 4-chlorophenyl | bromo | 2,3-difluoro | H | CH$_2$OH |
| 6 | 4-chlorophenyl | bromo | 2,3-difluoro | H | C(O)OH |
| 7 | 4-chlorophenyl | chloro | 2,3-dimethyl | H | CH$_2$OH |
| 8 | 4-chlorophenyl | chloro | 2,3-dimethyl | H | C(O)OH |
| 9 | 4-chlorophenyl | cyano | 2,3-difluoro | H | C(O)OH |
| 10 | 4-chlorophenyl | chloro | 2,3-difluoro | H | CH$_2$OH |
| 11 | 4-chlorophenyl | chloro | 2,3-difluoro | H | C(O)OH |
| 12 | 4-chlorophenyl | cyano | 2,3-dimethyl | H | C(O)OH |
| 13 | 4-chlorophenyl | bromo | 2,3-dimethyl | H | CH$_2$OH |
| 14 | 4-chlorophenyl | bromo | 2,3-dimethyl | H | C(O)OH |
| 15 | 4-chlorophenyl | trifluoromethyl | 2,3-dimethyl | H | C(O)OH |
| 16 | 4-chlorophenyl | trifluoromethyl | 2,3-difluoro | H | C(O)OH |
| 17 | 4-chlorophenyl | trifluoromethyl | 2,3-dimethyl | H | CH$_2$OH |
| 18 | 4-bromophenyl | trifluoromethyl | 2,3-dimethyl | H | CH$_2$OH |
| 19 | phenyl | trifluoromethyl | 2,3-dimethyl | H | CH$_2$OH |
| 20 | 4-bromophenyl | trifluoromethyl | 2,3-difluoro | H | C(O)OH |
| 21 | 4-bromophenyl | trifluoromethyl | 2,3-difluoro | H | CH$_2$OH |
| 22 | 4-bromophenyl | trifluoromethyl | 3,5-difluoro | H | C(O)OH |
| 23 | 4-bromophenyl | trifluoromethyl | 2,3-dimethyl | H | C(O)OH |
| 24 | 4-methoxyphenyl | trifluoromethyl | 2,3-dimethyl | H | C(O)OH |
| 25 | 4-methoxyphenyl | trifluoromethyl | 2,3-dimethyl | H | CH$_2$OH |
| 26 | 4-methoxyphenyl | trifluoromethyl | 2,3-difluoro | H | C(O)OH |
| 27 | 4-methoxyphenyl | trifluoromethyl | 2,3-difluoro | H | CH$_2$OH |
| 28 | 4-methoxyphenyl | trifluoromethyl | 3,5-difluoro | H | C(O)OH |
| 29 | 4-chlorophenyl | trifluoromethyl | 2,3-difluoro | H | CH$_2$OH |
| 30 | 4-bromophenyl | trifluoromethyl | 3,5-difluoro | H | CH$_2$OH |
| 31 | 4-methoxyphenyl | trifluoromethyl | 3,5-difluoro | H | CH$_2$OH |
| 32 | 4-ethylphenyl | trifluoromethyl | 3,5-difluoro | H | C(O)OH |
| 33 | 4-ethylphenyl | trifluoromethyl | 3,5-difluoro | H | CH$_2$OH |
| 34 | 4-ethylphenyl | trifluoromethyl | 2,3-difluoro | H | C(O)OH |
| 35 | phenyl | trifluoromethyl | 3,5-difluoro | H | CH$_2$OH |
| 36 | 4-ethylphenyl | trifluoromethyl | 2,3-dimethyl | H | C(O)OH |
| 37 | 4-methylphenyl | trifluoromethyl | 3,5-difluoro | H | CH$_2$OH |
| 38 | phenyl | trifluoromethyl | 3,5-difluoro | H | C(O)OH |
| 39 | 4-methylphenyl | trifluoromethyl | 3,5-difluoro | H | C(O)OH |
| 40 | 4-ethylphenyl | trifluoromethyl | 2,3-dimethyl | H | CH$_2$OH |
| 41 | 4-ethylphenyl | trifluoromethyl | 2,3-difluoro | H | CH$_2$OH |
| 42 | 4-methylphenyl | trifluoromethyl | 2,3-difluoro | H | C(O)OH |
| 43 | 4-methylphenyl | trifluoromethyl | 2,3-dimethyl | H | C(O)OH |
| 44 | 4-methylphenyl | trifluoromethyl | 2,3-difluoro | H | CH$_2$OH |
| 45 | 4-methylphenyl | trifluoromethyl | 2,3-dimethyl | H | CH$_2$OH |
| 46 | 4-chlorophenyl | trifluoromethyl | 3,5-difluoro | H | CH$_2$OH |
| 47 | 6-methylpyridin-3-yl | trifluoromethyl | 2,3-difluoro | H | CH$_2$OH |
| 48 | 6-methylpyridin-3-yl | trifluoromethyl | 3,5-difluoro | H | CH$_2$OH |
| 49 | 6-methylpyridin-3-yl | trifluoromethyl | 3,5-difluoro | H | C(O)OH |
| 50 | 6-methoxypyridin-3-yl | trifluoromethyl | 2,3-difluoro | H | CH$_2$OH |
| 51 | 6-methoxypyridin-3-yl | trifluoromethyl | 3,5-difluoro | H | C(O)OH |
| 52 | 6-methoxypyridin-3-yl | trifluoromethyl | 3,5-difluoro | H | CH$_2$OH |
| 53 | 6-methylpyridin-3-yl | trifluoromethyl | 2,3-difluoro | H | C(O)OH |
| 54 | 6-ethylpyridin-3-yl | trifluoromethyl | 2,3-difluoro | H | CH$_2$OH |
| 55 | 6-ethylpyridin-3-yl | trifluoromethyl | 3,5-difluoro | H | CH$_2$OH |
| 56 | 6-ethylpyridin-3-yl | trifluoromethyl | 3,5-difluoro | H | C(O)OH |
| 57 | 6-methoxypyridin-3-yl | trifluoromethyl | 2,3-difluoro | H | C(O)OH |
| 58 | 6-ethylpyridin-3-yl | trifluoromethyl | 2,3-difluoro | H | C(O)OH |
| 59 | 4-chlorophenyl | trifluoromethyl | 3,5-difluoro | CH$_3$ | C(O)OH |
| 60 | 4-methylphenyl | trifluoromethyl | 3,5-difluoro | CH$_3$ | C(O)OH |
| 61 | 4-ethylphenyl | trifluoromethyl | 3,5-difluoro | CH$_3$ | C(O)OH |
| 62 | 3-fluoro-4-methylphenyl | trifluoromethyl | 3,5-difluoro | H | C(O)OH |
| 63 | 4-chlorophenyl | pentafluoroethyl | 3,5-difluoro | H | C(O)OH |
| 64 | 3-fluoro-4-methylphenyl | trifluoromethyl | 3,5-difluoro | CH$_3$ | C(O)OH |
| 65 | 4-fluorophenyl | trifluoromethyl | 3,5-difluoro | CH$_3$ | C(O)OH |
| 66 | 3-fluoro-4-methylphenyl | trifluoromethyl | 2,3-dimethyl | H | C(O)OH |
| 67 | 3-fluoro-4-chlorophenyl | trifluoromethyl | 3,5-difluoro | H | C(O)OH |

TABLE 1-continued

Representative Compounds of Formula (I)

| ID No. | R$^1$ | R$^2$ | (R$^3$)$_a$ | R$^4$ | R$^5$ |
|---|---|---|---|---|---|
| 68 | 3-fluoro-4-chlorophenyl | trifluoromethyl | 2,3-dimethyl | H | C(O)OH |
| 69 | 3-fluoro-4-chlorophenyl | trifluoromethyl | 3,5-difluoro | CH$_3$ | C(O)OH |
| 70 | 4-chlorophenyl | trifluoromethyl | 3,5-difluoro | H | C(O)OH |

In an embodiment, the present invention is directed to any single compound or subset of compounds selected from the group as listed in Table 2, below.

TABLE 2

Compounds of Formula (I)

| ID No. | Compound name |
|---|---|
| 1 | 3-(4-{[1-(4-Chlorophenyl)-1H-pyrrol-2-yl]methoxy}-2,3-dimethylphenyl)propanoic acid |
| 2 | 3-(4-{[1-(4-Ethylphenyl)-1H-pyrrol-2-yl]methoxy}-2,3-dimethylphenyl)propanoic acid |
| 3 | 3-(4-{[1-(4-Bromophenyl)-1H-pyrrol-2-yl]methoxy}-2,3-dimethylphenyl)propanoic acid |
| 4 | 3-(4-{[1-(4-Chlorophenyl)-1H-pyrrol-2-yl]methoxy}-2,3-difluorophenyl)propanoic acid |
| 5 | 3-(4-{[3-Bromo-1-(4-chlorophenyl)-1H-pyrrol-2-yl]methoxy}-2,3-difluorophenyl)propan-1-ol |
| 6 | 3-(4-{[3-Bromo-1-(4-chlorophenyl)-1H-pyrrol-2-yl]methoxy}-2,3-difluorophenyl)propanoic acid |
| 7 | 3-(4-{[3-Chloro-1-(4-chlorophenyl)-1H-pyrrol-2-yl]methoxy}-2,3-dimethylphenyl)propan-1-ol |
| 8 | 3-(4-{[3-Chloro-1-(4-chlorophenyl)-1H-pyrrol-2-yl]methoxy}-2,3-dimethylphenyl)propanoic acid |
| 9 | 3-(4-{[1-(4-Chlorophenyl)-3-cyano-1H-pyrrol-2-yl]methoxy}-2,3-difluorophenyl)propanoic acid |
| 10 | 3-(4-{[3-Chloro-1-(4-chlorophenyl)-1H-pyrrol-2-yl]methoxy}-2,3-difluorophenyl)propan-1-ol |
| 11 | 3-(4-{[3-Chloro-1-(4-chlorophenyl)-1H-pyrrol-2-yl]methoxy}-2,3-difluorophenyl)propanoic acid |
| 12 | 3-(4-{[1-(4-Chlorophenyl)-3-cyano-1H-pyrrol-2-yl]methoxy}-2,3-dimethylphenyl)propanoic acid |
| 13 | 3-(4-{[3-Bromo-1-(4-chlorophenyl)-1H-pyrrol-2-yl]methoxy}-2,3-dimethylphenyl)propan-1-ol |
| 14 | 3-(4-{[3-Bromo-1-(4-chlorophenyl)-1H-pyrrol-2-yl]methoxy}-2,3-dimethylphenyl)propanoic acid |
| 15 | 3-(4-{[1-(4-Chlorophenyl)-3-(trifluoromethyl)-1H-pyrrol-2-yl]methoxy}-2,3-dimethylphenyl)propanoic acid |
| 16 | 3-(4-{[1-(4-Chlorophenyl)-3-(trifluoromethyl)-1H-pyrrol-2-yl]methoxy}-2,3-difluorophenyl)propanoic acid |
| 17 | 3-(4-{[1-(4-Chlorophenyl)-3-(trifluoromethyl)-1H-pyrrol-2-yl]methoxy}-2,3-dimethylphenyl)propan-1-ol |
| 18 | 3-(4-{[1-(4-Bromophenyl)-3-(trifluoromethyl)-1H-pyrrol-2-yl]methoxy}-2,3-dimethylphenyl)propan-1-ol |
| 19 | 3-(2,3-Dimethyl-4-{[1-phenyl-3-(trifluoromethyl)-1H-pyrrol-2-yl]methoxy}phenyl)propan-1-ol |
| 20 | 3-(4-{[1-(4-Bromophenyl)-3-(trifluoromethyl)-1H-pyrrol-2-yl]methoxy}-2,3-difluorophenyl)propanoic acid |
| 21 | 3-(4-{[1-(4-Bromophenyl)-3-(trifluoromethyl)-1H-pyrrol-2-yl]methoxy}-2,3-difluorophenyl)propan-1-ol |
| 22 | 3-(4-{[1-(4-Bromophenyl)-3-(trifluoromethyl)-1H-pyrrol-2-yl]methoxy}-3,5-difluorophenyl)propanoic acid |
| 23 | 3-(4-{[1-(4-Bromophenyl)-3-(trifluoromethyl)-1H-pyrrol-2-yl]methoxy}-2,3-dimethylphenyl)propanoic acid |
| 24 | 3-(4-{[1-(4-Methoxyphenyl)-3-(trifluoromethyl)-1H-pyrrol-2-yl]methoxy}-2,3-dimethylphenyl)propanoic acid |
| 25 | 3-(4-{[1-(4-Methoxyphenyl)-3-(trifluoromethyl)-1H-pyrrol-2-yl]methoxy}-2,3-dimethylphenyl)propan-1-ol |
| 26 | 3-(2,3-Difluoro-4-{[1-(4-methoxyphenyl)-3-(trifluoromethyl)-1H-pyrrol-2-yl]methoxy}phenyl)propanoic acid |
| 27 | 3-(2,3-Difluoro-4-{[1-(4-methoxyphenyl)-3-(trifluoromethyl)-1H-pyrrol-2-yl]methoxy}phenyl)propan-1-ol |
| 28 | 3-(3,5-Difluoro-4-{[1-(4-methoxyphenyl)-3-(trifluoromethyl)-1H-pyrrol-2-yl]methoxy}phenyl)propanoic acid |
| 29 | 3-(4-{[1-(4-Chlorophenyl)-3-(trifluoromethyl)-1H-pyrrol-2-yl]methoxy}-2,3-difluorophenyl)propan-1-ol |
| 30 | 3-(4-{[1-(4-Bromophenyl)-3-(trifluoromethyl)-1H-pyrrol-2-yl]methoxy}-3,5-difluorophenyl)propan-1-ol |
| 31 | 3-(3,5-Difluoro-4-{[1-(4-methoxyphenyl)-3-(trifluoromethyl)-1H-pyrrol-2-yl]methoxy}phenyl)propan-1-ol |
| 32 | 3-(4-{[1-(4-Ethylphenyl)-3-(trifluoromethyl)-1H-pyrrol-2-yl]methoxy}-3,5-difluorophenyl)propanoic acid |
| 33 | 3-(4-{[1-(4-Ethylphenyl)-3-(trifluoromethyl)-1H-pyrrol-2-yl]methoxy}-3,5-difluorophenyl)propan-1-ol |
| 34 | 3-(4-{[1-(4-Ethylphenyl)-3-(trifluoromethyl)-1H-pyrrol-2-yl]methoxy}-2,3-difluorophenyl)propanoic acid |
| 35 | 3-(3,5-Difluoro-4-{[1-phenyl-3-(trifluoromethyl)-1H-pyrrol-2-yl]methoxy}phenyl)propan-1-ol |
| 36 | 3-(4-{[1-(4-Ethylphenyl)-3-(trifluoromethyl)-1H-pyrrol-2-yl]methoxy}-2,3-dimethylphenyl)propanoic acid |
| 37 | 3-(3,5-Difluoro-4-{[1-(4-methylphenyl)-3-(trifluoromethyl)-1H-pyrrol-2-yl]methoxy}phenyl)propan-1-ol |
| 38 | 3-(3,5-Difluoro-4-{[1-phenyl-3-(trifluoromethyl)-1H-pyrrol-2-yl]methoxy}phenyl)propanoic acid |
| 39 | 3-(3,5-Difluoro-4-{[1-(4-methylphenyl)-3-(trifluoromethyl)-1H-pyrrol-2-yl]methoxy}phenyl)propanoic acid |
| 40 | 3-(4-{[1-(4-Ethylphenyl)-3-(trifluoromethyl)-1H-pyrrol-2-yl]methoxy}-2,3-dimethylphenyl)propan-1-ol |
| 41 | 3-(4-{[1-(4-Ethylphenyl)-3-(trifluoromethyl)-1H-pyrrol-2-yl]methoxy}-2,3-difluorophenyl)propan-1-ol |
| 42 | 3-(2,3-Difluoro-4-{[1-(4-methylphenyl)-3-(trifluoromethyl)-1H-pyrrol-2-yl]methoxy}phenyl)propanoic acid |
| 43 | 3-(2,3-Dimethyl-4-{[1-(4-methylphenyl)-3-(trifluoromethyl)-1H-pyrrol-2-yl]methoxy}phenyl)propanoic acid |
| 44 | 3-(2,3-Difluoro-4-{[1-(4-methylphenyl)-3-(trifluoromethyl)-1H-pyrrol-2-yl]methoxy}phenyl)propan-1-ol |
| 45 | 3-(2,3-Dimethyl-4-{[1-(4-methylphenyl)-3-(trifluoromethyl)-1H-pyrrol-2-yl]methoxy}phenyl)propan-1-ol |
| 46 | 3-(4-{[1-(4-Chlorophenyl)-3-(trifluoromethyl)-1H-pyrrol-2-yl]methoxy}-3,5-difluorophenyl)propan-1-ol |
| 47 | 3-(2,3-Difluoro-4-{[1-(6-methylpyridin-3-yl)-3-(trifluoromethyl)-1H-pyrrol-2-yl]methoxy}phenyl)propan-1-ol |
| 48 | 3-(3,5-Difluoro-4-{[1-(6-methylpyridin-3-yl)-3-(trifluoromethyl)-1H-pyrrol-2-yl]methoxy}phenyl)propan-1-ol |
| 49 | 3-(3,5-Difluoro-4-{[1-(6-methylpyridin-3-yl)-3-(trifluoromethyl)-1H-pyrrol-2-yl]methoxy}phenyl)propanoic acid |
| 50 | 3-(2,3-Difluoro-4-{[1-(6-methoxypyridin-3-yl)-3-(trifluoromethyl)-1H-pyrrol-2-yl]methoxy}phenyl)propan-1-ol |
| 51 | 3-(3,5-Difluoro-4-{[1-(6-methoxypyridin-3-yl)-3-(trifluoromethyl)-1H-pyrrol-2-yl]methoxy}phenyl)propanoic acid |
| 52 | 3-(3,5-Difluoro-4-{[1-(6-methoxypyridin-3-yl)-3-(trifluoromethyl)-1H-pyrrol-2-yl]methoxy}phenyl)propan-1-ol |
| 53 | 3-(2,3-Difluoro-4-{[1-(6-methylpyridin-3-yl)-3-(trifluoromethyl)-1H-pyrrol-2-yl]methoxy}phenyl)propanoic acid |
| 54 | 3-(4-{[1-(6-Ethylpyridin-3-yl)-3-(trifluoromethyl)-1H-pyrrol-2-yl]methoxy}-2,3-difluorophenyl)propan-1-ol |
| 55 | 3-(4-{[1-(6-Ethylpyridin-3-yl)-3-(trifluoromethyl)-1H-pyrrol-2-yl]methoxy}-3,5-difluorophenyl)propan-1-ol |
| 56 | 3-(4-{[1-(6-Ethylpyridin-3-yl)-3-(trifluoromethyl)-1H-pyrrol-2-yl]methoxy}-3,5-difluorophenyl)propanoic acid |
| 57 | 3-(2,3-Difluoro-4-{[1-(6-methoxypyridin-3-yl)-3-(trifluoromethyl)-1H-pyrrol-2-yl]methoxy}phenyl)propanoic acid |
| 58 | 3-(4-{[1-(6-Ethylpyridin-3-yl)-3-(trifluoromethyl)-1H-pyrrol-2-yl]methoxy}-2,3-difluorophenyl)propanoic acid |
| 59 | 3-(4-{[1-(4-Chlorophenyl)-3-(trifluoromethyl)-1H-pyrrol-2-yl]methoxy}-3,5-difluorophenyl)-2-methylpropanoic acid |

TABLE 2-continued

Compounds of Formula (I)

| ID No. | Compound name |
|---|---|
| 60 | 3-(3,5-Difluoro-4-{[1-(4-methylphenyl)-3-(trifluoromethyl)-1H-pyrrol-2-yl]methoxy}phenyl)-2-methylpropanoic acid |
| 61 | 3-(4-{[1-(4-Ethylphenyl)-3-(trifluoromethyl)-1H-pyrrol-2-yl]methoxy}-3,5-difluorophenyl)-2-methylpropanoic acid |
| 62 | 3-(3,5-Difluoro-4-{[1-(3-fluoro-4-methylphenyl)-3-(trifluoromethyl)-1H-pyrrol-2-yl]methoxy}phenyl)propanoic acid |
| 63 | 3-(4-{[1-(4-Chlorophenyl)-3-(pentafluoroethyl)-1H-pyrrol-2-yl]methoxy}-3,5-difluorophenyl)propanoic acid |
| 64 | 3-(3,5-Difluoro-4-{[1-(3-fluoro-4-methylphenyl)-3-(trifluoromethyl)-1H-pyrrol-2-yl]methoxy}phenyl)-2-methylpropanoic acid |
| 65 | 3-(3,5-Difluoro-4-{[1-(4-fluorophenyl)-3-(trifluoromethyl)-1H-pyrrol-2-yl]methoxy}phenyl)-2-methylpropanoic acid |
| 66 | 3-(4-{[1-(3-Fluoro-4-methylphenyl)-3-(trifluoromethyl)-1H-pyrrol-2-yl]methoxy}-2,3-dimethylphenyl)propanoic acid |
| 67 | 3-(4-{[1-(4-Chloro-3-fluorophenyl)-3-(trifluoromethyl)-1H-pyrrol-2-yl]methoxy}-3,5-difluorophenyl)propanoic acid |
| 68 | 3-(4-{[1-(4-Chloro-3-fluorophenyl)-3-(trifluoromethyl)-1H-pyrrol-2-yl]methoxy}-2,3-dimethylphenyl)propanoic acid |
| 69 | 3-(4-{[1-(4-Chloro-3-fluorophenyl)-3-(trifluoromethyl)-1H-pyrrol-2-yl]methoxy}-3,5-difluorophenyl)-2-methylpropanoic acid |
| 70 | 3-(4-{[1-(4-Chlorophenyl)-3-(trifluoromethyl)-1H-pyrrol-2-yl]methoxy}-3,5-difluorophenyl)propanoic acid |

In an embodiment, the present invention is directed to compounds of formula (I) selected from the group consisting of 3-(4-{[1-(4-Chlorophenyl)-3-(trifluoromethyl)-1H-pyrrol-2-yl]methoxy}-2,3-dimethylphenyl)propanoic acid; 3-(4-{[1-(4-Ethylphenyl)-3-(trifluoromethyl)-1H-pyrrol-2-yl]methoxy}-2,3-difluorophenyl)propanoic acid; 3-(3,5-Difluoro-4-{[1-(4-methylphenyl)-3-(trifluoromethyl)-1H-pyrrol-2-yl]methoxy}phenyl)propanoic acid; 3-(2,3-Dimethyl-4-{[1-(4-methylphenyl)-3-(trifluoromethyl)-1H-pyrrol-2-yl]methoxy}phenyl)propanoic acid; 3-(4-{[1-(4-Chlorophenyl)-3-(trifluoromethyl)-1H-pyrrol-2-yl]methoxy}-3,5-difluorophenyl)propan-1-ol; 3-(2,3-Difluoro-4-{[1-(6-methoxypyridin-3-yl)-3-(trifluoromethyl)-1H-pyrrol-2-yl]methoxy}phenyl)propanoic acid; 3-(4-{[1-(4-Chlorophenyl)-3-(trifluoromethyl)-1H-pyrrol-2-yl]methoxy}-3,5-difluorophenyl)propanoic acid; and pharmaceutically acceptable salts thereof.

In another embodiment, the present invention is directed to compounds of formula (I) selected from the group consisting of 3-(4-{[1-(4-Ethylphenyl)-3-(trifluoromethyl)-1H-pyrrol-2-yl]methoxy}-2,3-difluorophenyl)propanoic acid; 3-(3,5-Difluoro-4-{[1-(4-methylphenyl)-3-(trifluoromethyl)-1H-pyrrol-2-yl]methoxy}phenyl)propanoic acid; 3-(4-{[1-(4-Chlorophenyl)-3-(trifluoromethyl)-1H-pyrrol-2-yl]methoxy}-3,5-difluorophenyl)propanoic acid; and pharmaceutically acceptable salts thereof.

In an embodiment, the present invention is directed to a compound of formula (I); wherein the compound of formula has a measured $EC_{50}$ according to the β-arrestin A procedure taught in Biological Example 1, which follows herein or less than about 1.0 mM, preferably less than about 0.500 mM, more preferably less than about 0.200 mM, more preferably less than about 0.100 mM, more preferably less than about 0.050 mM.

In an embodiment, the present invention is directed to a compound of formula (I); wherein the compound of formula has a measured $EC_{50}$ according to the Calcium A procedure taught in Biological Example 2, which follows herein or less than about 1.0 mM, preferably less than about 0.500 mM, more preferably less than about 0.200 mM, more preferably less than about 0.100 mM, more preferably less than about 0.050 mM.

Definitions

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl and the like. Unless otherwise noted, the term "$C_{X-Y}$ alkyl" wherein X and Y are integers shall include straight and branched chain composition of between X and Y carbon atoms. For example, "$C_{1-4}$alkyl" shall include straight and branched chain composition of between 1 and 4 carbon atoms, including methyl, ethyl, n-propyl, isopropyl, n-butyl, isobutyl and t-butyl.

One skilled in the art will recognize that the term "—($C_{1-4}$ alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, unless otherwise noted, the term "fluoro substituted $C_{1-4}$alkyl" shall mean any $C_{1-4}$alkyl group as defined above substituted with at least one fluoro atom, preferably substituted with one to three fluoro atoms. Suitable examples include but are not limited to —$CF_3$, —$CH_2$—$CF_3$, —$CF_2$—$CF_2$—$CF_2$—$CF_3$, —$CF_2$—$CF_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, the term "$C_{X-Y}$alkoxy" wherein X and Y are integers shall include an oxygen ether radical as described above of between X and Y carbon atoms. For example, "$C_{1-4}$allkoxy" shall include oxygen ether radicals of between 1 and 4 carbon atoms, including methoxy, ethoxy, n-propoxy, isopropoxy, n-butoxy, isobutoxy and t-butoxy.

One skilled in the art will recognize that the term "—($C_{1-4}$ alkoxy)-" shall denote any oxygen ether radicals of between 1 and 4 carbon atoms as herein defined, wherein said $C_{1-4}$alkoxy is divalent and is further bound through two points of attachment, preferably through two terminal carbon atoms.

As used herein, unless otherwise noted, the term "fluoro substituted $C_{1-4}$alkoxy" shall mean any $C_{1-4}$alkoxy group as defined above substituted with at least one fluoro atom, preferably substituted with one to three fluoro atoms. Suitable examples include but are not limited to —O—$CF_3$, —O—$CH_2$—$CF_3$, —O—$CF_2$—$CF_2$—$CF_2$—$CF_3$, —O—$CF_2$—$CF_3$, and the like.

When a particular group is "substituted" (e.g., $C_{1-4}$alkyl, $C_{2-4}$alkenyl, $C_{2-4}$alkynyl, $C_{5-6}$cycloalkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$, $^{125}I$, $^{131}I$, $^{76}Br$, $^{76}Br$, $^{77}Br$ and $^{82}Br$. Preferably, the radioactive isotope is selected from the group of $^3H$, $^{11}C$ and $^{18}F$.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

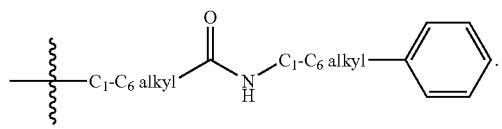

Further, unless otherwise noted, for the R$^3$ substituent groups, the following substitution numbering pattern around the phenyl ring on the compound of formula (I) will apply:

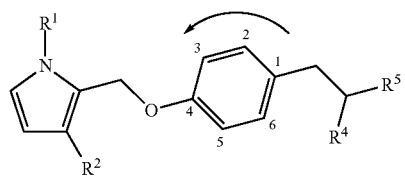

Abbreviations used in the specification, particularly the Schemes and Examples, are as follows:
ADDP=1,1'-(azodicarbonyl)dipiperidine
n-BuLi=n-Butyl Lithium
Bu$_3$P=Tributylphosphine
Cu(OAc)$_2$=Copper Acetate
DCE=Dichloroethane
DCM=Dichloromethane
DIBAL=Diisobutylaluminium hydride
DIPEA or DIEA=Diisopropylethylamine
DMF=N,N-Dimethylformamide
DMSO=Dimethylsulfoxide
dppf=1,1'-Bis(diphenylphosphino)ferrocene
EtOAc=Ethyl acetate
HPLC=High Pressure Liquid Chromatography
LAH=Lithium aluminum hydride
LDL=Low density Lipoprotein
Me=Methyl (i.e. —CH$_3$)
MeCN=Acetonitrile
MeOH=Methanol
MOM=Methoxy methyl ether
MTBE=Methyl t-butyl ether
NaOMe=Sodium Methoxide
NMP=N-methyl-2-pyrrolidinone
Pd/C=Palladium on Carbon Catalyst
Pd$_2$(OAc)$_2$=Palladium(II)acetate
Pd$_2$(dba)$_3$=Tris(dibenzylidene acetone)dipalladium(0)
P(o-tol)$_3$=Tri(o-tolyl)phosphine
Pd(PPh$_3$)$_4$=Tetrakistriphenylphosphine palladium (0)
PPh$_3$=Triphenylphosphine
TBAF=Tetra-n-butylammonium fluoride
TEA=Triethylamine
THF=Tetrahydrofuran
THP=Tetrahydropyranyl
TIPS=Triisopropylsilyl
Tosyl=p-Toluenesulfonyl For purposes of the present invention, the term "modulated by the GPR120 receptor" is used to refer to the condition of being affected by the modulation of the GPR120 receptor, including but not limited to, the state of being mediated by the GPR120 receptor.

As used herein, unless otherwise noted, the term "disorder modulated by the GPR120 receptor" shall mean any disease, disorder or condition characterized in that at least one of its characteristic symptoms is alleviated or eliminated upon treatment with a GPR120 receptor agonist. Suitably examples include, but are not limited to obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus, dyslipidemia or metabolic syndrome X; more preferably, Type II diabetes mellitus or dyslipidemia.

As used herein unless otherwise noted, the term "obesity related cardiovascular disorders" shall mean any cardiovascular disease, disorder or condition in which obesity or diabetes (preferably, Type II Diabetes) has a role in the initiation or exacerbation of said disorder or condition. Suitable examples include, but are not limited to, hypertension, atherosclerosis and cardiac fibrosis.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications (including, to reduce the frequency or severity of one or more symptoms), or eliminate the disease, condition, or disorder.

As used herein, unless otherwise noted, the term "prevention" shall include (a) the delay or avoidance of the development of additional symptoms; and/or (b) delay or avoidance of the development of the disorder or condition along a known development pathway.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. A subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter. One skilled in the art will further recognize that wherein a reaction step of the present invention may be carried out in a variety of solvents or solvent systems, said reaction step may also be carried out in a mixture of the suitable solvents or solvent systems.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed according to the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives-groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed according to the reaction. Suitable oxygen protecting groups include, but are not limited to, acetyl, benzyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[($Rmoles-Smoles$)/($Rmoles+Smoles$)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

$ee=([\alpha-obs]/[\alpha-max])\times100$.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the according to: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the according to: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the according to: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthetic Methods

Compounds of formula (I) may be prepared according to the process outlined in Scheme 1, below.

Scheme 1

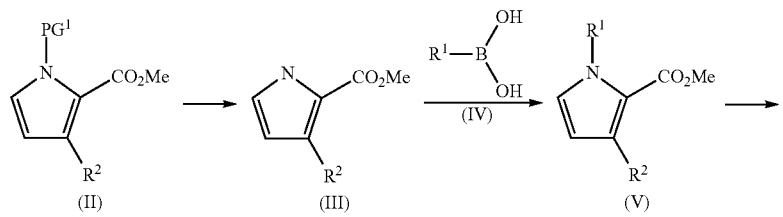

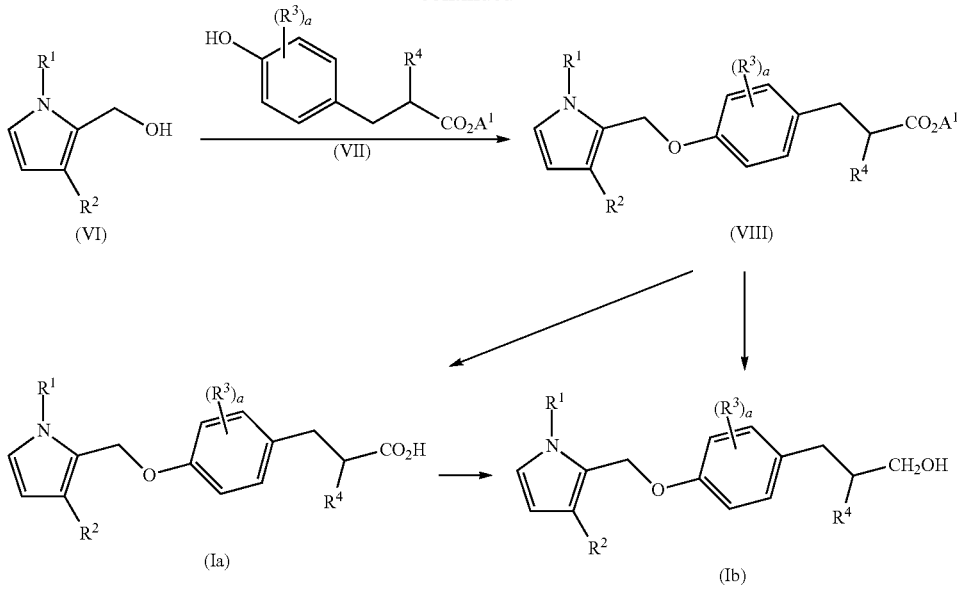

Accordingly, a suitably substituted compound of formula (II), wherein $PG^1$ is a suitably selected nitrogen protecting group such as —$SO_2$-phenyl, TIPS, and the like, a known compound or compound prepared by known methods, is de-protected, according to known methods; to yield the corresponding compound of formula (III). For example, wherein $PG^1$ is —$SO_2$-phenyl, the compound of formula (II) may be de-protected by reacting with a suitably selected reagent such as $NaOCH_3$ in methanol, or with TBAF in a suitable solvent such as THF.

The compound of formula (III) is reacted with a suitably substituted boronic acid, a compound of formula (IV), a known compound or compound prepared by known methods, in the presence of a suitably selected metal catalyst such as copper (II) acetate, copper chloride, and the like; in the presence of a suitably selected base such as pyridine, TEA, and the like; in a suitably selected solvent such as DCM, DCE, and the like; to yield the corresponding compound of formula (V).

The compound of formula (V) is reacted with a suitably selected reducing agent such as LAH, DIBAL, $NaBH_4$, and the like; in a suitably selected solvent such as diethyl ether, THF, toluene, and the like; at a temperature in the range of from about −78° C. to about room temperature; to yield the corresponding compound of formula (VI).

The compound of formula (VI) is reacted with a suitably substituted compound of formula (VII), wherein $A^1$ is $C_{1-4}$alkyl, preferably ethyl, a known compound or compound prepared by known methods, in the presence of a suitably selected phosphine such as such as tri-n-burtylphosphine, triphenylphosphine, and the like; in the presence of a suitably selected Mitsunobu reagent such as ADDP, DEAD, DIAD, and the like; in a suitably selected solvent such as THF, toluene, and the like; at a temperature in the range of from about 0° C. to about 70° C.; to yield the corresponding compound of formula (VIII).

The compound of formula (VIII) is hydrolyzed according to known methods; to yield the corresponding compound of formula (Ia). For example, the compound of formula (VIII) may be hydrolyzed by reacting with a suitably selected base such as NaOH, LiOH, and the like; or by reacting with a suitably selected acid such as HCl, and the like; in a suitably selected solvent such as methanol, THF, 1,4-dioxane, and the like; at a temperature of in the range of from about 0° C. to about 100° C.

Alternatively, the compound of formula (VIII) may be reacted with a suitably selected reducing agent such as LAH, DIBAL, $NaBH_4$, and the like; in a suitably selected solvent such as THF, toluene, methanol, and the like; at a temperature in the range of from about −78° C. to about room temperature; to yield the corresponding compound of formula (Ib).

Compounds of formula (II) are known compounds or compounds which may be prepared by known methods. Compounds of formula (II) wherein $PG^1$ is —$SO_2$-phenyl and wherein $R^2$ is trifluoromethyl may be prepared as described in Scheme 2, below.

Scheme 2

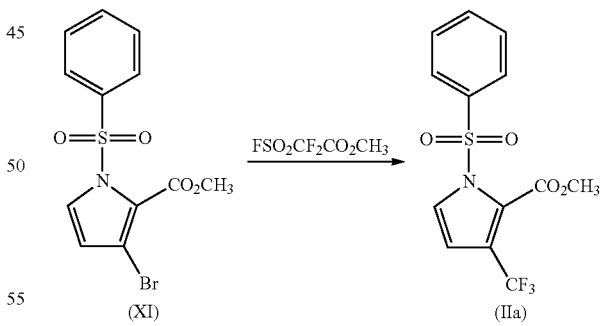

Accordingly, a suitably substituted compound of formula (IX), a compound prepared as described in (FUKUDA, T., et al., *Organic Letters,* 2010, pp 2734-2737, Vol. 12) is reacted with a suitably selected reagent such as $FSO_2CF_2CO_2CH_3$, and the like; in the presence of a suitably selected copper reagent such as CuI, and the like; in a suitably selected solvent such as DMF, NMP, and the like; at a temperature in the range of from about 20° C. to about 120° C.; to yield a mixture of starting material and the corresponding compound of formula (IIa).

The mixture of the compound of formula (IX) and the compound of formula (IIa) is reacted with $H_2(g)$ at a pressure in the range of from about atmospheric pressure to about 50 psi; in the presence of a suitably selected catalysis such as 5% Pd/C, and the like; in a suitably selected solvent such as ethanol, methanol, and the like; to yield the corresponding compound of formula (IIa).

Compounds of formula (I) wherein $R^2$ is cyano may be prepared from the corresponding compound of formula (VIII), wherein $R^2$ is bromo. More particularly, a suitably substituted compound of formula (VIII), wherein $R^2$ is bromo is reacted with a suitably selected reagent such as zinc cyanide, copper cyanide, and the like; in the presence of a suitably selected palladium catalysts such as $Pd_2(dba)_3$, $Pd(OAc)_2$, and the like; in the presence of a suitably selected ligand such as dppf, and the like; in a suitably selected solvent such as DMF, NMP, and the like; at a temperature in the range of from about room temperature to about 170° C.; to yield the corresponding compound of formula (VIII), wherein $R^2$ is cyano.

The compound of formula (VIII) wherein $R^2$ is cyano is then reacted as described in Scheme 1, above, to yield the corresponding compound of formula (I), wherein $R^2$ is cyano.

Compounds of formula (VII) are known compounds or compounds which may be prepared according to known methods. For example, compounds of formula (VII) may be prepared according to the procedure as described in Scheme 3, below.

is a suitably selected oxygen protecting group such as benzyl, t-butyldimethylsilyl, and the like. For example, the compound of formula (XI) may be reacted with benzylchloride or benzylbromide, in the presence of a suitably selected base such as NaH, $K_2CO_3$, and the like; in a suitably selected solvent such as DMF, acetone, THF, and the like; at a temperature in the range of from about room temperature to about 100° C.; to yield the corresponding compound of formula (XII), wherein $PG^2$ is benzyl.

The compound of formula (XII) is reacted with a suitably substituted phosphorane compound of formula (XIII), a known compound or compound prepared by known methods; in a suitably selected solvent such as THF, 1,4-dioxane, 1,2-dimethoxyethane, and the like; at a temperature in the range of from about room temperature to about 100° C.; to yield the corresponding compound of formula (XIV).

The compound of formula (XIV) is de-protected according to known methods; to yield the corresponding compound of formula (VII). For example, wherein $PG^2$ is benzyl, the compound of formula (XIV) may be de-protected by reacting with $H_2(g)$; in the presence of a suitably selected catalyst such as 5% Pd/C; in a suitably selected solvent such as ethanol, ethyl acetate, and the like; to yield the corresponding compound of formula (VII).

Compounds of formula (VII) may alternatively be prepared according to the procedure outlined in Scheme 4, below.

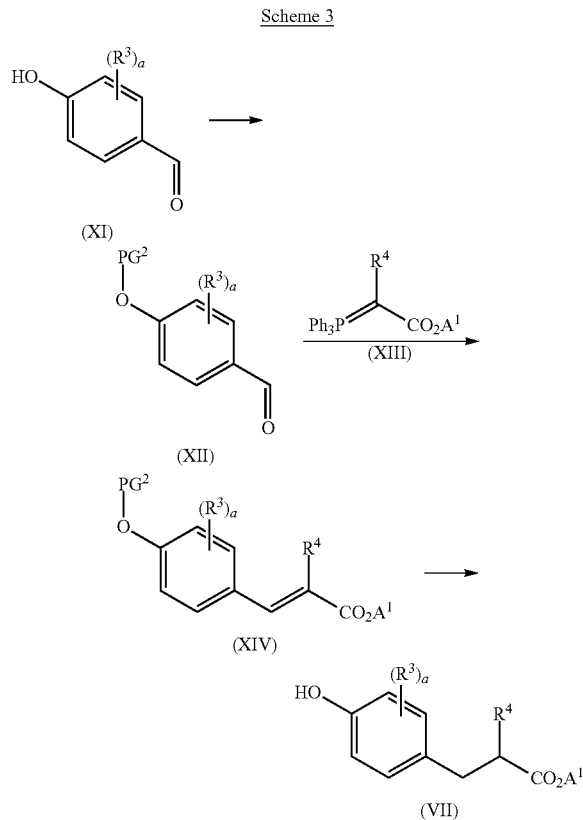

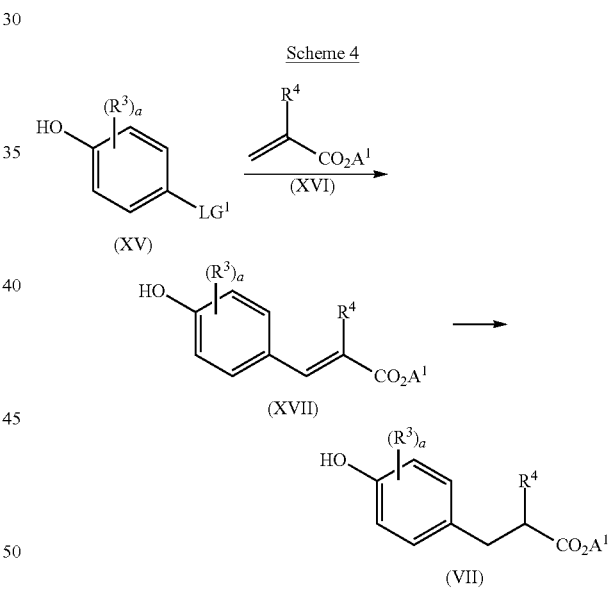

Accordingly, a suitably substituted compound of formula (XI), a known compound or compound prepared by known methods, is protected according to known methods; to yield the corresponding compound of formula (XII), wherein $PG^2$ Accordingly, a suitably substituted compound of formula (XV), wherein $LG^1$ is a suitably selected leaving group such as I, Br, and the like, a known compound or compound prepared by known methods, is reacted with a suitably substituted compound of formula (XVI), a known compound or compound prepared by known methods; in the presence of a suitably selected palladium catalysts such as $Pd(OAc)_2$, $Pd_2(dba)_3$, and the like; in the presence of a suitably selected ligand such as $P(o-tol)_3$, $PPh_3$, and the like; in the presence of a suitably selected base such as TEA, DIPEA, pyridine, and the like; in a suitably selected solvent such as DMF, 1,4-dioxane, THF, and the like; at a temperature in the range of from about room temperature to about 100° C.; to yield the corresponding compound of formula (XVII).

The compound of formula (XVII) is reacted with a suitably selected reducing agent such as $H_2(g)$; in the presence of a suitably selected catalyst such as 5% Pd/C; in a suitably selected solvent such as ethanol, ethyl acetate, and the like; to yield the corresponding compound of formula (VII).

Pharmaceutical Compositions

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 100 mg/kg/day, or any amount or range therein, preferably from about 0.5 mg/kg/day to about 50 mg/kg/day, preferably from about 1.0 mg/kg/day to about 25 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method(s) of treating disorders as described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders, as described herein, is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.1 to about 100.0 mg/kg of body weight per day, or any amount or range therein. More preferably, from about 0.5 to about 50.0 mg/kg of body weight per day, or any amount or range therein. More preferably, from about 1.0 to about 25.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

SYNTHESIS EXAMPLES

The according to Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

3-(4-((1-(4-chlorophenyl)-3-(trifluoromethyl)-1H-pyrrol-2-yl)methoxy)-3,5-difluorophenyl)propanoic acid (Compound #70)

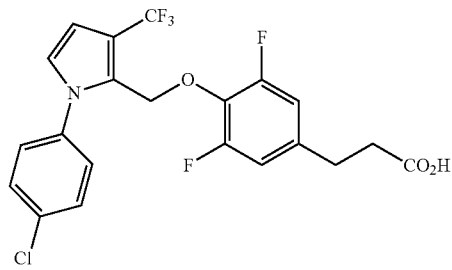

Step A: methyl 1-(phenylsulfonyl)-3-(trifluoromethyl)-1H-pyrrole-2-carboxylate

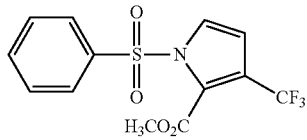

A suspension of methyl 3-bromo-1-(phenylsulfonyl)-1H-pyrrole-2-carboxylate (3.07 g, 8.0 mmol, 1 eq), methyl 2,2-difluoro-2-(fluorosulfonyl)acetate (6.32 mL, 48.1 mmol, 6 eq) and CuI (1.53 g, 8.0 mmol, 1 eq) in NMP (20 mL) was heated to 80° C. under $N_2$ overnight. Additional methyl 2,2-difluoro-2-(fluorosulfonyl)acetate (6.32 mL, 48.1 mmol, 6 eq) and CuI (1.53 g, 8.0 mmol, 1 eq) were added and the resulting mixture heated overnight. The resulting brown suspension was filtered through CELITE with diethyl ether, the diethyl ether solution was washed with water, saturated $NaHCO_3$, brine, dried over $MgSO_4$ and then concentrated. The resulting residue was purified by flash chromatography (400 g column) eluting with 5 to 20% EtOAc/heptane to yield 66:34 mixture of methyl 1-(phenylsulfonyl)-3-(trifluoromethyl)-1H-pyrrole-2-carboxylate and starting material.

A solution of this mixture and 5% Pd/C (300 mg, Degussa type) in EtOH (15 mL) was placed under a balloon of $H_2$ overnight. The resulting suspension was filtered through CELITE, washed with EtOAc and concentrated. The resulting residue was purified by flash chromatography (150 g column) eluting with 5 to 20% EtOAc/heptane to yield methyl 1-(phenylsulfonyl)-3-(trifluoromethyl)-1H-pyrrole-2-carboxylate.

$^1$H NMR (CHLOROFORM-d) δ: 8.02 (d, J=8.1 Hz, 2H), 7.70 (t, J=7.3 Hz, 1H), 7.59 (t, J=7.8 Hz, 2H), 7.48 (d, J=3.5 Hz, 1H), 6.51 (d, J=3.5 Hz, 1H), 3.89 (s, 3H). Calculated for C13H10F3NO4S: 359.2 (M+23); found: 359.2.

Step B: methyl 3-(trifluoromethyl)-1H-pyrrole-2-carboxylate

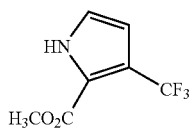

To a solution of the product prepared in Step A (704 mg, 1.9 mmol, 1 eq) in methanol (10 mL) was added a solution of NaOMe in MeOH (2.46 mL of a 25% solution, 10.6 mmol, 5.6 eq). After 1 hr, 1 N HCl was added, the aqueous was extracted with diethyl ether, washed with brine, dried over $MgSO_4$ and concentrated to yield methyl 3-(trifluoromethyl)-1H-pyrrole-2-carboxylate.

$^1$H NMR (CHLOROFORM-d) δ: 9.42 (br. s., 1H), 6.92 (t, J=3.0 Hz, 1H), 6.55 (t, J=3.0 Hz, 1H), 3.92 (s, 3H). Calculated for C7H6F3NO2: 194.0 (M+1); found: 194.0.

Step C: methyl 1-(4-chlorophenyl)-3-(trifluoromethyl)-1H-pyrrole-2-carboxylate

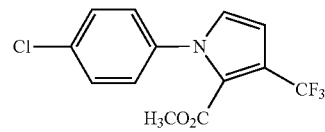 [SMILES: COC(=O)c1c(C(F)(F)F)ccn1-c1ccc(Cl)cc1]

A suspension of the product prepared in Step B (1160 mg, 6.0 mmol, 1 eq), 4-chlorophenylboronic acid (2.9 g, 18.0 mmol, 1 eq), Cu(OAc)$_2$ (2.18 g, 12.0 mmol, 2 eq), 4 A molecular sieves (3 g), pyridine (1.94 mL, 4.0 mmol, 4 eq) in DCM (40 mL) was stirred at room temperature for 2 days. The resulting suspension was filtered through CELITE, washed with DCM, and concentrated. The resulting residue was dry packed and purified by flash chromatography (120 g column) eluting with 4 to 8% EtOAc/heptane to yield methyl 1-(4-chlorophenyl)-3-(trifluoromethyl)-1H-pyrrole-2-carboxylate.

$^1$H NMR (CHLOROFORM-d) δ: 7.43 (d, J=8.6 Hz, 2H), 7.23 (d, J=8.6 Hz, 2H), 6.86 (d, J=3.0 Hz, 1H), 6.59 (d, J=3.0 Hz, 1H), 3.76 (s, 3H). Calculated for C13H9ClF3NO2: 304.0 (M+1); found: 304.0.

Step D: (1-(4-chlorophenyl)-3-(trifluoromethyl)-1H-pyrrol-2-yl)methanol

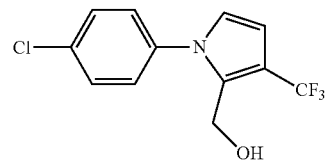 [SMILES: OCc1c(C(F)(F)F)ccn1-c1ccc(Cl)cc1]

To a solution of the product prepared in Step C (500 mg, 1.48 mmol, 1 eq) in THF (10 mL) at 0° C. under $N_2$ was added LAH (1.48 mL of a 2 M solution in THF, 2.96 mmol, 2 eq). After 1 hr, saturated sodium potassium tartrate (5 mL) was added dropwise at first, the solution was warmed to room temperature, diethyl ether was added, the solution decanted from the solid, washed with brine, dried over $MgSO_4$ and concentrated to yield (1-(4-chlorophenyl)-3-(trifluoromethyl)-1H-pyrrol-2-yl)methanol.

$^1$H NMR (CHLOROFORM-d) δ: 7.39-7.51 (m, 4H), 6.81 (d, J=3.0 Hz, 1H), 6.48 (d, J=3.0 Hz, 1H), 4.54 (d, J=6.1 Hz, 2H), 1.77 (t, J=6.1 Hz, 1H). Calculated for C12H9ClF3NO: 258.0 (M–17); found: 258.0.

Step E: ethyl 3-(4-((1-(4-chlorophenyl)-3-(trifluoromethyl)-1H-pyrrol-2-yl)methoxy)-3,5-difluorophenyl)propanoate

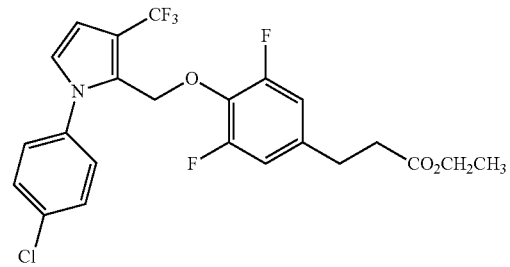

A solution of the product prepared in Step D (1.33 g, 4.84 mmol, 1 eq), ethyl 3-(3,5-difluoro-4-hydroxyphenyl)propanoate (1.78 g, 7.74 mmol, 1.6 eq), 1,1'-(azodicarbonyl)dipiperidine (2.52 g, 9.68 mmol, 2 eq) and tri-n-butylphosphine (3.08 mL, 12.1 mmol, 2.5 eq) in toluene (85 mL) was heated to 60° C. under $N_2$. After 3 hr, heptane (170 mL) was added and the resulting suspension allowed to cool to room temperature over 30 min. The resulting white solid byproduct was filtered, washed with heptane, and the filtrate concentrated. The resulting residue was purified by flash chromatography (120 g column) eluting with 2 to 12% EtOAc/heptane to yield ethyl 3-(4-((1-(4-chlorophenyl)-3-(trifluoromethyl)-1H-pyrrol-2-yl)methoxy)-3,5-difluorophenyl)propanoate.

$^1$H NMR (CHLOROFORM-d) δ: 7.49-7.55 (m, J=8.6 Hz, 2H), 7.42-7.49 (m, J=8.6 Hz, 2H), 6.87 (d, J=3.0 Hz, 1H), 6.67-6.77 (m, 2H), 6.49 (d, J=3.0 Hz, 1H), 4.95 (s, 2H), 4.13 (q, J=7.1 Hz, 2H), 2.86 (t, J=7.6 Hz, 2H), 2.57 (t, J=7.6 Hz, 2H), 1.24 (t, J=7.3 Hz, 3H). Calculated for C23H19ClF5NO3: 510.1 (M+23); found: 510.0.

Step F: 3-(4-((1-(4-chlorophenyl)-3-(trifluoromethyl)-1H-pyrrol-2-yl)methoxy)-3,5-difluorophenyl) propanoic acid

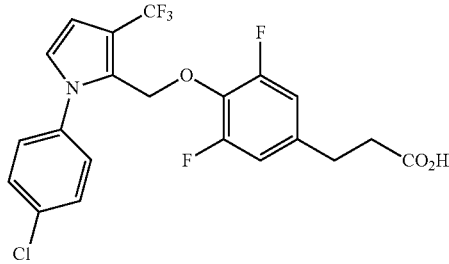 [SMILES: O=C(O)CCc1cc(F)c(OCc2c(C(F)(F)F)ccn2-c2ccc(Cl)cc2)c(F)c1]

To a solution of the product prepared Step E (1.70 g, 3.48 mmol, 1 eq) in THF (30 mL) and MeOH (30 mL) at room temperature was added LiOH (15 mL of a 1 M aq solution, 15 mmol, 4.3 eq). After 3 hrs, 1 N HCl was added, the aqueous extracted with DCM, dried over MgSO$_4$ and concentrated to yield 3-(4-((1-(4-chlorophenyl)-3-(trifluoromethyl)-1H-pyrrol-2-yl)methoxy)-3,5-difluorophenyl)propanoic acid.

$^1$H NMR (CHLOROFORM-d) δ: 7.49-7.56 (m, 2H), 7.43-7.49 (m, 2H), 6.88 (d, J=2.5 Hz, 1H), 6.69-6.78 (m, 2H), 6.49 (d, J=2.5 Hz, 1H), 4.96 (s, 2H), 2.88 (t, J=7.6 Hz, 2H), 2.65 (t, J=7.6 Hz, 2H). Calculated for C21H15ClF5NO3: 482.1 (M+23); found 482.1.

Example 2

3-(4-{[1-(4-Chlorophenyl)-3-(trifluoromethyl)-1H-pyrrol-2-yl]methoxy}-2,3-dimethylphenyl)propan-1-ol (Compound #46)

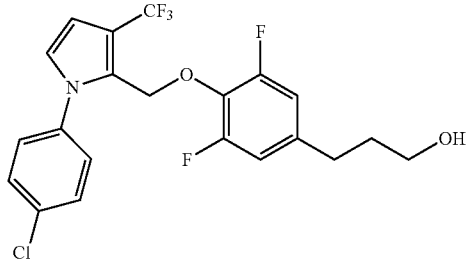 [SMILES: OCCCc1cc(F)c(OCc2c(C(F)(F)F)ccn2-c2ccc(Cl)cc2)c(F)c1]

To a solution of the product prepared in Example 1, Step E (46 mg, 0.10 mmol, 1 eq) in THF (2 mL) at 0° C. under $N_2$ was added LAH (0.20 mL of a 1 M solution in THF, 0.20 mmol, 2 eq). After 1 hr, saturated sodium potassium tartrate (0.5 mL) was added dropwise at first, the solution was warmed to room temperature, diethyl ether was added, washed with brine, dried over MgSO$_4$ and concentrated. The resulting residue was purified by flash chromatography (4 g column) eluting with 10 to 30% EtOAc/heptane to yield 3-(4-{[1-(4-Chlorophenyl)-3-(trifluoromethyl)-1H-pyrrol-2-yl]methoxy}-2,3-dimethylphenyl)propan-1-ol.

$^1$H NMR (300 MHz, CD$_3$OD) δ: 7.56 (s, 4H), 7.05 (d, J=3.0 Hz, 1H), 6.76-6.83 (m, 2H), 4.49 (d, J=3.0 Hz, 1H), 5.00 (s, 2H), 3.55 (t, J=5.7 Hz, 2H), 2.61-2.66 (m, 2H), 1.71-1.84 (m, 2H). Mass spectrum (ESI, m/z): Calculated for C$_{21}$H$_{17}$ClF$_5$NO$_2$, 258.0 (M−C$_{12}$H$_8$ClF$_3$N), found 258.0.

Example 3

3-(4-{[1-(4-Chlorophenyl)-3-(trifluoromethyl)-1H-pyrrol-2-yl]methoxy}-2,3-difluorophenyl)propanoic acid (Compound #16)

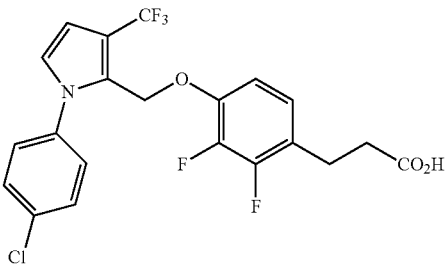

The title compound was prepared by reacting the product prepared in Step D of Example 1 and ethyl 3-(2,3-difluoro-4-hydroxyphenyl)propanoate, according to the procedures described in Example 1, Steps E and F.

$^1$H NMR (CHLOROFORM-d) δ: 7.39-7.50 (m, 4H), 6.82-6.94 (m, 2H), 6.62-6.73 (m, 1H), 6.53 (d, J=2.5 Hz, 1H), 4.90 (s, 2H), 2.94 (t, J=7.3 Hz, 2H), 2.61-2.74 (m, 2H). Calculated for C21H15ClF5NO3: 482.1 (M+23); found 482.1.

Example 4

3-(4-{[1-(4-Chlorophenyl)-3-(trifluoromethyl)-1H-pyrrol-2-yl]methoxy}-2,3-difluorophenyl)propan-1-ol (Compound #29)

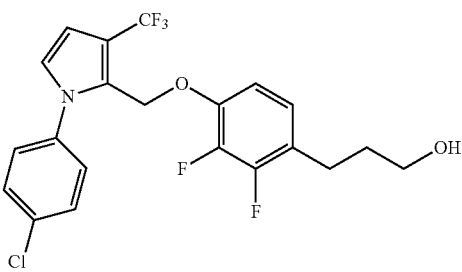

The title compound was prepared by reacting the product prepared in Step D of Example 1 and ethyl 3-(2,3-difluoro-4-hydroxyphenyl)propanoate according to the procedure described in Example 1, Step E, and then according to Example 2.

¹H NMR (CHLOROFORM-d) δ: 7.43 (s, 4H), 6.87 (d, J=3.0 Hz, 1H), 6.84 (td, J=8.2, 2.3 Hz, 1H), 6.61-6.70 (m, 1H), 6.53 (d, J=3.0 Hz, 1H), 4.90 (s, 2H), 3.67 (t, J=6.3 Hz, 2H), 2.71 (t, J=7.6 Hz, 2H), 1.79-1.90 (m, 2H), 1.38 (br. s., 1H). Calculated for C21H17ClF5NO2: 468.1 (M+1); 468.1.

Example 5

3-(4-{[1-(4-Bromophenyl)-3-(trifluoromethyl)-1H-pyrrol-2-yl]methoxy}-2,3-dimethylphenyl)propan-1-ol (Compound #18)

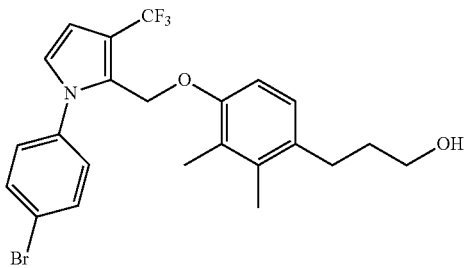

The title compound was prepared by (a) reacting the product prepared in Step B of Example 1 and 4-bromophenylboronic acid according to the procedure described in Example 1, Step C, (b) then reacting the resulting product according to the procedure in Example 1, Step D, (c) then reacting the resulting product with ethyl 3-(2,3-dimethyl-4-hydroxyphenyl)propanoate according to the procedure in Example 1, Step E, and Example 2.

¹H NMR (CHLOROFORM-d) δ: 7.55 (d, J=8.6 Hz, 2H), 7.32 (d, J=8.6 Hz, 2H), 6.92 (d, J=8.6 Hz, 1H), 6.86 (d, J=3.0 Hz, 1H), 6.59 (d, J=8.1 Hz, 1H), 6.54 (d, J=3.0 Hz, 1H), 4.82 (s, 2H), 3.66-3.77 (m, 2H), 2.63-2.73 (m, 2H), 2.21 (s, 3H), 2.09 (s, 3H), 1.76-1.87 (m, 2H), 1.24-1.32 (m, 1H). Calculated for C23H23BrF3NO2: 482.1 (M+1); found 482.1.

Example 6

3-(2,3-Dimethyl-4-{[1-phenyl-3-(trifluoromethyl)-1H-pyrrol-2-yl]methoxy}phenyl)propan-1-ol (Compound #19)

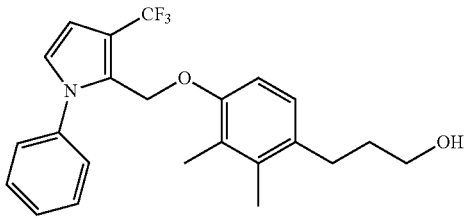 [SMILES: Cc1c(CCCO)ccc(OCc2c(C(F)(F)F)ccn2-c2ccccc2)c1C]

The title compound was prepared by (a) reacting the product prepared in Step B of Example 1 and phenylboronic acid according to the procedure described in Example 1, Step C, (b) then reacting the resulting product according to the procedure in Example 1, Step D, (c) then reacting the resulting product with ethyl 3-(2,3-dimethyl-4-hydroxyphenyl)propanoate according to the procedure in Example 1, Step E, and Example 2.

¹H NMR (CHLOROFORM-d) δ: 7.36-7.46 (m, 5H), 6.86-6.92 (m, 2H), 6.57 (d, J=8.1 Hz, 1H), 6.54 (d, J=3.0 Hz, 1H), 4.84 (s, 2H), 3.69 (q, J=6.1 Hz, 2H), 2.61-2.70 (m, 2H), 2.20 (s, 3H), 2.09 (s, 3H), 1.73-1.85 (m, 2H), 1.22-1.30 (m, 1H). Calculated for C23H24F3NO2: 404.2 (M+1); not found.

Example 7

3-(4-{[1-(4-Bromophenyl)-3-(trifluoromethyl)-1H-pyrrol-2-yl]methoxy}-2,3-difluorophenyl)propanoic acid (Compound #20)

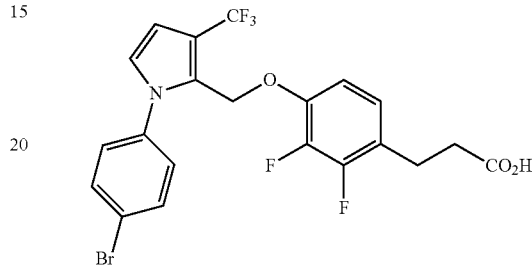

The title compound was prepared by (a) reacting the product prepared in Step B of Example 1 and 4-bromophenylboronic acid according to the procedure described in Example 1, Step C, (b) then reacting the resulting product according to the procedure in Example 1, Step D, and (c) then reacting the resulting product with ethyl 3-(2,3-difluoro-4-hydroxyphenyl)propanoate according to the procedure described in Example 1, Steps E and F.

¹H NMR (CHLOROFORM-d) δ: 7.59 (d, J=8.6 Hz, 2H), 7.36 (d, J=8.6 Hz, 2H), 6.82-6.94 (m, 2H), 6.62-6.74 (m, 1H), 6.53 (d, J=3.0 Hz, 1H), 4.90 (s, 2H), 2.95 (t, J=7.1 Hz, 2H), 2.63-2.78 (m, 2H). Calculated for C21H15BrF5NO3: 526.0 (M+23); found 525.9.

Example 8

3-(4-{[1-(4-Bromophenyl)-3-(trifluoromethyl)-1H-pyrrol-2-yl]methoxy}-2,3-difluorophenyl)propan-1-ol (Compound #21)

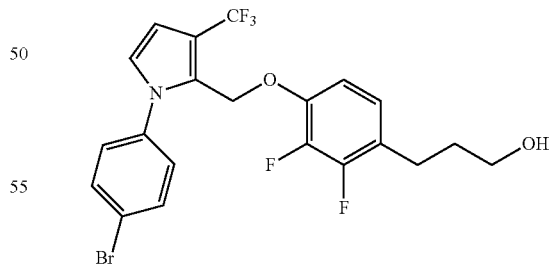

The title compound was prepared by (a) reacting the product prepared in Step B of Example 1 and 4-bromophenylboronic acid according to the procedure described in Example 1, Step C, (b) then reacting the resulting product according to the procedure in Example 1, Step D, (c) then reacting the resulting product with ethyl 3-(2,3-difluoro-4-hydroxyphenyl)propanoate according to the procedure described in Example 1, Step E, and Example 2.

¹H NMR (CHLOROFORM-d) δ: 7.59 (d, J=8.6 Hz, 2H), 7.37 (d, J=9.1 Hz, 2H), 6.80-6.96 (m, 2H), 6.62-6.76 (m, 1H), 6.53 (d, J=3.0 Hz, 1H), 4.90 (s, 2H), 3.62-3.78 (m, 2H), 2.71 (t, J=7.3 Hz, 2H), 1.79-1.96 (m, 2H), 1.38 (br. s., 1H). Calculated for C21H17BrF5NO2: 512.0 (M+23); found 512.0.

Example 9

3-(4-{[1-(4-Bromophenyl)-3-(trifluoromethyl)-1H-pyrrol-2-yl]methoxy}-3,5-difluorophenyl)propanoic acid (Compound #22)

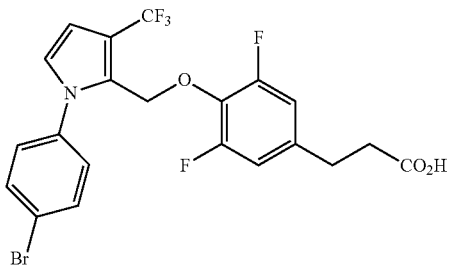

The title compound was prepared by reacting the product prepared in Step B of Example 1 and 4-bromophenylboronic acid according to the procedure described in Example 1, Step C, and then reacting the resulting product according to the procedures in Example 1, Steps D through F.

¹H NMR (CHLOROFORM-d) δ: 7.58-7.69 (m, J=8.6 Hz, 2H), 7.46 (d, J=8.6 Hz, 2H), 6.88 (d, J=3.0 Hz, 1H), 6.67-6.80 (m, J=9.1 Hz, 2H), 6.49 (d, J=3.0 Hz, 1H), 4.96 (s, 2H), 2.87 (t, J=7.6 Hz, 2H), 2.65 (t, J=7.6 Hz, 2H). Calculated for C21H15BrF5NO3: 526.0 (M+23); found 525.9.

Example 10

3-(4-{[1-(4-Bromophenyl)-3-(trifluoromethyl)-1H-pyrrol-2-yl]methoxy}-2,3-dimethylphenyl)propanoic acid (Compound #23)

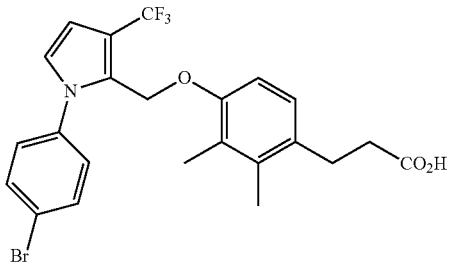

The title compound was prepared by (a) reacting the product prepared in Step B of Example 1 and 4-bromophenylboronic acid according to the procedure described in Example 1, Step C, (b) then reacting the resulting product according to the procedure in Example 1, Step D, and (c) then reacting the resulting product with ethyl 3-(2,3-dimethyl-4-hydroxyphenyl)propanoate according to the procedures described in Example 1, Steps E and F.

¹H NMR (CHLOROFORM-d) δ: 7.52-7.58 (m, J=8.6 Hz, 2H), 7.28-7.34 (m, J=8.6 Hz, 2H), 6.93 (d, J=8.6 Hz, 1H), 6.86 (d, J=3.0 Hz, 1H), 6.59 (d, J=8.1 Hz, 1H), 6.54 (d, J=3.0 Hz, 1H), 4.83 (s, 2H), 2.87-2.97 (m, 2H), 2.53-2.64 (m, 2H), 2.22 (s, 3H), 2.09 (s, 3H). Calculated for C23H21BrF3NO3: 496.1 (M+1); found 496.1.

Example 11

3-(4-{[1-(4-Methoxyphenyl)-3-(trifluoromethyl)-1H-pyrrol-2-yl]methoxy}-2,3-dimethylphenyl)propanoic acid (Compound #)

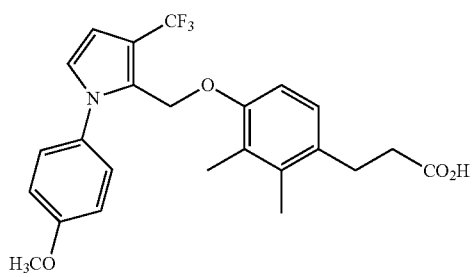

The title compound was prepared by (a) reacting the product prepared in Step B of Example 1 and 4-methoxyphenylboronic acid according to the procedure described in Example 1, Step C, (b) then reacting the resulting product according to the procedure in Example 1, Step D, and (c) then reacting the resulting product with ethyl 3-(2,3-dimethyl-4-hydroxyphenyl)propanoate according to the procedures described in Example 1, Steps E and F.

¹H NMR (CHLOROFORM-d) δ: 7.33 (d, J=9.1 Hz, 2H), 6.91 (d, J=9.1 Hz, 3H), 6.83 (d, J=3.0 Hz, 1H), 6.58 (d, J=8.6 Hz, 1H), 6.50 (d, J=3.0 Hz, 1H), 4.80 (s, 2H), 3.82 (s, 3H), 2.88-2.96 (m, 2H), 2.54-2.63 (m, 2H), 2.21 (s, 3H), 2.11 (s, 3H). Calculated for C24H24F3NO4: 448.2 (M+1); found 448.2.

Example 12

3-(4-{[1-(4-Methoxyphenyl)-3-(trifluoromethyl)-1H-pyrrol-2-yl]methoxy}-2,3-dimethylphenyl)propan-1-ol (Compound #25)

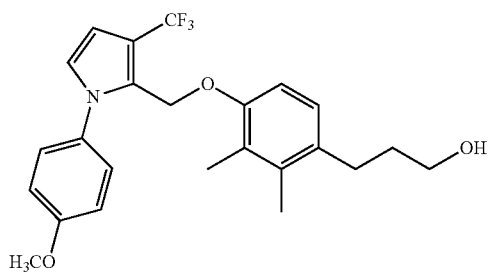 [SMILES: COc1ccc(-n2ccc(C(F)(F)F)c2COc2ccc(CCCO)c(C)c2C)cc1]

The title compound was prepared by (a) reacting the product prepared in Step B of Example 1 and 4-methoxyphenylboronic acid according to the procedure described in Example 1, Step C, (b) then reacting the resulting product according to the procedure in Example 1, Step D, (c) then reacting the resulting product with ethyl 3-(2,3-dimethyl-4-hydroxyphenyl)propanoate according to the procedure in Example 1, Step E, and Example 2.

¹H NMR (CHLOROFORM-d) δ: 7.34 (d, J=8.6 Hz, 2H), 6.87-7.00 (m, 3H), 6.83 (d, J=2.5 Hz, 1H), 6.57 (d, J=8.1 Hz, 1H), 6.50 (d, J=2.5 Hz, 1H), 4.80 (s, 2H), 3.83 (s, 3H), 3.69 (d, J=4.5 Hz, 2H), 2.61-2.75 (m, 2H), 2.21 (s, 3H), 2.11 (s, 3H), 1.74-1.90 (m, 2H), 1.24-1.35 (m, 1H). Calculated for C24H26F3NO3: 434.2 (M+1); found 434.2.

Example 13

3-(2,3-Difluoro-4-{[1-(4-methoxyphenyl)-3-(trifluoromethyl)-1H-pyrrol-2-yl]methoxy}phenyl)propanoic acid (Compound #26)

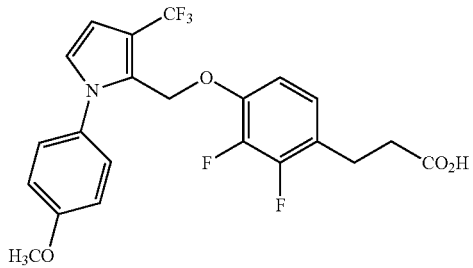 [SMILES: COc1ccc(-n2ccc(C(F)(F)F)c2COc2ccc(CCC(=O)O)c(F)c2F)cc1]

The title compound was prepared by (a) reacting the product prepared in Step B of Example 1 and 4-methoxyphenylboronic acid according to the procedure described in Example 1, Step C, (b) then reacting the resulting product according to the procedure in Example 1, Step D, and (c) then reacting the resulting product with ethyl 3-(2,3-difluoro-4-hydroxyphenyl)propanoate according to the procedure described in Example 1, Steps E and F.

¹H NMR (CHLOROFORM-d) δ: 7.32-7.39 (m, 2H), 6.90-6.97 (m, 2H), 6.79-6.87 (m, 2H), 6.59-6.68 (m, 1H), 6.49 (d, J=3.0 Hz, 1H), 4.89 (s, 2H), 3.83 (s, 3H), 2.93 (t, J=7.6 Hz, 2H), 2.66 (t, J=7.6 Hz, 2H). Calculated for C22H18F5NO4: 456.1 (M+1); found 456.1.

Example 14

3-(2,3-Difluoro-4-{[1-(4-methoxyphenyl)-3-(trifluoromethyl)-1H-pyrrol-2-yl]methoxy}phenyl)propan-1-ol (Compound #27)

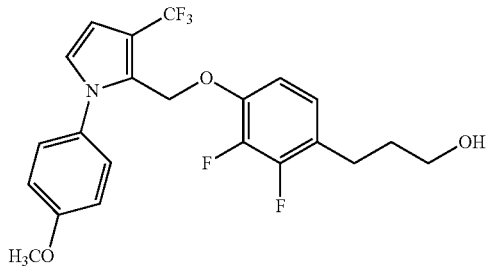 [SMILES: COc1ccc(-n2ccc(C(F)(F)F)c2COc2ccc(CCCO)c(F)c2F)cc1]

The title compound was prepared by (a) reacting the product prepared in Step B of Example 1 and 4-methoxyphenylboronic acid according to the procedure described in Example 1, Step C, (b) then reacting the resulting product according to the procedure in Example 1, Step D, (c) then reacting the resulting product with ethyl 3-(2,3-difluoro-4-hydroxyphenyl)propanoate according to the procedure described in Example 1, Step E, and Example 2.

¹H NMR (CHLOROFORM-d) δ: 7.33-7.40 (m, 2H), 6.90-6.97 (m, 2H), 6.77-6.86 (m, 2H), 6.60-6.67 (m, 1H), 6.49 (d, J=3.0 Hz, 1H), 4.89 (s, 2H), 3.84 (s, 3H), 3.61-3.71 (m, 2H), 2.70 (t, J=7.1 Hz, 2H), 1.79-1.89 (m, 2H), 1.33 (br. s., 1H). Calculated for C22H20F5NO3: 464.1 (M+23); found 464.1.

Example 15

3-(3,5-Difluoro-4-{[1-(4-methoxyphenyl)-3-(trifluoromethyl)-1H-pyrrol-2-yl]methoxy}phenyl)propanoic acid (Compound #)

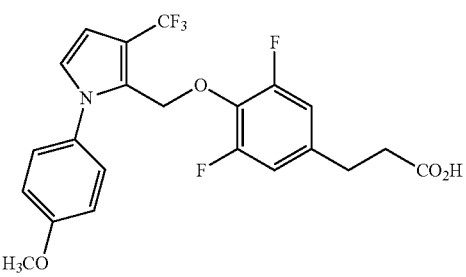 [SMILES: COc1ccc(-n2ccc(C(F)(F)F)c2COc2c(F)cc(CCC(=O)O)cc2F)cc1]

The title compound was prepared by reacting of the product prepared in Step B of Example 1 and 4-methoxyphenylboronic acid according to the procedure described in Example 1, Step C, then reacting the resulting product according to the procedures in Example 1, Steps D through F.

¹H NMR (CHLOROFORM-d) δ: 7.33-7.49 (m, J=8.1 Hz, 2H), 6.87-7.01 (m, J=8.1 Hz, 2H), 6.83 (br. s., 1H), 6.51-6.72 (m, 2H), 6.43 (br. s., 1H), 4.91 (br. s., 2H), 3.72-3.89 (m, 3H), 2.46-2.90 (m, 4H). Calculated for C22H18F5NO4: 478.1 (M+23); found 478.0.

Example 16

3-(4-{[1-(4-Chlorophenyl)-3-(trifluoromethyl)-1H-pyrrol-2-yl]methoxy}-2,3-dimethylphenyl)propanoic acid (Compound #15)

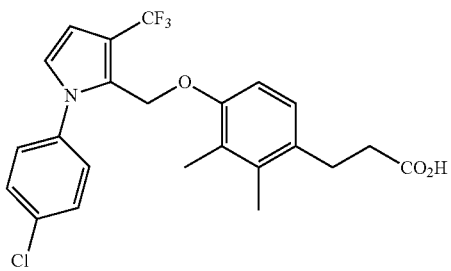 [SMILES: Cc1c(CCC(=O)O)ccc(OCc2c(C(F)(F)F)ccn2-c2ccc(Cl)cc2)c1C]

The title compound was prepared by reacting the product in Example 1, Step D with ethyl 3-(2,3-dimethyl-4-hydroxyphenyl)propanoate according to the procedures described in Example 1, Steps E and F.

¹H NMR (CHLOROFORM-d) δ: 7.34-7.44 (m, 4H), 6.93 (d, J=8.1 Hz, 1H), 6.86 (d, J=2.5 Hz, 1H), 6.59 (d, J=8.6 Hz, 1H), 6.54 (d, J=3.0 Hz, 1H), 4.82 (s, 2H), 2.87-2.98 (m, 2H), 2.54-2.65 (m, 2H), 2.21 (s, 3H), 2.09 (s, 3H). Calculated for C23H21ClF3NO3: 452.1 (M+1); found 452.1.

Example 17

3-(4-{[1-(4-Chlorophenyl)-3-(trifluoromethyl)-1H-pyrrol-2-yl]methoxy}-2,3-dimethylphenyl)propan-1-ol (Compound #17)

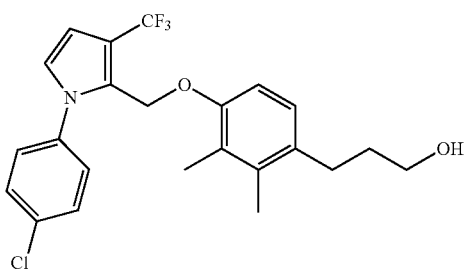

The title compound was prepared by reacting the product in Example 1, Step D with ethyl 3-(2,3-dimethyl-4-hydroxyphenyl)propanoate according to the procedures described in Example 1, Step E, and Example 2.

$^1$H NMR (CHLOROFORM-d) δ: 7.35-7.44 (m, 4H), 6.92 (d, J=8.1 Hz, 1H), 6.86 (d, J=2.5 Hz, 1H), 6.58 (d, J=8.1 Hz, 1H), 6.54 (d, J=2.5 Hz, 1H), 4.82 (s, 2H), 3.69 (t, J=6.3 Hz, 2H), 2.61-2.71 (m, 2H), 2.21 (s, 3H), 2.09 (s, 3H), 1.75-1.86 (m, 2H), 1.34 (br. s., 1H). Calculated for C23H23ClF3NO2: 460.1 (M+23); found 460.2.

Example 18

3-(4-{[1-(4-Chlorophenyl)-1H-pyrrol-2-yl]methoxy}-2,3-dimethylphenyl)propanoic acid (Compound #1)

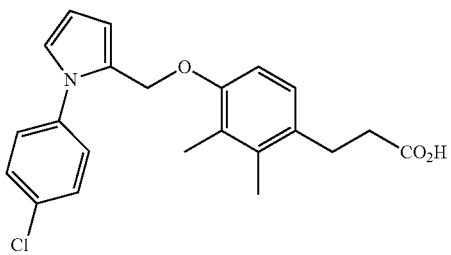 [SMILES: Cc1c(CCC(=O)O)ccc(OCc2cccn2-c2ccc(Cl)cc2)c1C]

The title compound was prepared by reacting methyl 1H-pyrrole-2-carboxylate (commercially available) according to the procedures of Example 1, Steps C and D, then reaction the resulting product with ethyl 3-(2,3-dimethyl-4-hydroxyphenyl)propanoate according to the procedures described in Example 1, Steps E and F.

$^1$H NMR (CHLOROFORM-d) δ: 7.32-7.45 (m, 4H), 6.94 (d, J=8.3 Hz, 1H), 6.89 (br. s., 1H), 6.66 (d, J=8.6 Hz, 1H), 6.44 (br. s., 1H), 6.26-6.34 (m, 1H), 4.81 (s, 2H), 2.93 (t, J=7.8 Hz, 2H), 2.53-2.66 (m, 2H), 2.21 (s, 3H), 2.09 (s, 3H). Calculated for C22H22ClNO3: 384.1 (M+1); found 384.1

Example 19

3-(4-{[1-(4-Bromophenyl)-1H-pyrrol-2-yl]methoxy}-2,3-dimethylphenyl)propanoic acid (Compound #3)

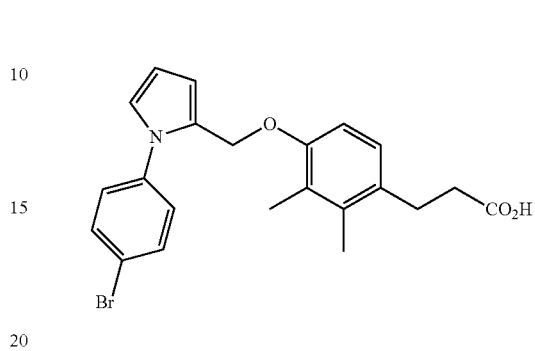

The title compound was prepared by reacting methyl 1H-pyrrole-2-carboxylate with 4-bromophenylboronic acid according to the procedures of Example 1, Steps C and D, then reacting the resulting product with ethyl 3-(2,3-dimethyl-4-hydroxyphenyl)propanoate according to the procedures described in Example 1, Steps E and F.

$^1$H NMR (CHLOROFORM-d) δ: 7.30-7.75 (m, 4H), 6.83-7.07 (m, 2H), 6.66 (d, J=8.1 Hz, 1H), 6.44 (br. s., 1H), 6.30 (d, J=3.0 Hz, 1H), 4.77-4.99 (m, 2H), 2.86-3.19 (m, 2H), 2.52-2.79 (m, 2H), 2.21 (s, 3H), 2.08 (s, 3H). Calculated for C22H22BrNO3: 428.1 (M+1); found 428.1

Example 20

3-(4-{[3-Bromo-1-(4-chlorophenyl)-1H-pyrrol-2-yl]methoxy}-2,3-difluorophenyl)propan-1-ol (Compound #5)

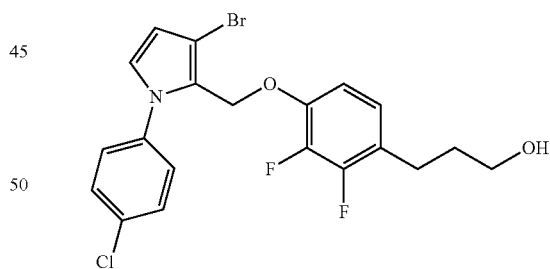

The title compound was prepared by reacting methyl 3-bromo-1-(phenylsulfonyl)-1H-pyrrole-2-carboxylate according to the procedures of Example 1, Steps B to D, then reacting the resulting product with ethyl 3-(2,3-difluoro-4-hydroxyphenyl)propanoate according to the procedure described in Example 1, Step E, and Example 2.

$^1$H NMR (CHLOROFORM-d) δ: 7.41 (s, 4H), 6.81-6.89 (m, 2H), 6.70-6.79 (m, 1H), 6.35 (d, J=3.0 Hz, 1H), 4.88 (s, 2H), 3.68 (br. s., 2H), 2.72 (t, J=7.6 Hz, 2H), 1.80-1.92 (m, 2H), 1.27-1.36 (m, 1H). Calculated for C20H17BrClF2NO2: 456.0 (M+1); found 456.0.

Example 21

3-(4-{[3-Bromo-1-(4-chlorophenyl)-1H-pyrrol-2-yl]methoxy}-2,3-difluorophenyl)propanoic acid (Compound #6)

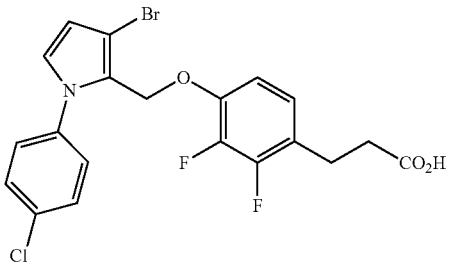 [SMILES: O=C(O)CCc1ccc(OCc2c(Br)ccn2-c2ccc(Cl)cc2)c(F)c1F]

The title compound was prepared by reacting methyl 3-bromo-1-(phenylsulfonyl)-1H-pyrrole-2-carboxylate according to the procedures of Example 1, Steps B to D, then reacting the resulting product with ethyl 3-(2,3-difluoro-4-hydroxyphenyl)propanoate according to the procedure described in Example 1, Steps E and F.

$^1$H NMR (CHLOROFORM-d) δ: 7.40 (s, 4H), 6.83-6.94 (m, 2H), 6.70-6.81 (m, 1H), 6.35 (d, J=3.0 Hz, 1H), 4.88 (s, 2H), 2.95 (t, J=7.6 Hz, 2H), 2.61-2.76 (m, 2H). Calculated for $C_{20}H_{15}BrClF_2NO_3$: 470.0 (M+1); found 470.0.

Example 22

3-(4-{[3-Bromo-1-(4-chlorophenyl)-1H-pyrrol-2-yl]methoxy}-2,3-dimethylphenyl)propan-1-ol (Compound #13)

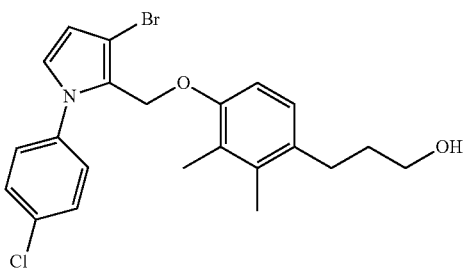 [SMILES: Cc1c(CCCO)ccc(OCc2c(Br)ccn2-c2ccc(Cl)cc2)c1C]

The title compound was prepared by reacting methyl 3-bromo-1-(phenylsulfonyl)-1H-pyrrole-2-carboxylate according to the procedures of Example 1, Steps B to D, then reacting the resulting product with ethyl 3-(2,3-dimethyl-4-hydroxyphenyl)propanoate according to the procedure described in Example 1, Step E, and Example 2.

$^1$H NMR (CHLOROFORM-d) δ: 7.35-7.50 (m, 4H), 6.94 (d, J=8.1 Hz, 1H), 6.84 (d, J=3.0 Hz, 1H), 6.69 (d, J=8.1 Hz, 1H), 6.36 (d, J=3.0 Hz, 1H), 4.80 (s, 2H), 3.65-3.79 (m, 2H), 2.63-2.77 (m, 2H), 2.21 (s, 3H), 2.10 (s, 3H), 1.75-1.89 (m, 2H). Calculated for $C_{22}H_{23}BrClNO_2$: 448.1 (M+1); found 448.1.

Example 23

3-(4-{[3-Bromo-1-(4-chlorophenyl)-1H-pyrrol-2-yl]methoxy}-2,3-dimethylphenyl)propanoic acid (Compound #14)

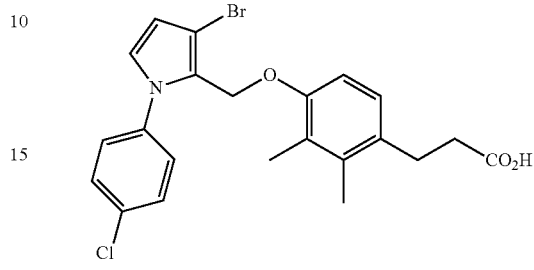

The title compound was prepared by reacting methyl 3-bromo-1-(phenylsulfonyl)-1H-pyrrole-2-carboxylate according to the procedures of Example 1, Steps B through D, then reacting the resulting product with ethyl 3-(2,3-dimethyl-4-hydroxyphenyl)propanoate according to the procedures described in Example 1, Steps E and F.

$^1$H NMR (CHLOROFORM-d) δ: 7.37 (s, 4H), 6.95 (d, J=8.1 Hz, 1H), 6.84 (d, J=3.0 Hz, 1H), 6.69 (d, J=8.1 Hz, 1H), 6.36 (d, J=3.0 Hz, 1H), 4.80 (s, 2H), 2.88-2.98 (m, 2H), 2.53-2.64 (m, 2H), 2.22 (s, 3H), 2.10 (s, 3H). Calculated for $C_{22}H_{21}BrClNO_3$: 462.0 (M+1); found 462.1.

Example 24

3-(4-{[3-Chloro-1-(4-chlorophenyl)-1H-pyrrol-2-yl]methoxy}-2,3-dimethylphenyl)propan-1-ol (Compound #7)

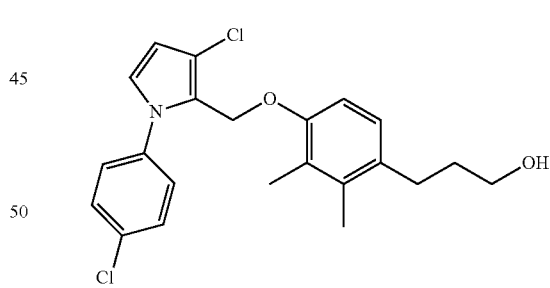

The title compound was prepared by reacting methyl 3-chloro-1H-pyrrole-2-carboxylate (commercially available) according to the procedures of Example 1, Steps C and D, then reacting the resulting product with ethyl 3-(2,3-dimethyl-4-hydroxyphenyl)propanoate according to the procedure described in Example 1, Step E, and Example 2.

$^1$H NMR (CHLOROFORM-d) δ: 7.34-7.42 (m, 4H), 6.94 (d, J=8.1 Hz, 1H), 6.81 (d, J=3.0 Hz, 1H), 6.70 (d, J=8.1 Hz, 1H), 6.30 (d, J=3.0 Hz, 1H), 4.81 (s, 2H), 3.70 (q, J=6.1 Hz, 2H), 2.63-2.72 (m, 2H), 2.21 (s, 3H), 2.10 (s, 3H), 1.75-1.86 (m, 2H), 1.27 (d, J=5.1 Hz, 1H). Calculated for $C_{22}H_{23}Cl_2NO_2$: 426.1 (M+23); found 426.1.

Example 25

3-(4-{[3-Chloro-1-(4-chlorophenyl)-1H-pyrrol-2-yl]methoxy}-2,3-dimethylphenyl)propanoic acid (Compound #8)

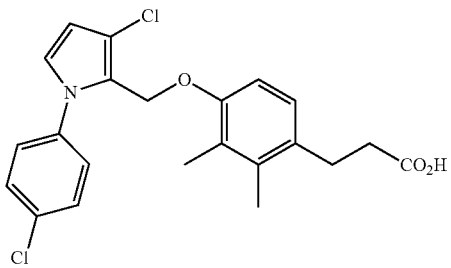 [SMILES: Cc1c(CCC(=O)O)ccc(OCc2c(Cl)ccn2-c2ccc(Cl)cc2)c1C]

The title compound was prepared by reacting methyl 3-chloro-1H-pyrrole-2-carboxylate according to the procedures of Example 1, Steps C and D, then reacting the resulting product with ethyl 3-(2,3-dimethyl-4-hydroxyphenyl)propanoate according to the procedures described in Example 1, Steps E and F.

$^1$H NMR (CHLOROFORM-d) δ: 7.38 (s, 4H), 6.95 (d, J=8.6 Hz, 1H), 6.81 (d, J=3.0 Hz, 1H), 6.70 (d, J=8.6 Hz, 1H), 6.30 (d, J=3.0 Hz, 1H), 4.81 (s, 2H), 2.93 (t, J=7.8 Hz, 2H), 2.54-2.65 (m, 2H), 2.22 (s, 3H), 2.10 (s, 3H). Calculated for $C_{22}H_{21}Cl_2NO_3$: 418.1 (M+1); found 418.1.

Example 26

3-(4-{[3-Chloro-1-(4-chlorophenyl)-1H-pyrrol-2-yl]methoxy}-2,3-difluorophenyl)propan-1-ol (Compound #10)

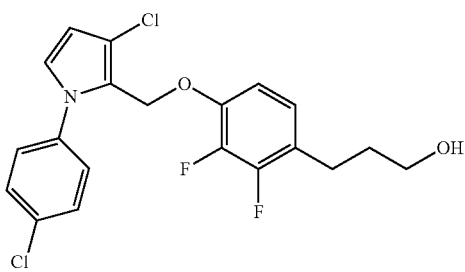 [SMILES: OCCCc1ccc(OCc2c(Cl)ccn2-c2ccc(Cl)cc2)c(F)c1F]

The title compound was prepared by reacting methyl 3-chloro-1H-pyrrole-2-carboxylate according to the procedures of Example 1, Steps C and D, then reacting the resulting product with ethyl 3-(2,3-difluoro-4-hydroxyphenyl)propanoate according to the procedure described in Example 1, Step E, and Example 2.

$^1$H NMR (CHLOROFORM-d) δ: 7.37-7.46 (m, 4H), 6.80-6.89 (m, 2H), 6.71-6.78 (m, 1H), 6.28 (d, J=3.0 Hz, 1H), 4.89 (s, 2H), 3.67 (t, J=6.3 Hz, 2H), 2.71 (t, J=7.6 Hz, 2H), 1.80-1.92 (m, 2H), 1.35-1.46 (m, 1H). Calculated for $C_{20}H_{17}Cl_2F_2NO_2$: 412.1 (M+1); found 412.1.

Example 27

3-(4-{[3-chloro-1-(4-chlorophenyl)-1H-pyrrol-2-yl]methoxy}-2,3-difluorophenyl)propanoic acid (Compound #11)

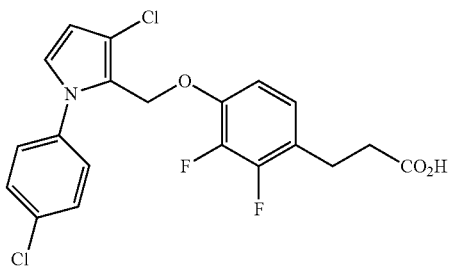 [SMILES: O=C(O)CCc1ccc(OCc2c(Cl)ccn2-c2ccc(Cl)cc2)c(F)c1F]

The title compound was prepared by reacting methyl 3-chloro-1H-pyrrole-2-carboxylate according to the procedures of Example 1, Steps C and D, then reacting the resulting product with ethyl 3-(2,3-difluoro-4-hydroxyphenyl)propanoate according to the procedure described in Example 1, Steps E and F.

$^1$H NMR (CHLOROFORM-d) δ: 7.41 (s, 4H), 6.84-6.93 (m, 1H), 6.82 (d, J=3.0 Hz, 1H), 6.68-6.79 (m, 1H), 6.28 (d, J=3.0 Hz, 1H), 4.89 (s, 2H), 2.95 (t, J=7.6 Hz, 2H), 2.62-2.75 (m, 2H). Calculated for $C_{20}H_{15}Cl_2F_2NO_3$: 426.0 (M+1); found 426.0

Example 28

3-(4-{[1-(4-Chlorophenyl)-3-cyano-1H-pyrrol-2-yl]methoxy}-2,3-difluorophenyl)propanoic acid (Compound #9)

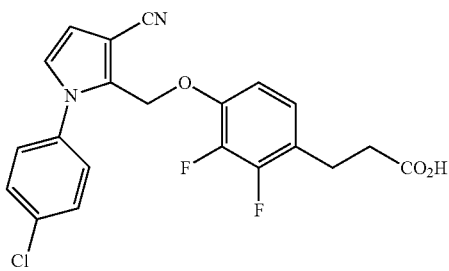 [SMILES: N#Cc1ccn(-c2ccc(Cl)cc2)c1COc1ccc(CCC(=O)O)c(F)c1F]

Step A: ethyl 3-(4-((1-(4-chlorophenyl)-3-cyano-1H-pyrrol-2-yl)methoxy)-2,3-difluorophenyl)propanoate

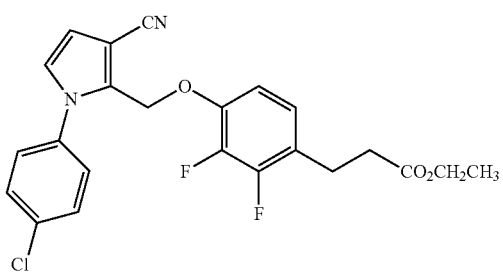

A solution of ethyl 3-(4-((3-bromo-1-(4-chlorophenyl)-1H-pyrrol-2-yl)methoxy)-2,3-difluorophenyl)propanoate (90 mg, 0.18 mmol, 1 eq), zinc cyanide (64 mg, 0.54 mmol, 3 eq), 1,1'-bis(diphenylphosphino)ferrocene (10 mg, 0.018 mmol, 0.1 eq), Pd$_2$(dba)$_3$ (16.5 mg, 0.018 mmol, 0.1 eq) in DMF (1.4 mL) under N$_2$ was heated at 130° C. overnight in a vial. To the resulting mixture was added water, the aqueous was extracted with DCM, dried over MgSO$_4$ and concentrated. The resulting residue was purified by flash chromatography (12 g column) eluting with 10 to 30% EtOAc/heptane to yield ethyl 3-(4-((1-(4-chlorophenyl)-3-cyano-1H-pyrrol-2-yl)methoxy)-2,3-difluorophenyl)propanoate.

Calculated for C23H19ClF2N2O3: 445.1 (M+1); found 445.2.

Step B: 3-(4-{[1-(4-Chlorophenyl)-3-cyano-1H-pyrrol-2-yl]methoxy}-2,3-difluorophenyl)propanoic acid

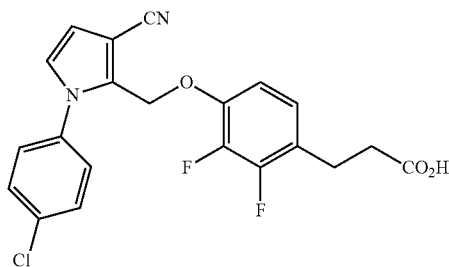 [SMILES: N#Cc1ccn(-c2ccc(Cl)cc2)c1COc1ccc(CCC(=O)O)c(F)c1F]

The title compound was prepared by reacting the product of Example 28, Step A according to the procedure of Example 1, Step F.

$^1$H NMR (CHLOROFORM-d) δ: 7.40-7.51 (m, 4H), 6.86-6.96 (m, 2H), 6.75 (s, 1H), 6.57 (d, J=3.0 Hz, 1H), 4.96 (s, 2H), 2.95 (t, J=7.6 Hz, 2H), 2.68 (d, J=7.6 Hz, 2H). Calculated for C21H15ClF2N2O3: 417.1 (M+1); found 417.1.

Example 29

3-(4-{[1-(4-Chlorophenyl)-3-cyano-1H-pyrrol-2-yl]methoxy}-2,3-dimethylphenyl)propanoic acid (Compound #12)

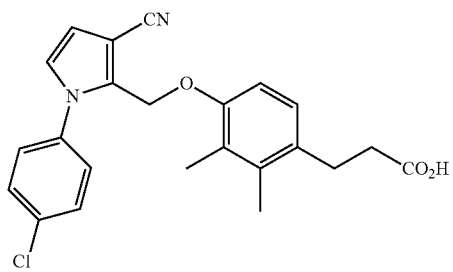 [SMILES: Cc1c(CCC(=O)O)ccc(OCc2c(C#N)ccn2-c2ccc(Cl)cc2)c1C]

The title compound was prepared by reacting ethyl 3-(4-((3-bromo-1-(4-chlorophenyl)-1H-pyrrol-2-yl)methoxy)-2,3-dimethylphenyl)propanoate according to the procedure in Example 28, Step A, and then reacting the resulting product according to the procedure of Example 1, Step F.

$^1$H NMR (CHLOROFORM-d) δ: 7.35-7.47 (m, 4H), 6.95 (d, J=8.1 Hz, 1H), 6.85 (d, J=3.5 Hz, 1H), 6.65 (d, J=8.6 Hz, 1H), 6.58 (d, J=3.0 Hz, 1H), 4.90 (s, 2H), 2.89-2.97 (m, 2H), 2.57-2.63 (m, 2H), 2.21 (s, 3H), 2.06 (s, 3H). Calculated for C23H21ClN2O3: 409.1 (M+1); found 409.1.

Example 30

3-(4-{[1-(4-Ethylphenyl)-1H-pyrrol-2-yl]methoxy}-2,3-dimethylphenyl)propanoic acid (Compound #2)

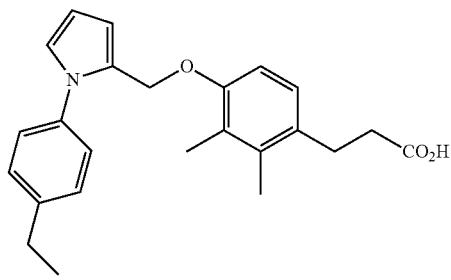 [SMILES: CCc1ccc(-n2cccc2COc2ccc(CCC(=O)O)c(C)c2C)cc1]

The title compound was prepared by reacting methyl 1H-pyrrole-2-carboxylate with 4-ethylphenylboronic acid according to the procedures of Example 1, Steps C and D, then reacting the resulting product with ethyl 3-(2,3-dimethyl-4-hydroxyphenyl)propanoate according to the procedures described in Example 1, Steps E and F.

$^1$H NMR (CHLOROFORM-d) δ: 7.36 (d, J=7.8 Hz, 2H), 7.21 (d, J=7.8 Hz, 2H), 6.92 (d, J=9.5 Hz, 2H), 6.66 (d, J=8.6 Hz, 1H), 6.42 (br. s., 1H), 6.28 (br. s., 1H), 4.82 (s, 2H), 2.92 (t, J=7.9 Hz, 2H), 2.67 (q, J=7.5 Hz, 2H), 2.52-2.63 (m, 2H), 2.20 (s, 3H), 2.09 (s, 3H), 1.18-1.35 (m, 3H). Calculated for C24H27NO3: 400.2 (M+23); found 400.4.

Example 31

3-(4-{[1-(4-Chlorophenyl)-1H-pyrrol-2-yl]methoxy}-2,3-difluorophenyl)propanoic acid (Compound #4)

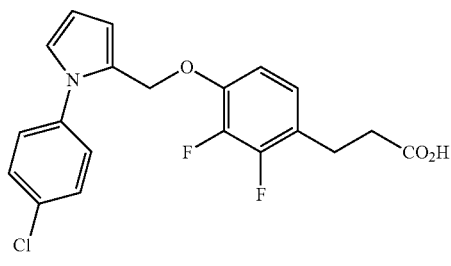 [SMILES: O=C(O)CCc1ccc(OCc2cccn2-c2ccc(Cl)cc2)c(F)c1F]

The title compound was prepared by reacting methyl 1H-pyrrole-2-carboxylate according to the procedures of Example 1, Steps C and D, then reacting the resulting product with ethyl 3-(2,3-difluoro-4-hydroxyphenyl)propanoate according to the procedures described in Example 1, Steps E and F.

$^1$H NMR (CHLOROFORM-d) δ: 7.36-7.45 (m, 4H), 6.89 (d, J=3.0 Hz, 1H), 6.81-6.88 (m, 1H), 6.62-6.70 (m, 1H), 6.42-6.46 (m, 1H), 6.25-6.30 (m, 1H), 4.88 (s, 2H), 2.94 (t,

J=7.8 Hz, 2H), 2.67 (t, J=7.6 Hz, 2H). Calculated for C20H16ClF2NO3: 392.1 (M+1); found 392.2.

Example 32

3-(3,5-difluoro-4-((1-phenyl-3-(trifluoromethyl)-1H-pyrrol-2-yl)methoxy)phenyl)propanoic acid (Compound #38)

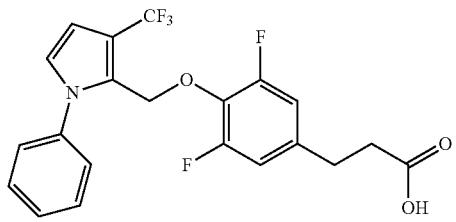 [SMILES: O=C(O)CCc1cc(F)c(OCc2c(C(F)(F)F)ccn2-c2ccccc2)c(F)c1]

Step A: Methyl 1-phenyl-3-(trifluoromethyl)-1H-pyrrole-2-carboxylate

Into a 100-mL round-bottom flask purged and maintained with an inert atmosphere of nitrogen, was placed methyl 3-(trifluoromethyl)-1H-pyrrole-2-carboxylate (810 mg, 4.19 mmol, 1.00 equiv), phenylboronic acid (1.54 g, 12.63 mmol, 3.01 equiv), Cu(OAc)$_2$ (1.52 g, 8.37 mmol, 2.00 equiv), pyridine (1.327 g, 16.78 mmol, 4.00 equiv), 4 Å Molecular Sieves (1.2 g) and dichloromethane (20.0 mL). The resulting solution was stirred for 2 days at 20° C. The reaction progress was monitored by LCMS. The solids were filtered out and the resulting mixture was concentrated under vacuum. The resulting residue was applied onto a silica gel column with ethyl acetate/petroleum ether (1:9) to yield methyl 1-phenyl-3-(trifluoromethyl)-1H-pyrrole-2-carboxylate as a pink solid (0.67 g, 59%)

Step B: [1-phenyl-3-(trifluoromethyl)-1H-pyrrol-2-yl]methanol

Into a 25-mL round-bottom flask purged and maintained with an inert atmosphere of nitrogen, was placed methyl 1-phenyl-3-(trifluoromethyl)-1H-pyrrole-2-carboxylate (460 mg, 1.71 mmol, 1.00 equiv) and tetrahydrofuran (4 mL). To the resulting mixture was then added a solution of LAH (135 mg, 3.56 mmol, 2.00 equiv) in tetrahydrofuran (1 mL) dropwise with stirring at 0° C. The resulting solution was stirred for 60 min at 0° C. in a water/ice bath. The reaction was then quenched by the addition of water (10 mL). The resulting solution was extracted with ethyl acetate (5×10 mL) and the organic layers combined. The resulting residue was applied onto a silica gel column with ethyl acetate/petroleum ether (1:4) to yield [1-phenyl-3-(trifluoromethyl)-1H-pyrrol-2-yl]methanol as light yellow oil (280 mg, 66%).

Step C: Ethyl 3-(3,5-difluoro-4-[[1-phenyl-3-(trifluoromethyl)-1H-pyrrol-2-yl]methoxy]phenyl)propanoate Into a 50-mL round-bottom flask purged and maintained with an inert atmosphere of nitrogen, was placed [1-phenyl-3-(trifluoromethyl)-1H-pyrrol-2-yl]methanol (260 mg, 1.05 mmol, 1.00 equiv, 97%), ethyl 3-(3,5-difluoro-4-hydroxyphenyl)propanoate (281 mg, 1.22 mmol, 1.20 equiv), ADDP (642 mg, 2.56 mmol, 2.50 equiv), Bu$_3$P (309 mg, 1.53 mmol, 1.50 equiv) and toluene (5 mL). The resulting solution was stirred overnight at 60° C. in an oil bath. The resulting mixture was then concentrated under vacuum. The resulting mixture was washed with diethyl ether (50 mL). The resulting residue was applied onto a silica gel column with ethyl acetate/petroleum ether (1:5) to yield ethyl 3-(3,5-difluoro-4-[[1-phenyl-3-(trifluoromethyl)-1H-pyrrol-2-yl]methoxy]phenyl)propanoate as yellow oil (220 mg, 45%).

Step D: 3-(3,5-difluoro-4-[[1-phenyl-3-(trifluoromethyl)-1H-pyrrol-2-yl]methoxy]phenyl)propanoic acid Into a 25-mL round-bottom flask, was placed ethyl 3-(3,5-difluoro-4-[[1-phenyl-3-(trifluoromethyl)-1H-pyrrol-2-yl]methoxy]phenyl)propanoate (100 mg, 0.22 mmol, 1.00 equiv), tetrahydrofuran (1 mL) and a solution of LiOH (100 mg, 4.18 mmol, 18.93 equiv) in water (1 mL). The resulting solution was stirred overnight at 25° C. in an oil bath. The reaction progress was monitored by LCMS. The resulting mixture was then concentrated under vacuum. The pH value of the solution was adjusted to pH5 with hydrogen chloride (2 mol/L). The resulting solution was extracted with ethyl acetate (3×5 mL) and the organic layers combined. The resulting residue was purified by Flash-Prep-HPLC with the following conditions (IntelFlash-1): Column, silica gel; mobile phase, ACN/H$_2$O (0.05% CF$_3$COOH)=1:1 increasing to ACN/H$_2$O (0.05% CF$_3$COOH)=9:1 within 10 min; Detector, UV 254 nm to yield 3-(3,5-difluoro-4-[[1-phenyl-3-(trifluoromethyl)-1H-pyrrol-2-yl]methoxy]phenyl)propanoic acid as a white solid (22.5 mg, 23%).

$^1$H NMR (300 MHz, CD$_3$OD) δ: 7.45-7.54 (m, 5H), 7.02 (d, J=3.0 Hz, 1H), 6.83 (d, J=7.2 Hz, 2H), 6.49 (d, J=3.0 Hz, 1H), 4.99 (s, 2H), 2.84 (t, J=8.1 Hz, 2H), 2.46 (t, J=7.5 Hz, 2H). Mass spectrum (ESI, m/z): Calculated for C$_{21}$H$_{16}$F$_5$NO$_3$, 424.1 (M−H), found 424.1

The following representative compounds of formula (I) of the present invention were similarly prepared according to the procedures as described herein.

Example 33

3-(2,3-difluoro-4-[[1-(4-methylphenyl)-3-(trifluoromethyl)-1H-pyrrol-2-yl]methoxy]phenyl) propanoic acid (Compound #42)

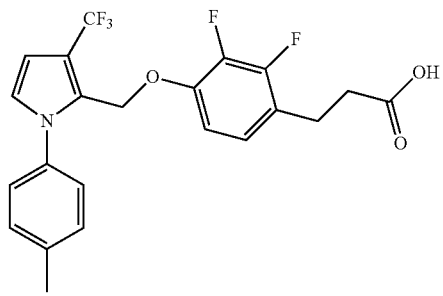 [SMILES: Cc1ccc(-n2ccc(C(F)(F)F)c2COc2ccc(CCC(=O)O)c(F)c2F)cc1]

$^1$H NMR (400 MHz, CD$_3$OD) δ: 7.28-7.33 (m, 4H), 7.20 (s, 1H), 6.93 (t, J=8.8 Hz, 1H), 6.72 (t, J=8.0 Hz, 1H), 6.52 (s, 1H), 4.96 (s, 2H), 2.91 (t, J=7.2 Hz, 2H), 2.58 (t, J=7.2 Hz, 2H), 2.40 (s, 3H). Mass spectrum (ESI, m/z): Calculated for C$_{22}$H$_{18}$F$_5$NO$_3$, 438.1 (M−H), found 438.1.

Example 34

3-(3,5-difluoro-4-[[1-(4-methylphenyl)-3-(trifluoromethyl)-1H-pyrrol-2-yl]methoxy]phenyl)propanoic acid (Compound #39)

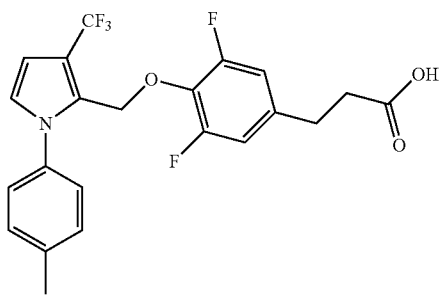 [SMILES: Cc1ccc(-n2ccc(C(F)(F)F)c2COc2c(F)cc(CCC(=O)O)cc2F)cc1]

$^1$H NMR (300 MHz, CD$_3$OD) δ: 7.31-7.39 (m, 4H), 6.82 (d, J=9.3 Hz, 2H), 6.70 (d, J=3.0 Hz, 1H), 6.47 (d, J=3.0 Hz, 1H), 4.99 (s, 2H), 2.86 (t, J=7.5 Hz, 2H), 2.59 (t, J=7.5 Hz, 2H), 2.44 (s, 3H). Mass spectrum (ESI, m/z): Calculated for C$_{22}$H$_{18}$F$_5$NO$_3$, 438.1 (M−H), found 438.1

Example 35

3-(2,3-dimethyl-4-[[1-(4-methylphenyl)-3-(trifluoromethyl)-1H-pyrrol-2-yl]methoxy]phenyl))propanoic acid (Compound #43)

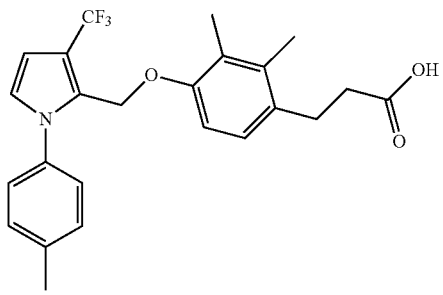 [SMILES: Cc1ccc(-n2ccc(C(F)(F)F)c2COc2ccc(CCC(=O)O)c(C)c2C)cc1]

$^1$H NMR (400 MHz, CD$_3$OD) δ: 7.26-7.32 (m, 4H), 6.70 (s, 1H), 6.90 (d, J=8.8 Hz, 1H), 6.57 (d, J=8.4 Hz, 1H), 6.53 (s, 1H), 4.86 (s, 2H), 2.89 (t, J=8.0 Hz, 2H), 2.50 (t, J=7.6 Hz, 2H), 2.39 (s, 3H), 2.22 (s, 3H), 2.05 (s, 3H). Mass spectrum (ESI, m/z): Calculated for C$_{24}$H$_{24}$F$_3$NO$_3$, 430.2 (M−H), found 430.2.

Example 36

3-(4-[[1-(4-ethylphenyl)-3-(trifluoromethyl)-1H-pyrrol-2-yl]methoxy]-2,3-difluorophenyl) propanoic acid (Compound #34)

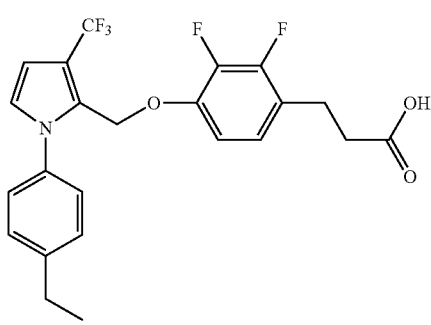

$^1$H NMR (300 MHz, CD$_3$OD) δ: 7.29-7.31 (m, 4H), 7.02 (d, J=2.7 Hz, 1H), 6.89-6.95 (m, 1H), 6.68-6.674 (m, 1H), 6.53 (d, J=2.7 Hz, 1H), 4.97 (s, 2H), 2.91 (t, J=7.5 Hz, 2H), 2.70 (q, J=7.8 Hz, 2H), 2.58 (t, J=7.5 Hz, 2H), 1.25 (t, J=7.8 Hz, 3H). Mass spectrum (ESI, m/z): Calculated for C$_{23}$H$_{20}$F$_5$NO$_3$, 452.1 (M−H), found 452.1.

Example 37

3-(4-[[1-(4-ethylphenyl)-3-(trifluoromethyl)-1H-pyrrol-2-yl]methoxy]-3,5-difluorophenyl)propanoic acid (Compound #32)

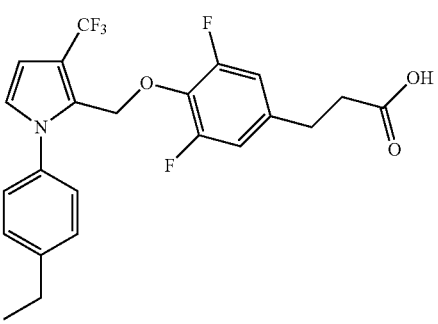 [SMILES: CCc1ccc(-n2ccc(C(F)(F)F)c2COc2c(F)cc(CCC(=O)O)cc2F)cc1]

1H NMR (300 MHz, CD$_3$OD) δ: 7.31-7.36 (m, 4H), 6.95 (d, J=3.3 Hz, 1H), 6.77 (d, J=9.6 Hz, 2H), 6.43 (d, J=3.3 Hz, 1H), 4.95 (s, 2H), 3.81 (t, J=7.5 Hz, 2H), 2.66-2.74 (m, 2H), 2.54 (t, J=7.5 Hz, 2H), 1.25 (t, J=7.8 Hz, 3H). Mass spectrum (ESI, m/z): Calculated for C$_{23}$H$_{20}$F$_5$NO$_3$, 452.1 (M−H), found 452.1

Example 38

3-(4-[[1-(4-ethylphenyl)-3-(trifluoromethyl)-1H-pyrrol-2-yl]methoxy]-2,3-dimethylphenyl) propanoic acid (Compound #36)

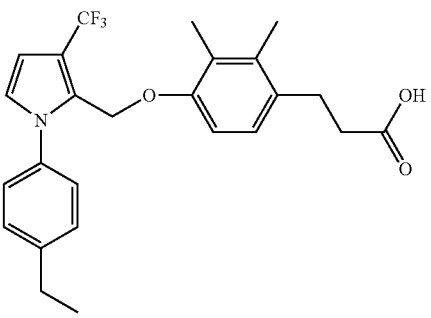 [SMILES: CCc1ccc(-n2ccc(C(F)(F)F)c2COc2ccc(CCC(=O)O)c(C)c2C)cc1]

$^1$H NMR (300 MHz, CD$_3$OD) δ: 7.24-7.63 (m, 4H), 6.95-6.877 (m, 2H), 6.53-6.61 (m, 2H), 4.85 (s, 2H), 2.86-2.97 (m, 2H), 2.58-2.74 (m, 4H), 2.23 (s, 3H), 2.11 (s, 3H), 1.28 (t, J=7.8 Hz, 3H). Mass spectrum (ESI, m/z): Calculated for C$_{25}$H$_{26}$F$_3$NO$_3$, 444.2 (M−H), found 444.2

Example 39

3-(3,5-difluoro-4-[[1-phenyl-3-(trifluoromethyl)-1H-pyrrol-2-yl]methoxy]phenyl)propan-1-ol (Compound #35)

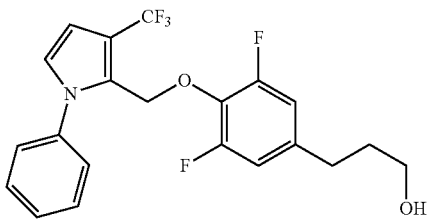 [SMILES: OCCCc1cc(F)c(OCc2c(C(F)(F)F)ccn2-c2ccccc2)c(F)c1]

$^1$H NMR (300 MHz, CD$_3$OD) δ: 7.54 (s, 5H), 7.05 (d, J=3.0 Hz, 1H), 6.81 (t, J=6.3 Hz, 2H), 6.49 (d, J=3.0 Hz, 1H), 5.01 (s, 2H), 3.57 (t, J=6.6 Hz, 2H), 2.64 (t, J=7.8 Hz, 2H), 1.76-1.85 (m, 2H). Mass spectrum (ESI, m/z): Calculated for C$_{21}$H$_{18}$F$_5$NO$_2$, 224.1 (M-C$_9$H$_9$F$_2$O$_2$), found 224.1

Example 40

3-(2,3-difluoro-4-[[1-(4-methylphenyl)-3-(trifluoromethyl)-1H-pyrrol-2-yl]methoxy]phenyl)propan-1-ol (Compound #44)

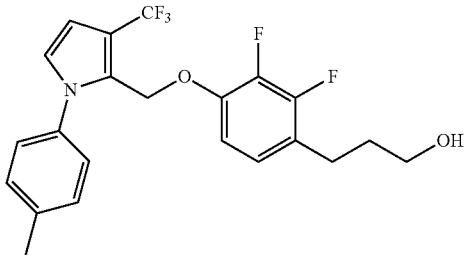 [SMILES: Cc1ccc(-n2ccc(C(F)(F)F)c2COc2ccc(CCCO)c(F)c2F)cc1]

$^1$H NMR (400 MHz, CD$_3$OD) δ: 7.28-7.35 (m, 4H), 7.02 (s, 1H), 6.90 (t, J=8.0 Hz, 1H), 6.74 (t, J=7.2 Hz, 1H), 6.52 (s, 1H), 4.96 (s, 2H), 3.58 (t, J=6.4 Hz, 2H), 2.69 (t, J=7.2 Hz, 2H), 1.79-1.84 (m, 2H). Mass spectrum (ESI, m/z): Calculated for C$_{22}$H$_{20}$F$_5$NO$_2$, 238.1 (M-C$_8$H$_9$F$_3$O$_2$), found 238.1.

Example 41

3-(3,5-difluoro-4-[[1-(4-methylphenyl)-3-(trifluoromethyl)-1H-pyrrol-2-yl]methoxy]phenyl)propan-1-ol (Compound #37)

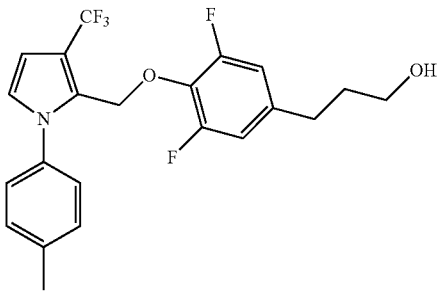 [SMILES: Cc1ccc(-n2ccc(C(F)(F)F)c2COc2c(F)cc(CCCO)cc2F)cc1]

$^1$H NMR (400 MHz, CD$_3$OD) δ: 7.40 (d, J=8.4 Hz, 2H), 7.33 (d, J=8.4 Hz, 2H), 7.00 (d, J=2.8 Hz, 1H), 6.79 (d, J=9.2 Hz, 2H), 6.47 (d, J=3.2 Hz, 1H), 4.99 (s, 2H), 3.56 (t, J=6.4 Hz, 2H), 2.64 (t, J=8.0 Hz, 2H), 2.44 (s, 3H), 1.77-1.84 (m, 2H). Mass spectrum (ESI, m/z): Calculated for C$_{22}$H$_{20}$F$_5$NO$_2$, 238.1 (M-C$_9$H$_9$F$_2$O$_2$), found 238.1.

Example 42

3-(2,3-dimethyl-4-[[1-(4-methylphenyl)-3-(trifluoromethyl)-1H-pyrrol-2-yl]methoxy]phenyl)propan-1-ol (Compound #45)

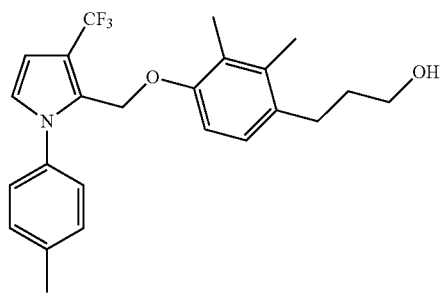 [SMILES: Cc1ccc(-n2ccc(C(F)(F)F)c2COc2ccc(CCCO)c(C)c2C)cc1]

$^1$H NMR (300 MHz, CD$_3$OD) δ: 7.32-7.24 (m, 4H), 6.98 (d, J=3.0 Hz, 1H), 6.87 (d, J=8.4 Hz, 1H), 6.56-6.50 (m, 2H), 4.84 (s, 2H), 3.58 (t, J=6.3 Hz, 2H), 2.64 (t, J=7.1 Hz, 2H), 2.38 (s, 3H), 2.19 (s, 3H), 2.03 (s, 3H), 1.70-1.78 (m, 2H). Mass spectrum (ESI, m/z): Calculated for C$_{24}$H$_{26}$F$_3$NO$_2$, 440.2 (M+Na), found 440.2

Example 43

3-(4-[[1-(4-ethylphenyl)-3-(trifluoromethyl)-1H-pyrrol-2-yl]methoxy]-2,3-difluorophenyl)propan-1-ol (Compound #41)

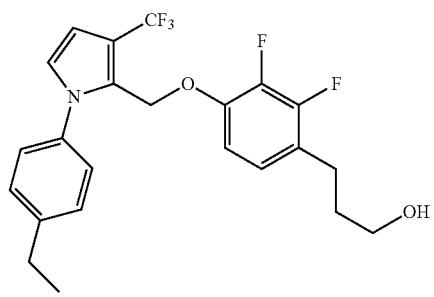 [SMILES: CCc1ccc(-n2ccc(C(F)(F)F)c2COc2ccc(CCCO)c(F)c2F)cc1]

$^1$H NMR (300 MHz, CD$_3$OD) δ: 7.23-7.45 (m, 4H), 7.02-7.09 (m, 1H), 6.87-6.92 (m, 1H), 6.67-6.73 (m, 1H), 6.52-6.59 (m, 1H), 4.97 (s, 2H), 3.66-3.78 (m, 2H), 2.52-2.74 (m, 4H), 1.79-1.89 (m, 2H), 1.25 (t, J=7.5 Hz, 3H). Mass spectrum (ESI, m/z): Calculated for C$_{23}$H$_{22}$F$_5$NO$_2$, 503.2 (M+Na+CH$_3$CN), found 503.2

Example 44

3-(4-[[1-(4-ethylphenyl)-3-(trifluoromethyl)-1H-pyrrol-2-yl]methoxy]-3,5-difluoro-phenyl)propan-1-ol (Compound #33)

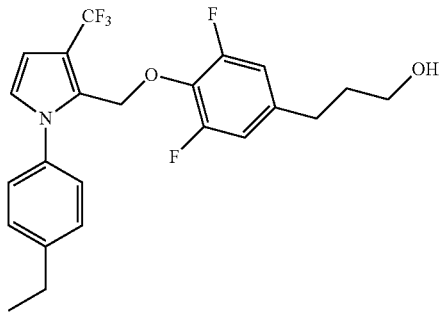 [SMILES: CCc1ccc(-n2ccc(C(F)(F)F)c2COc2c(F)cc(CCCO)cc2F)cc1]

$^1$H NMR (300 MHz, CD$_3$OD) δ: 7.36 (d, J=6.3 Hz, 2H), 7.29 (d, J=6.6 Hz, 2H), 6.95 (s, 1H), 6.72 (d, J=4.8 Hz, 2H), 6.42 (s, 1H), 4.94 (s, 2H), 3.51 (t, J=6.3 Hz, 2H), 2.69 (q, J$_1$=15.3 Hz, J$_2$=7.5 Hz, 2H), 2.59 (t, J=8.1 Hz, 2H), 1.75-1.80 (m, 2H), 1.24 (t, J=7.5 Hz, 3H). Mass spectrum (ESI, m/z): Calculated for C$_{23}$H$_{22}$F$_5$NO$_2$, 503.2 (M+Na+CH$_3$CN), found 503.2

Example 45

3-(4-[[1-(4-ethylphenyl)-3-(trifluoromethyl)-1H-pyrrol-2-yl]methoxy]-2,3-dimethylphenyl)propan-1-ol (Compound #40)

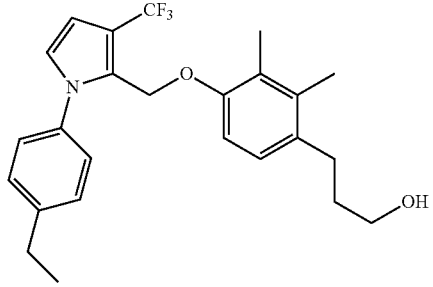 [SMILES: CCc1ccc(-n2ccc(C(F)(F)F)c2COc2ccc(CCCO)c(C)c2C)cc1]

$^1$H NMR (300 MHz, CD$_3$OD) δ: 7.28-7.35 (m, 4H), 6.97-6.99 (m, 1H), 6.85-6.88 (m, 1H), 6.53-6.61 (m, 2H), 4.87 (s, 2H), 4.97 (s, 2H), 3.59 (t, J=6.0 Hz, 2H), 2.62-2.80 (m, 4H), 2.20 (s, 3H), 2.02 (s, 3H), 1.52-1.78 (m, 2H), 1.25 (t, J=7.5 Hz, 3H). Mass spectrum (ESI, m/z): Calculated for C$_{25}$H$_{28}$F$_3$NO$_2$, 432.2 (M+H), found 432.2

Example 46

3-(3,5-difluoro-4-[2-[1-(4-methoxyphenyl)-3-(trifluoromethyl)-1H-pyrrol-2-yl]ethyl]phenyl)propan-1-ol (Compound #31)

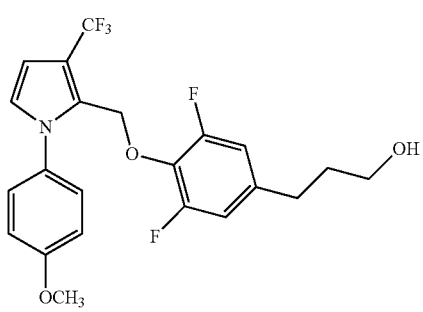 [SMILES: COc1ccc(-n2ccc(C(F)(F)F)c2COc2c(F)cc(CCCO)cc2F)cc1]

$^1$H NMR (300 MHz, CD$_3$Cl) δ: 7.48 (d, J=6.9 Hz, 2H), 7.00 (d, J=6.9 Hz, 2H), 6.87 (d, J=2.7 Hz, 1H), 6.72 (d, J=9.0 Hz, 2H), 6.47 (d, J=3.0 Hz, 1H), 4.97 (s, 2H), 3.89 (s, 3H), 3.67 (t, J=6.3 Hz, 2H), 2.65 (t, J=7.5 Hz, 2H), 1.81-1.90 (m, 2H). Mass spectrum (ESI, m/z): Calculated for C$_{22}$H$_{20}$F$_5$NO$_3$, 254.1 (M-C$_9$H$_9$F$_2$O$_2$), found 254.1

Example 47

3-(4-[[1-(4-bromophenyl)-3-(trifluoromethyl)-1H-pyrrol-2-yl]methoxy]-3,5-difluorophenyl)propan-1-ol (Compound #30)

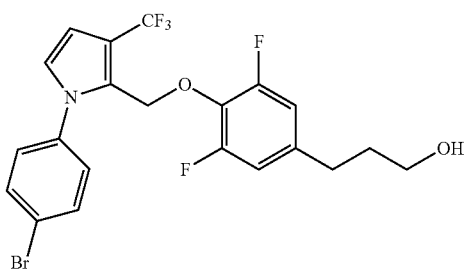

$^1$H NMR (400 MHz, CD$_3$OD) δ: 7.69 (d, J=11.2 Hz, 2H), 7.50 (d, J=11.2 Hz, 2H), 7.06 (d, J=2.8 Hz, 1H), 6.82 (d, J=16.8 Hz, 2H), 6.51 (d, J=2.8 Hz, 1H), 5.02 (s, 2H), 3.56 (t, J=6.4 Hz, 2H), 2.65 (t, J=7.6 Hz, 2H), 1.77-1.84 (m, 2H). Mass spectrum (ESI, m/z): Calculated for C$_{21}$H$_{17}$BrF$_5$NO$_2$, 512.0 (M+Na), found 512.0

Example 48

3-(2,3-difluoro-4-[[1-(6-methylpyridin-3-yl)-3-(trifluoromethyl)-1H-pyrrol-2-yl]methoxy]phenyl)propanoic acid (Compound #53)

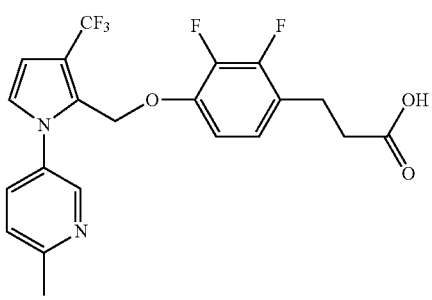 [SMILES: Cc1ccc(-n2ccc(C(F)(F)F)c2COc2ccc(CCC(=O)O)c(F)c2F)cn1]

$^1$H NMR (300 MHz, CD$_3$OD) δ: 8.59 (s, 1H), 7.93 (d, J=8.4 Hz, 1H), 7.48 (d, J=8.4 Hz, 1H), 7.09 (s, 1H), 6.91 (t, J=8.7 Hz, 1H), 6.72 (t, J=9.0 Hz, 1H), 6.56 (s, 1H), 4.98 (s, 2H), 2.86 (t, J=7.5 Hz, 2H), 2.59 (s, 3H), 2.54 (t, J=7.5 Hz, 2H) Mass spectrum (ESI, m/z): Calculated for C$_{21}$H$_{17}$F$_5$N$_2$O$_3$, 439.1 (M−H), found 439.1

Example 49

3-(2,3-difluoro-4-[[1-(6-methylpyridin-3-yl)-3-(trifluoromethyl)-1H-pyrrol-2-yl]methoxy]phenyl)propan-1-ol trifluoroacetic acid (Compound #47)

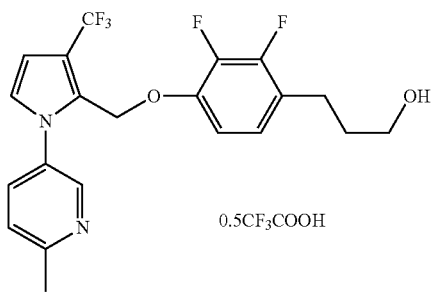 [SMILES: Cc1ccc(-n2ccc(C(F)(F)F)c2COc2ccc(CCCO)c(F)c2F)cn1]

1H NMR (300 MHz, CD3OD) δ: 8.70 (s, 1H), 8.19 (bs, 1H), 7.72 (bs, 1H), 7.18 (s, 1H), 6.96 (t, J=6.0 Hz, 1H), 6.80 (t, J=5.7 Hz, 1H), 6.65 (s, 1H), 5.06 (s, 2H), 3.58 (t, J=5.1 Hz, 2H), 2.72 (s, 3H), 2.68 (t, J=5.4 Hz, 2H), 1.76-1.83 (m, 2H). Mass spectrum (ESI, m/z): Calculated for $C_{21}H_{19}F_5N_2O_2$, 427.1 (M−0.5CF3COOH+H), found 427.1

Example 50

3-(3,5-difluoro-4-[[1-(6-methylpyridin-3-yl)-3-(trifluoromethyl)-1H-pyrrol-2-yl]methoxy]-phenyl)propanoic acid (Compound #49)

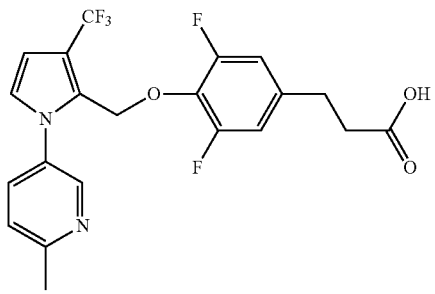

PH-ZHS-XZ2-34-025-0

1H NMR (300 MHz, CD3OD) δ: 8.62 (d, J=2.7 Hz, 1H), 7.97 (dd, J=2.7 Hz, 8.4 Hz, 1H), 7.52 (d, J=8.4 Hz, 1H), 7.10 (s, 1H), 6.84 (d, J=9.6 Hz, 2H), 6.54 (s, 1H), 5.04 (s, 2H), 2.86 (t, J=7.5 Hz, 2H), 2.66 (s, 3H), 2.59 (t, J=7.5 Hz, 2H). Mass spectrum (ESI, m/z): Calculated for $C_{21}H_{17}F_5N_2O_3$, 441.1 (M+H), found 441.1

Example 51

3-(3,5-difluoro-4-((1-(6-methylpyridin-3-yl)-3-(trifluoromethyl)-1H-pyrrol-2-yl)methoxy)phenyl)propan-1-ol trifluoroacetic acid (Compound #48)

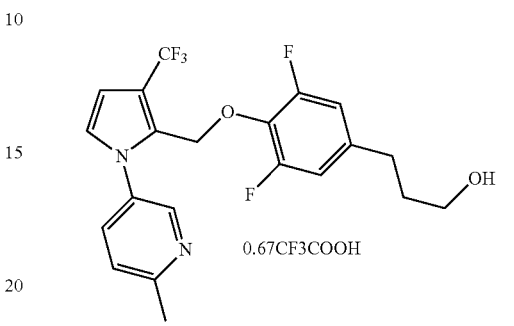

1H NMR (300 MHz, CD3OD) δ: 8.75 (d, J=2.7 Hz, 1H), 8.19 (dd, J=2.7 Hz, 8.4 Hz, 1H), 7.66 (d, J=8.4 Hz, 1H), 7.12 (d, J=3.6 Hz, 1H), 6.74-6.81 (m, 2H), 6.52 (d, J=3.6 Hz, 1H), 5.00 (s, 2H), 3.51 (t, J=6.3 Hz, 2H), 2.69 (s, 3H), 2.60 (t, J=7.8 Hz, 2H), 1.70-1.80 (m, 2H). Mass spectrum (ESI, m/z): Calculated for $C_{22.34}H_{19.67}F_{7.01}N_2O_{3.34}$, 427.1 (M−0.67CF3COOH+H), found 427.1

Example 52

3-(4-[[1-(6-ethylpyridin-3-yl)-3-(trifluoromethyl)-1H-pyrrol-2-yl]methoxy]-2,3-difluorophenyl)propanoic acid (Compound #58)

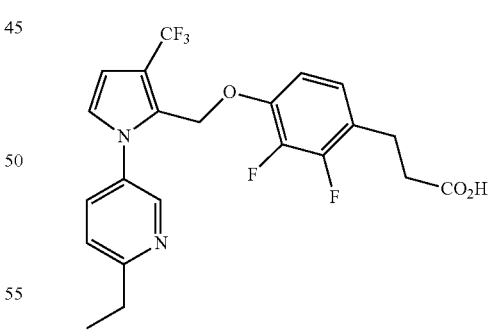

1H NMR (300 MHz, CD3OD) δ: 8.54 (s, 1H), 7.88 (d, J=8.4 Hz, 4H), 7.44 (d, J=8.4 Hz, 1H), 7.08 (d, J=3.3 Hz, 1H), 6.87-6.95 (m, 1H), 6.69-6.75 (m, 1H), 6.55 (d, J=3.3 Hz, 1H), 4.98 (s, 2H), 2.81-3.04 (m, 4H), 2.80 (t, J=8.4 Hz, 2H), 1.27 (t, J=8.4 Hz, 3H). Mass spectrum (ESI, m/z): Calculated for $C_{22}H_{19}F_5N_2O_3$, 453.1 (M−H), found 453.1

Example 53

3-(4-[[1-(6-ethylpyridin-3-yl)-3-(trifluoromethyl)-1H-pyrrol-2-yl]methoxy]-2,3-difluorophenyl)propan-1-ol (Compound #54)

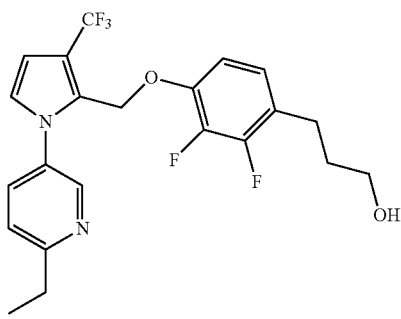 [SMILES: CCc1ccc(-n2ccc(C(F)(F)F)c2COc2ccc(CCCO)c(F)c2F)cn1]

$^1$H NMR (300 MHz, CD$_3$OD) δ: 8.52 (s, 1H), 7.85 (d, J=8.4 Hz, 4H), 7.41 (d, J=8.4 Hz, 1H), 7.07 (d, J=3.3 Hz, 1H), 6.84-6.90 (m, 1H), 6.68-6.74 (m, 1H), 6.55 (d, J=3.0 Hz, 1H), 4.84 (s, 2H), 3.52 (t, J=6.3 Hz, 2H), 2.83 (q, J=15.2 Hz, 7.5 Hz, 2H), 2.64 (t, J=7.2 Hz, 2H), 1.70-1.75 (m, 2H), 1.26 (t, J=7.5 Hz, 3H). Mass spectrum (ESI, m/z): Calculated for C$_{22}$H$_{21}$F$_5$N$_2$O$_2$, 441.1 (M+H), found 441.1

Example 54

3-(4-[[1-(6-ethylpyridin-3-yl)-3-(trifluoromethyl)-1H-pyrrol-2-yl]methoxy]-3,5-difluorophenyl)propanoic acid (Compound #56)

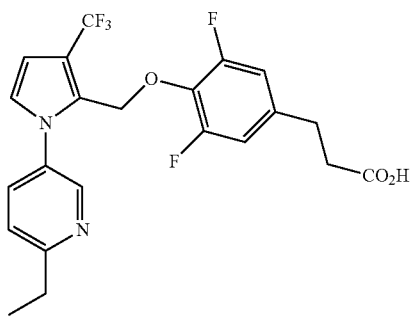 [SMILES: CCc1ccc(-n2ccc(C(F)(F)F)c2COc2c(F)cc(CCC(=O)O)cc2F)cn1]

$^1$H NMR (300 MHz, CD$_3$OD) δ: 8.69 (d, J=2.4 Hz, 1H), 8.10 (d, J=8.4 Hz, 4H), 7.61 (d, J=8.4 Hz, 1H), 7.10 (d, J=3.0 Hz, 1H), 6.80 (d, J=9.3 Hz, 2H), 6.52 (d, J=3.0 Hz, 1H), 5.00 (s, 2H), 2.95 (q, J$_1$=15.2 Hz, J$_2$=7.5 Hz, 2H), 2.81 (t, J=7.5 Hz, 2H), 2.54 (t, J=7.5 Hz, 2H), 1.35 (t, J=7.5 Hz, 3H). Mass spectrum (ESI, m/z): Calculated for C$_{22}$H$_{19}$F$_5$N$_2$O$_3$, 453.1 (M−H), found 453.1

Example 55

3-(4-[[1-(6-ethylpyridin-3-yl)-3-(trifluoromethyl)-1H-pyrrol-2-yl]methoxy]-3,5-difluorophenyl)propan-1-ol (Compound #55)

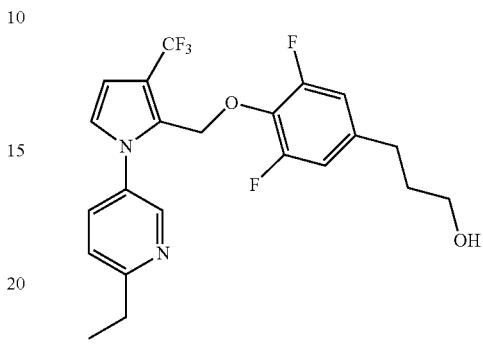

$^1$H NMR (300 MHz, CD$_3$OD) δ: 8.58 (d, J=2.4 Hz, 1H), 7.93 (dd, J$_1$=8.4 Hz, J$_2$=2.7 Hz, 4H), 7.45 (d, J=8.4 Hz, 1H), 7.06 (d, J=3.0 Hz, 1H), 6.75 (d, J=9.3 Hz, 2H), 6.47 (d, J=3.0 Hz, 1H), 5.03 (s, 2H), 3.49 (t, J=6.3 Hz, 2H), 2.88 (q, J=15.2, 7.5 Hz, 2H), 2.59 (t, J=7.2 Hz, 2H), 1.70-1.80 (m, 2H), 1.47 (t, J=7.5 Hz, 3H). Mass spectrum (ESI, m/z): Calculated for C$_{22}$H$_{21}$F$_5$N$_2$O$_2$, 441.2 (M+H), found 441.2

Example 56

3-(2,3-difluoro-4-((1-(6-methoxypyridin-3-yl)-3-(trifluoromethyl)-1H-pyrrol-2-yl)methoxy)phenyl) propanoic acid trifluoroacetic acid (Compound #57)

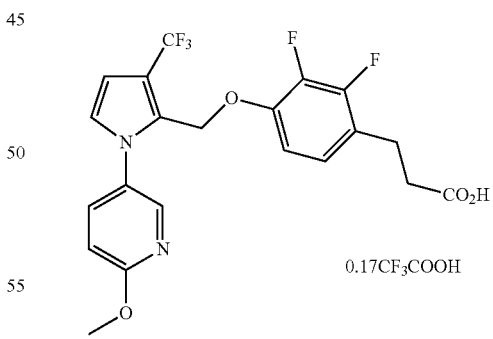

0.17CF$_3$COOH $^1$H NMR (300 MHz, CD$_3$OD) δ: 8.17 (s, 1H), 7.69-7.73 (m, 1H), 7.00 (s, 1H), 6.90-6.93 (m, 2H), 6.68-6.74 (m, 1H), 6.50 (s, 1H), 4.93 (s, 2H), 3.90 (s, 2H), 2.86 (t, J=7.8 Hz, 2H), 2.54 (t, J=7.8 Hz, 2H). Mass spectrum (ESI, m/z): Calculated for C$_{21.34}$H$_{17.17}$F$_{5.51}$N$_2$O$_{4.34}$, 455.1 (M−0.17CF$_3$COOH−H), found 455.1

Example 57

3-(2,3-difluoro-4-[[1-(6-methoxypyridin-3-yl)-3-(trifluoromethyl)-1H-pyrrol-2-yl]methoxy]phenyl) propan-1-ol (Compound #50)

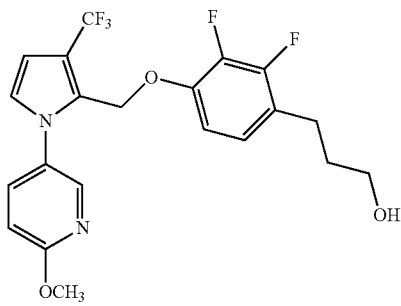 [SMILES: COc1ccc(-n2ccc(C(F)(F)F)c2COc2ccc(CCCO)c(F)c2F)cn1]

$^1$H NMR (300 MHz, CD$_3$OD) δ: 8.18 (s, 1H), 7.70-7.74 (m, 1H), 7.00 (s, 1H), 6.81-6.90 (m, 2H), 6.67-6.73 (m, 1H), 6.50 (s, 1H), 4.93 (s, 2H), 3.90 (s, 2H), 3.53 (t, J=6.6 Hz, 2H) 2.64 (t, J=7.5 Hz, 2H), 1.80-1.71 (m, 2H). Mass spectrum (ESI, m/z): Calculated for C$_{21}$H$_{19}$F$_5$N$_2$O$_3$, 443.1 (M+H), found 443.1

Example 58

3-(3,5-difluoro-4-[[1-(6-methoxypyridin-3-yl)-3-(trifluoromethyl)-1H-pyrrol-2-yl]methoxy]phenyl)) propanoic acid (Compound #51)

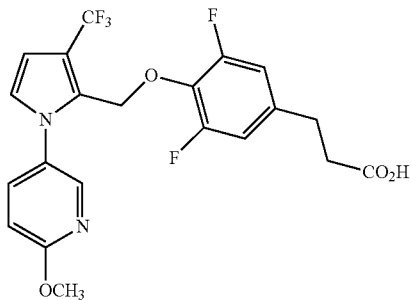 [SMILES: COc1ccc(-n2ccc(C(F)(F)F)c2COc2c(F)cc(CCC(=O)O)cc2F)cn1]

$^1$H NMR (300 MHz, CD$_3$OD) δ: 8.21 (s, 1H), 7.75-7.79 (m, 1H), 6.76-6.98 (m, 4H), 6.45 (s, 1H), 4.95 (s, 2H), 3.95 (s, 3H), 2.81 (t, J=7.5 Hz, 2H) 2.55 (t, J=7.2 Hz, 2H). Mass spectrum (ESI, m/z): Calculated for C$_{21}$H$_{17}$F$_5$N$_2$O$_4$, 455.1 (M−H), found 455.1

Example 59

3-(3,5-difluoro-4-[[1-(6-methoxypyridin-3-yl)-3-(trifluoromethyl)-1H-pyrrol-2-yl]methoxy]phenyl) propan-1-ol (Compound #52)

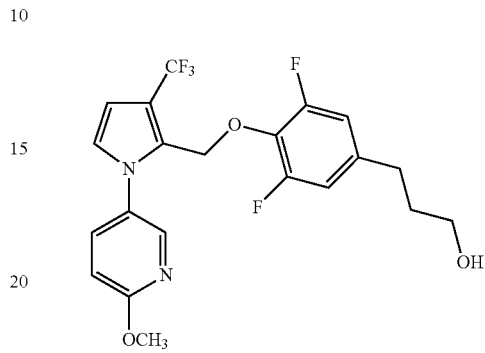

$^1$H NMR (300 MHz, CD$_3$OD) δ: 8.23 (s, 1H), 7.78-7.81 (m, 1H), 6.99 (s, 1H), 6.88 (d, J=7.2 Hz, 1H), 6.71-6.79 (m, 2H), 6.45 (s, 1H), 4.95 (s, 2H), 3.95 (s, 3H), 3.51 (t, J=6.3 Hz, 2H), 2.59 (t, J=7.5 Hz, 2H), 1.71-1.80 (m, 2H). Mass spectrum (ESI, m/z): Calculated for C$_{21}$H$_{19}$F$_5$N$_2$O$_3$, 443.1 (M+H), found 443.1

Example 60

3-(4-[[1-(4-chlorophenyl)-3-(trifluoromethyl)-1H-pyrrol-2-yl]methoxy]-3,5-difluorophenyl)-2-methyl-propanoic acid (Compound #59)

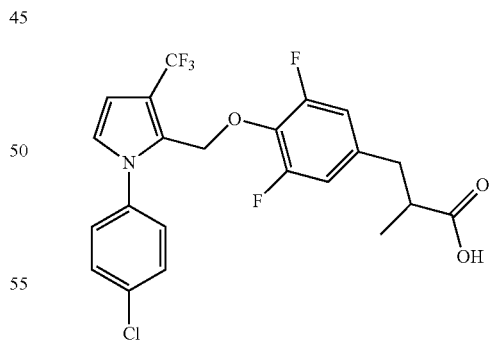

$^1$H NMR (300 MHz, CD$_3$OD) δ: 7.54 (s, 4H), 7.05 (d, J=3.0 Hz, 1H), 6.82 (d, J=13.8 Hz, 2H), 6.50 (d, J=3.0 Hz, 1H), 5.02 (s, 2H), 2.88-2.95 (m, 1H), 2.61-2.73 (m, 2H), 1.15 (d, J=6.6 Hz, 3H). Mass spectrum (ESI, m/z): Calculated for C$_{22}$H$_{17}$ClF$_5$NO$_3$, 472.1 (M−H), found 472.1

Example 61

3-(3,5-difluoro-4-[[1-(4-fluorophenyl)-3-(trifluoromethyl)-1H-pyrrol-2-yl]methoxy]phenyl)-2-methyl-propanoic acid (Compound #65)

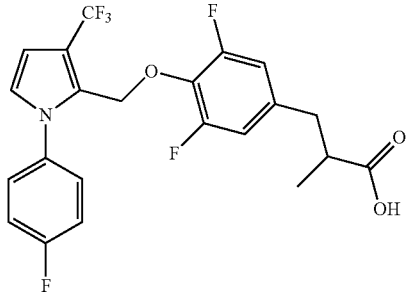 [SMILES: CC(Cc1cc(F)c(OCc2c(C(F)(F)F)ccn2-c2ccc(F)cc2)c(F)c1)C(=O)O]

$^1$H NMR (300 MHz, CD$_3$OD) δ: 7.50-7.57 (m, 2H), 7.22-7.30 (m, 2H), 7.02 (s, 1H), 6.76-6.84 (m, 2H), 6.48 (s, 1H), 4.99 (s, 2H), 2.84-2.96 (m, 1H), 2.60-2.74 (m, 2H), 1.16 (d, J=6.6 Hz, 3H). Mass spectrum (ESI, m/z): Calculated for C$_{22}$H$_{17}$F$_6$NO$_3$, 456.1 (M−H), found 456.0

Example 62

3-(3,5-difluoro-4-[[1-(4-methylphenyl)-3-(trifluoromethyl)-1H-pyrrol-2-yl]methoxy]phenyl)-2-methylpropanoic acid (Compound #60)

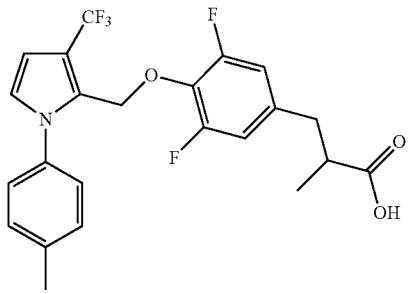 [SMILES: Cc1ccc(-n2ccc(C(F)(F)F)c2COc2c(F)cc(CC(C)C(=O)O)cc2F)cc1]

$^1$H NMR (300 MHz, CD$_3$OD) δ: 7.30-7.39 (m, 4H), 6.99 (s, 1H), 6.75-6.83 (m, 2H), 6.46 (s, 1H), 4.98 (s, 2H), 2.88-2.96 (m, 1H), 2.60-2.74 (m, 2H), 2.43 (s, 3H), 1.14 (d, J=6.3 Hz, 3H). Mass spectrum (ESI, m/z): Calculated for C$_{23}$H$_{20}$F$_5$NO$_3$, 452.1 (M−H), found 452.2.

Example 63

3-(4-[[1-(4-ethylphenyl)-3-(trifluoromethyl)-1H-pyrrol-2-yl]methoxy]-3,5-difluorophenyl)-2-methyl-propanoic acid (Compound #61)

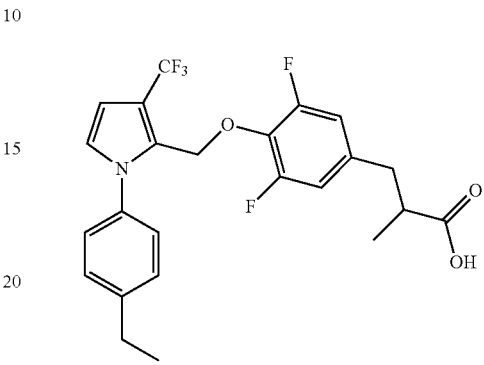

$^1$H NMR (300 MHz, CD$_3$OD) δ: 7.34-7.46 (m, 4H), 7.00 (s, 1H), 6.80 (d, J=8.0 Hz, 2H), 6.47 (s, 1H), 5.05 (s, 2H), 2.89-2.95 (m, 1H), 2.61-2.78 (m, 2H), 1.30 (t, J=7.5 Hz, 3H), 1.16 (d, J=6.4 Hz, 3H). Mass spectrum (ESI, m/z): Calculated for C$_{24}$H$_{22}$F$_5$NO$_3$, 466.2 (M−H), found 466.2

Example 64

3-(4-[[1-(4-chloro-3-fluorophenyl)-3-(trifluoromethyl)-1H-pyrrol-2-yl]methoxy]-3,5-difluorophenyl)-2-methylpropanoic acid (Compound #69)

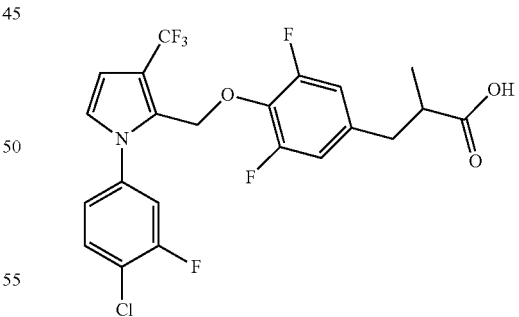

$^1$H NMR (300 MHz, CD$_3$OD) δ: 7.66 (t, J=6.3 Hz, 1H), 7.57 (d, J=7.2 Hz, 1H), 7.43 (d, J=6.3 Hz, 2H), 7.11 (s, 1H), 6.83 (d, J=13.2 Hz, 2H), 6.52 (s, 1H), 5.05 (s, 2H), 2.91-2.95 (m, 1H), 2.63-2.74 (m, 2H), 1.01 (d, J=5.7 Hz, 3H). Mass spectrum (ESI, m/z): Calculated for C$_{22}$H$_{16}$ClF$_6$NO$_3$, 490.1 (M−H), found 490.0.

Example 65

3-(3,5-difluoro-4-[[1-(3-fluoro-4-methylphenyl)-3-(trifluoromethyl)-1H-pyrrol-2-yl]methoxy]phenyl)-2-methylpropanoic acid (Compound #64)

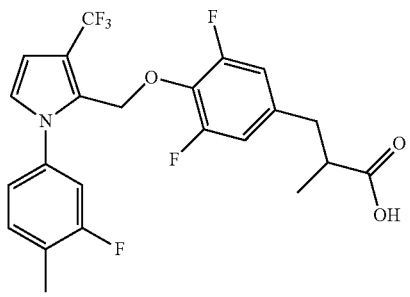 [SMILES: Cc1ccc(-n2ccc(C(F)(F)F)c2COc2c(F)cc(CC(C)C(=O)O)cc2F)cc1F]

$^1$H NMR (300 MHz, CD$_3$OD) δ: 7.40 (t, J=8.0 Hz, 1H), 7.28 (t, J=9.3 Hz, 2H), 7.04 (s, 1H), 6.80 (d, J=8.0 Hz, 2H), 6.49 (s, 1H), 5.02 (s, 2H), 2.90-2.95 (m, 1H), 2.62-2.74 (m, 2H), 2.36 (s, 3H), 1.16 (d, J=6.4 Hz, 3H). Mass spectrum (ESI, m/z): Calculated for C$_{23}$H$_{19}$F$_6$NO$_3$, 470.1 (M–H), found 470.1.

Example 66

3-(4-[[1-(4-chloro-3-fluorophenyl)-3-(trifluoromethyl)-1H-pyrrol-2-yl]methoxy]-3,5-difluorophenyl)propanoic acid (Compound #67)

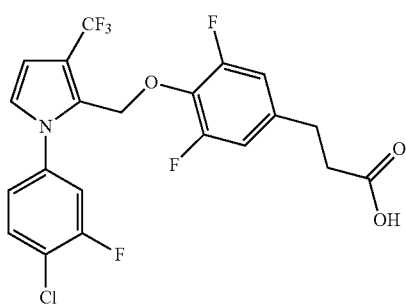 [SMILES: O=C(O)CCc1cc(F)c(OCc2c(C(F)(F)F)ccn2-c2ccc(Cl)c(F)c2)c(F)c1]

$^1$H NMR (300 MHz, CD$_3$OD) δ: 7.65 (t, J=8.4 Hz, 1H), 7.40-7.44 (m, 1H), 7.38-7.39 (m, 1H), 7.10 (s, 1H), 6.81-6.93 (m, 2H), 6.57 (s, 1H), 5.05 (s, 2H), 2.85 (t, J=7.5 Hz, 2H), 2.59 (t, J=7.5 Hz, 2H). Mass spectrum (ESI, m/z): Calculated for C$_{21}$H$_{14}$ClF$_6$NO$_3$, 476.1 (M–H), found 476.1.

Example 67

3-(3,5-difluoro-4-[[1-(3-fluoro-4-methylphenyl)-3-(trifluoromethyl)-1H-pyrrol-2-yl]methoxy]phenyl)propanoic acid (Compound #62)

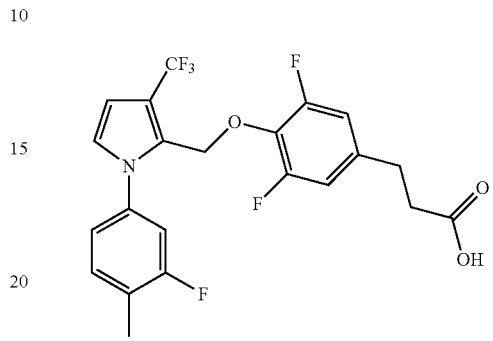

$^1$H NMR (300 MHz, CD$_3$OD) δ: 7.38 (t, J=8.1 Hz, 1H), 7.22-7.28 (m, 2H), 7.03 (s, 1H), 6.78-6.86 (m, 2H), 6.48 (s, 1H), 5.01 (s, 2H), 2.86 (t, J=7.5 Hz, 2H), 2.58 (t, J=7.2 Hz, 2H), 2.35 (s, 3H). Mass spectrum (ESI, m/z): Calculated for C$_{22}$H$_{17}$F$_6$NO$_3$, 456.1 (M–H), found 456.0.

Example 68

3-(4-[[1-(4-chloro-3-fluorophenyl)-3-(trifluoromethyl)-1H-pyrrol-2-yl]methoxy]-2,3-dimethylphenyl)propanoic acid (Compound #68)

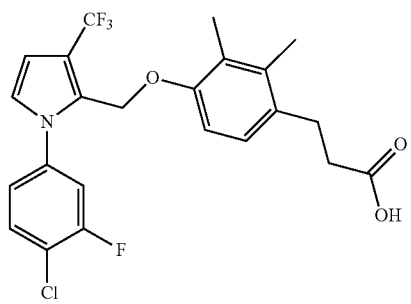 [SMILES: Cc1c(CCC(=O)O)ccc(OCc2c(C(F)(F)F)ccn2-c2ccc(Cl)c(F)c2)c1C]

$^1$H NMR (300 MHz, CD$_3$OD) δ: 7.57 (t, J=8.4 Hz, 1H), 7.39 (d, J=9.6 Hz, 1H), 7.28 (d, J=7.8 Hz, 1H), 7.07 (s, 1H), 6.91 (d, J=8.7 Hz, 1H), 6.55-6.63 (m, 2H), 5.03 (s, 2H), 2.89 (t, J=7.5 Hz, 2H), 2.49 (t, J=7.5 Hz, 2H), 2.21 (s, 3H), 2.01 (s, 3H). Mass spectrum (ESI, m/z): Calculated for C$_{23}$H$_{20}$ClF$_4$NO$_3$, 468.1 (M–H), found 468.2.

Example 69

3-(4-[[1-(3-fluoro-4-methylphenyl)-3-(trifluoromethyl)-1H-pyrrol-2-yl]methoxy]-2,3-dimethylphenyl) propanoic acid (Compound #66)

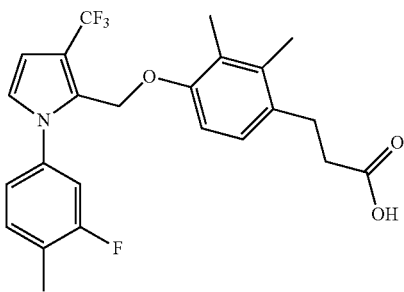 [SMILES: Cc1ccc(-n2ccc(C(F)(F)F)c2COc2ccc(CCC(=O)O)c(C)c2C)cc1F]

$^1$H NMR (300 MHz, CD$_3$OD) δ: 7.33 (t, J=8.0 Hz, 1H), 7.17 (d, J=8.8 Hz, 1H), 7.03 (s, 1H), 6.91 (d, J=8.4 Hz, 1H), 6.60 (d, J=8.4 Hz, 1H), 6.79-6.87 (m, 2H), 6.54 (s, 1H), 4.89 (s, 2H), 2.90 (t, J=7.6 Hz, 2H), 2.50 (t, J=7.6 Hz, 2H), 2.31 (s, 3H), 2.22 (s, 3H), 2.05 (s, 3H). Mass spectrum (ESI, m/z): Calculated for C$_{24}$H$_{23}$F$_4$NO$_3$, 448.1 (M−H), found 448.1

Example 70

3-(4-[[1-(4-chlorophenyl)-3-(trifluoromethyl)-1H-pyrrol-2-yl]methoxy]-3,5-difluorophenyl)propanoic acid (Compound #70) and 3-(4-((1-(4-chlorophenyl)-3-(perfluoroethyl)-1H-pyrrol-2-yl)methoxy)-3,5-difluorophenyl)propanoic acid (Compound #63)

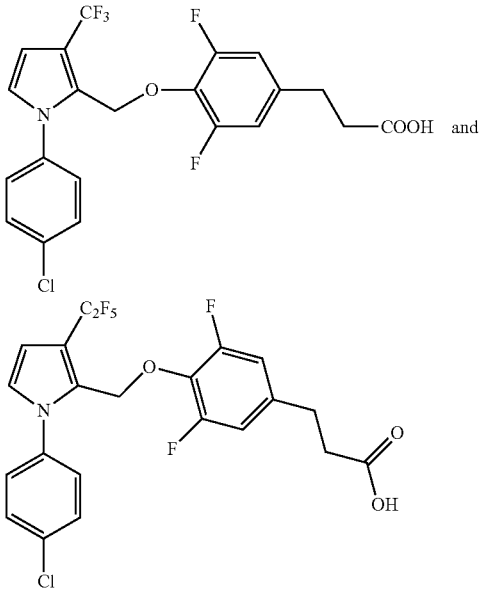

Step A: Methyl 3-trofloromethyl-1H-pyrrole-2-carboxylate and methyl 3-(perfluoroethyl)-1-(phenylsulfonyl)-1H-pyrrole-2-carboxylate

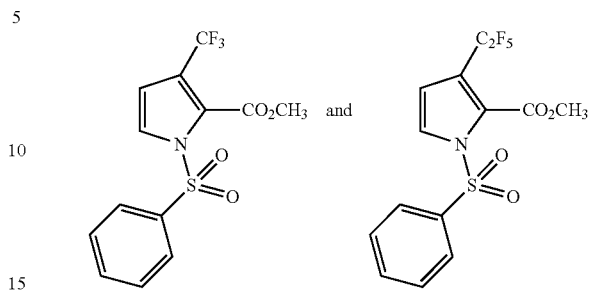

Into a 250-mL round-bottom flask (1 atm) purged and maintained with an inert atmosphere of nitrogen, was placed methyl 1-(benzenesulfonyl)-3-bromo-1H-pyrrole-2-carboxylate (6.7 g, 19.47 mmol, 1.00 equiv), methyl 2,2-difluoro-2-(fluorosulfonyl)acetate (15 g, 78.08 mmol, 4.01 equiv), CuI (15 g, 78.76 mmol, 4.05 equiv), N,N-dimethylformamide (40 mL) and NMP (40 mL). The resulting solution was stirred for 2 days at 100° C. in an oil bath. The reaction progress was monitored by LCMS. The reaction was then quenched by the addition of water (50 ml). The resulting solution was diluted with water (20 mL). The resulting mixture was washed with brine (3×100 mL) and sodium chloride (1×20 mL). The resulting mixture was then concentrated under vacuum. The resulting residue was applied onto a silica gel column with ethyl acetate/petroleum ether (1/30) to yield a mixture of methyl 1-(benzenesulfonyl)-3-(trifluoromethyl)-1H-pyrrole-2-carboxylate and methyl 3-(perfluoroethyl)-1-(phenylsulfonyl)-1H-pyrrole-2-carboxylate and methyl 3-bromo-1-(phenylsulfonyl)-1H-pyrrole-2-carboxylate as yellow oil.

Into a 250-mL round-bottom flask, was placed the mixture of methyl 1-(benzenesulfonyl)-3-bromo-1H-pyrrole-2-carboxylate and methyl 3-(perfluoroethyl)-1-(phenylsulfonyl)-1H-pyrrole-2-carboxylate and methyl 3-bromo-1-(phenylsulfonyl)-1H-pyrrole-2-carboxylate (4.0 g, 11.62 mmol, 1.00 equiv), ethanol (40.00 mL), Pd/C (10.0 g). The resulting solution subjected to 2 atm of H$_2$ and stirred for 2 days at 25° C. The reaction progress was monitored by LCMS. The solids were filtered out and the resulting mixture was then concentrated under vacuum. The resulting residue was applied onto a silica gel column with ethyl acetate/petroleum ether (1:30) to yield methyl 3-trofloromethyl-1H-pyrrole-2-carboxylate and methyl 3-(perfluoroethyl)-1-(phenylsulfonyl)-1H-pyrrole-2-carboxylate as a light yellow oil.

Step B: Methyl 3-(trifluoromethyl)-1H-pyrrole-2-carboxylate and methyl 3-(perfluoroethyl)-1H-pyrrole-2-carboxylate

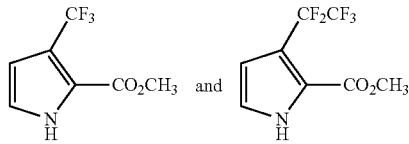

Into a 100-mL round-bottom flask, was placed methyl 1-(benzenesulfonyl)-3-(trifluoromethyl)-1H-pyrrole-2-carboxylate and methyl 3-(perfluoroethyl)-1-(phenylsulfonyl)-1H-pyrrole-2-carboxylate (1.8 g, 5.40 mmol, 1.00 equiv) and tetrahydrofuran (15.0 mL). To the resulting mixture was then added NaOCH$_3$ (1.17 g, 21.67 mmol, 4.01 equiv), in portions at 0° C. The resulting solution was stirred for 30 min at 0° C. in a water/ice bath. The reaction progress was monitored by LCMS. The reaction was then quenched by the addition of 2N hydrogen chloride until the solution became clear. The resulting solution was extracted with ethyl acetate (3×20 mL) and the organic layers combined. The resulting mixture was washed with sodium chloride (1×20 mL). The resulting mixture was dried over anhydrous sodium sulfate and concentrated under vacuum to yield methyl 3-(trifluoromethyl)-1H-pyrrole-2-carboxylate and methyl 3-(perfluoroethyl)-1-(phenylsulfonyl)-1H-pyrrole-2-carboxylate as a yellow solid. The yellow soli, was used in the next step without further purification.

Step C: Methyl 1-(4-chlorophenyl)-3-(trifluoromethyl)-1H-pyrrole-2-carboxylate and methyl 1-(4-chlorophenyl)-3-(perfluoroethyl)-1H-pyrrole-2-carboxylate

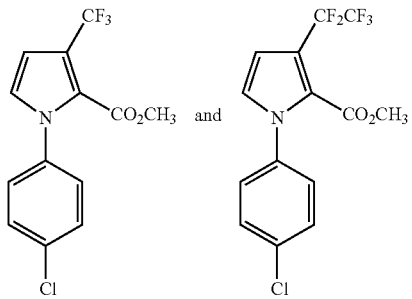

Into a 50-mL round-bottom flask purged and maintained with an inert atmosphere of nitrogen, was placed methyl 3-(trifluoromethyl)-1H-pyrrole-2-carboxylate and methyl 3-(perfluoroethyl)-1H-pyrrole-2-carboxylate (300 mg, 1.55 mmol, 1.00 equiv), (4-chlorophenyl)boronic acid (727 mg, 4.65 mmol, 3.00 equiv), Cu(AcO)$_2$ (562 mg, 2.00 equiv), pyridine (491 mg, 6.21 mmol, 4.00 equiv) and dichloromethane (20 mL). The resulting solution was stirred for 2d at 20° C. The solids were filtered out. The resulting residue was applied onto a silica gel column with ethyl acetate/petroleum ether (1:15) to yield methyl 1-(4-chlorophenyl)-3-(trifluoromethyl)-1H-pyrrole-2-carboxylate and methyl 1-(4-chlorophenyl)-3-(perfluoroethyl)-1H-pyrrole-2-carboxylate as yellow oil.

Step D: [1-(4-chlorophenyl)-3-(trifluoromethyl)-1H-pyrrol-2-yl]methanol and (1-(4-chlorophenyl)-3-(perfluoroethyl)-1H-pyrrol-2-yl)methanol

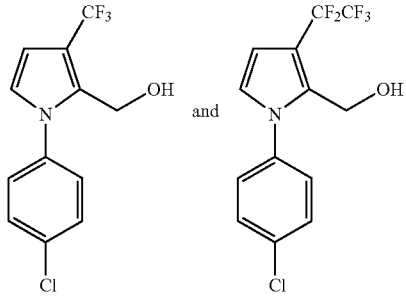

Into a 25-mL round-bottom flask, was placed methyl 1-(4-chlorophenyl)-3-(trifluoromethyl)-1H-pyrrole-2-carboxylate and methyl 1-(4-chlorophenyl)-3-(perfluoroethyl)-1H-pyrrole-2-carboxylate (200 mg, 0.66 mmol, 1.00 equiv), LAH (50 mg, 1.32 mmol, 2.00 equiv) and tetrahydrofuran (5 mL). The resulting solution was stirred for 2 h at 0° C. in a water/ice bath. The reaction was then quenched by the addition of 3 mL of water. The resulting solution was extracted with ethyl acetate (5×10 mL) and the organic layers combined. The resulting residue was applied onto a silica gel column with ethyl acetate/petroleum ether (1:6) to yield [1-(4-chlorophenyl)-3-(trifluoromethyl)-1H-pyrrol-2-yl] methanol and (1-(4-chlorophenyl)-3-(perfluoroethyl)-1H-pyrrol-2-yl)methanol as yellow oil.

Step E: Ethyl 3-(4-[[1-(4-chlorophenyl)-3-(trifluoromethyl)-1H-pyrrol-2-yl]methoxy]-3,5-difluorophenyl propanoate and 1-(4-chlorophenyl)-2-((2,6-difluoro-4-propylphenoxy)methyl)-3-(perfluoroethyl)-1H-pyrrole

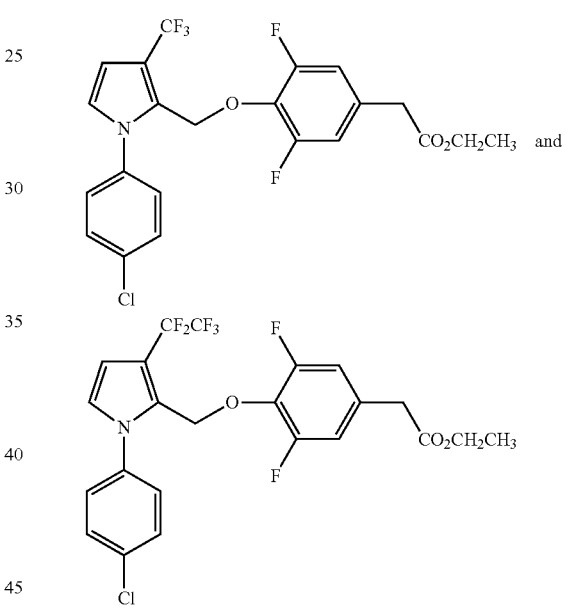

Into a 50-mL round-bottom flask purged and maintained with an inert atmosphere of nitrogen, was placed [1-(4-chlorophenyl)-3-(trifluoromethyl)-1H-pyrrol-2-yl]methanol and (1-(4-chlorophenyl)-3-(perfluoroethyl)-1H-pyrrol-2-yl) methanol (200 mg, 0.73 mmol, 1.00 equiv), ethyl 3-(3,5-difluoro-4-hydroxyphenyl)propanoate (211 mg, 0.92 mmol, 1.20 equiv), ADDP (482 mg, 1.91 mmol, 2.50 equiv), PBu$_3$ (232 mg, 1.15 mmol, 1.50 equiv) and toluene (10 mL). The resulting solution was stirred overnight at 60° C. in an oil bath. The reaction progress was monitored by LCMS. The resulting mixture was then concentrated under vacuum. The resulting solution was diluted with diethyl ether (10 mL). The solids were filtered out and the resulting mixture was concentrated under vacuum. The resulting residue was applied onto a silica gel column with ethyl acetate/petroleum ether (1:10) to yield ethyl 3-(4-[[1-(4-chlorophenyl)-3-(trifluoromethyl)-1H-pyrrol-2-yl]methoxy]-3,5-difluorophenyl propanoate and 1-(4-chlorophenyl)-2-((2,6-difluoro-4-propylphenoxy)methyl)-3-(perfluoroethyl)-1H-pyrrole as yellow oil.

Step F: 3-(4-[[1-(4-chlorophenyl)-3-(trifluoromethyl)-1H-pyrrol-2-yl]methoxy]-3,5-difluorophenyl)propanoic acid and 3-(4-((1-(4-chlorophenyl)-3-(perfluoroethyl)-1H-pyrrol-2-yl)methoxy)-3,5-difluorophenyl) propanoic acid

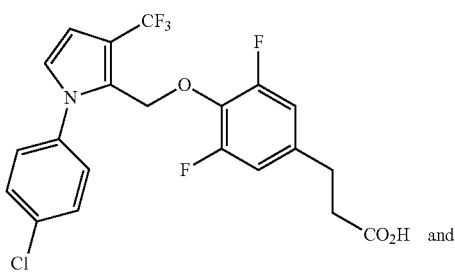

and

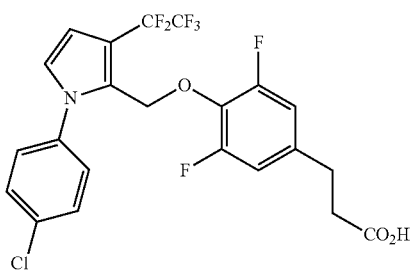

Into a 100-mL round-bottom flask, was placed tetrahydrofuran (10 mL) ethyl 3-(4-[[1-(4-chlorophenyl)-3-(trifluoromethyl)-1H-pyrrol-2-yl]methoxy]-3,5-difluorophenyl)propanoate (1.5 g, 3.07 mmol, 1.00 equiv), LiOH (2 g, 83.51 mmol, 27.00 equiv) and water (10 mL). The resulting solution was stirred overnight at 25° C. The pH value of the solution was adjusted to pH5 with hydrogen chloride (6 mol/L). The resulting solution was extracted with ethyl acetate (3×10 ml) and the organic layers combined and concentrated under vacuum. The resulting residue (1.5 g) was purified by Flash-Prep-HPLC with the following conditions (IntelFlash-1): Column, C18; mobile phase, $CH_3CN$/water=1/3 increasing to $CH_3CN$/water=3/2 within 30 min; Detector, UV 254 nm to yield:

3-(4-[[1-(4-chlorophenyl)-3-(trifluoromethyl)-1H-pyrrol-2-yl]methoxy]-3,5-difluorophenyl)propanoic acid (Compound #70) as a off-white solid (1 g, 68%)

$^1$H NMR (300 MHz, $CD_3OD$) δ 7.52 (s, 4H), 7.03 (d, J=2.7 Hz, 1H), 6.80-6.83 (m, 2H), 4.99 (d, J=2.7 Hz, 1H), 5.00 (s, 2H), 2.84 (t, J=7.8 Hz, 2H), 2.41 (t, J=7.8 Hz, 2H). Mass spectrum (ESI, m/z): Calculated for $C_{21}H_{15}ClF_5NO_3$, 458.1 (M−H), found 458.1; and 3-(4-((1-(4-chlorophenyl)-3-(perfluoroethyl)-1H-pyrrol-2-yl)methoxy)-3,5-difluorophenyl)propanoic acid (Compound #63) as a off-white solid (26.5 mg).

$^1$H NMR (300 MHz, $CD_3OD$) δ 7.52 (s, 4H), 7.22-7.28 (m, 2H), 7.09 (s, 1H), 6.79-6.87 (m, 2H), 6.48 (s, 1H), 4.99 (s, 2H), 2.85 (t, J=7.5 Hz, 2H), 2.59 (t, J=7.2 Hz, 2H), 2.35 (s, 3H). Mass spectrum (ESI, m/z): Calculated for $C_{22}H_{15}ClF_7NO_3$, 508.1 (M−H), found 508.0

Example 71

(6-ethylpyridin-3-yl)boronic acid

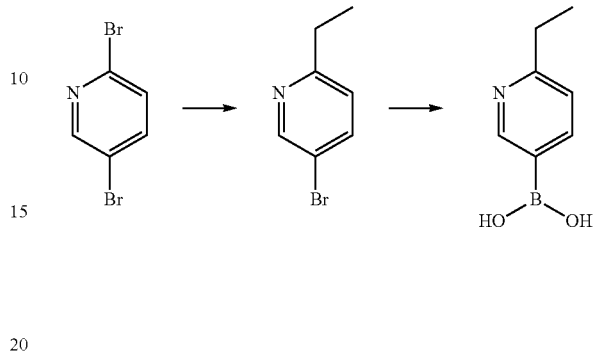

Step A: 5-bromo-2-ethylpyridine

Into a 1000-mL 3-necked round-bottom flask (1 atm) purged and maintained with an inert atmosphere of nitrogen, was placed 2,5-dibromopyridine (20 g, 84.43 mmol, 1.00 equiv), $Pd(PPh_3)_4$ (9.7 g, 8.39 mmol, 0.10 equiv) and tetrahydrofuran (500 mL). To the resulting mixture was then added diethylzinc (46.2 mL) dropwise with stirring at −78° C. The resulting solution was stirred overnight at room temperature. The reaction was then quenched by the addition of water (10 mL). The resulting mixture was then concentrated under vacuum. The resulting solution was diluted with ethyl acetate (200 mL). The resulting solution was extracted with 4N HCl (2×200 mL) and the aqueous layers combined. The pH value of the solution was adjusted to pH 14 with aqueous LiOH. The resulting solution was extracted with ethyl acetate (2×200 mL) and the organic layers combined. The resulting residue was applied onto a silica gel column with ethyl acetate/petroleum ether (4.6/95.4) to yield 5-bromo-2-ethylpyridine as colorless oil.

Step B: (6-ethylpyridin-3-yl)boronic acid

Into a 500-mL 3-necked round-bottom flask (1 atm) purged and maintained with an inert atmosphere of nitrogen, was placed 5-bromo-2-ethylpyridine (3 g, 16.12 mmol, 1.00 equiv) and tetrahydrofuran (200 mL). To the resulting mixture was then added n-BuLi (8.4 mL, 2.5 M) dropwise with stirring at −78° C. The resulting solution was stirred for 30 min at −78° C. in an ethanol/$N_2$ bath. To the resulting mixture was then added triethyl borate (4.7 g, 32.19 mmol, 2.00 equiv) dropwise with stirring at −78° C. The resulting solution was allowed to react, with stirring, overnight at room temperature. The reaction was then quenched by the addition of methanol (20 mL) and water (0.5 mL). The resulting mixture was then concentrated under vacuum. The resulting solution was diluted with methanol (10 mL). The resulting residue (10 mL) was purified by Flash-Prep-HPLC (reversed column) with the following conditions (IntelFlash-1): Column, C18 silica gel; mobile phase, A:water with trifluoroacetic acid (0.05%); B: MeCN=1/100 increasing to A:water with trifluoroacetic acid (0.05%); B: MeCN=20/100 within 25 min; Detector, UV 254 nm to yield of (6-ethylpyridin-3-yl)boronic acid as a white solid.

Example 72

Ethyl 3-(3,5-difluoro-4-hydroxyphenyl)-2-methylpropanoate and Ethyl 3-(3-(benzyloxy)-2,4-difluorophenyl)-2-methylpropanoate

Step A: 4-(benzyloxy)-3,5-difluorobenzaldehyde/3-(benzyloxy)-2,4-difluorobenzaldehyde

Step B: Ethyl (2E)-3-[4-(benzyloxy)-3,5-difluorophenyl]-2-methylprop-2-enoate and ethyl (2E)-3-[3-(benzyloxy)-2,4-difluorophenyl]-2-methylprop-2-enoate

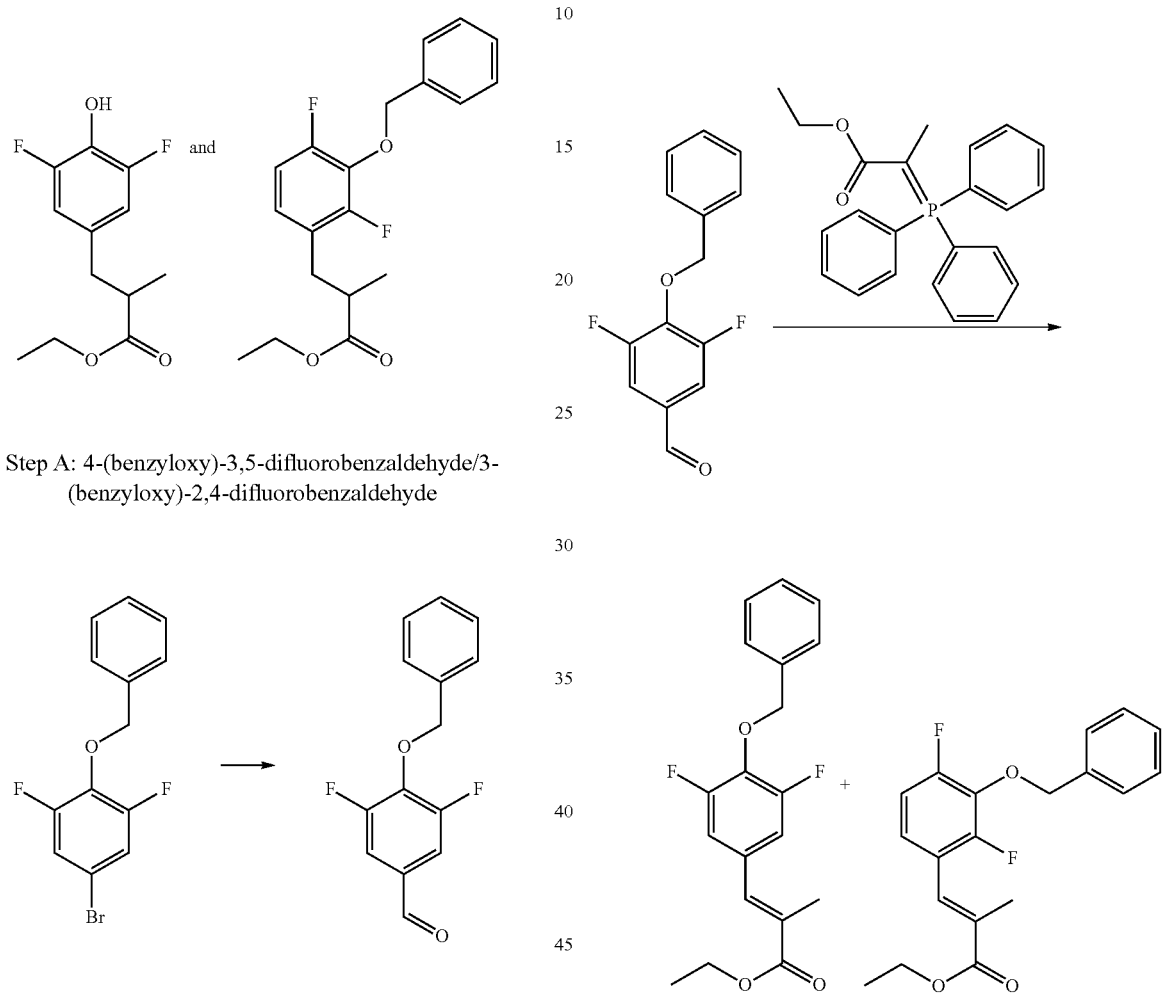

Into a 100-mL round-bottom flask purged and maintained with an inert atmosphere of nitrogen, was placed a solution of 2-(benzyloxy)-5-bromo-1,3-difluorobenzene (7.0 g, 23.40 mmol, 1.00 equiv) in tetrahydrofuran (20 mL) at −78° C. To the resulting mixture was then added n-BuLi (11.3 mL). The resulting mixture was stirred for 1 h at −78° C. To the resulting mixture was then added N, N-dimethylformamide (6 mL). The resulting solution was stirred for 1 h at −78° C. The reaction was then quenched by the addition of water (10 mL). The resulting solution was extracted with ethyl acetate (3×20 mL) and the organic layers combined and dried over anhydrous sodium sulfate. The solids were filtered out and the resulting mixture was then concentrated under vacuum. The residue was applied onto a silica gel column with ethyl acetate/petroleum ether (1:8) to yield 4-(benzyloxy)-3,5-difluorobenzaldehyde/3-(benzyloxy)-2,4-difluorobenzaldehyde as colorless oil.

Into a 100-mL round-bottom flask, was placed 4-(benzyloxy)-3,5-difluorobenzaldehyde and 3-(benzyloxy)-2,4-difluorobenzaldehyde (4 g, 16.11 mmol, 1.00 equiv, crude), ethyl 2-(triphenylphosphoranylidene)propanoate (8.75 g, 24.14 mmol, 1.50 equiv) and toluene (60 mL). The resulting solution was stirred for 12 h at 110° C. The resulting mixture was then concentrated under vacuum. The resulting residue was applied onto a silica gel column with ethyl acetate/petroleum ether (1:8) to yield ethyl (2E)-3-[4-(benzyloxy)-3,5-difluorophenyl]-2-methylprop-2-enoate and ethyl (2E)-3-[3-(benzyloxy)-2,4-difluorophenyl]-2-methylprop-2-enoate as yellow oil.

Step C: Ethyl 3-(3,5-difluoro-4-hydroxyphenyl)-2-methylpropanoate and ethyl 3-(3-(benzyloxy)-2,4-difluorophenyl)-2-methylpropanoate

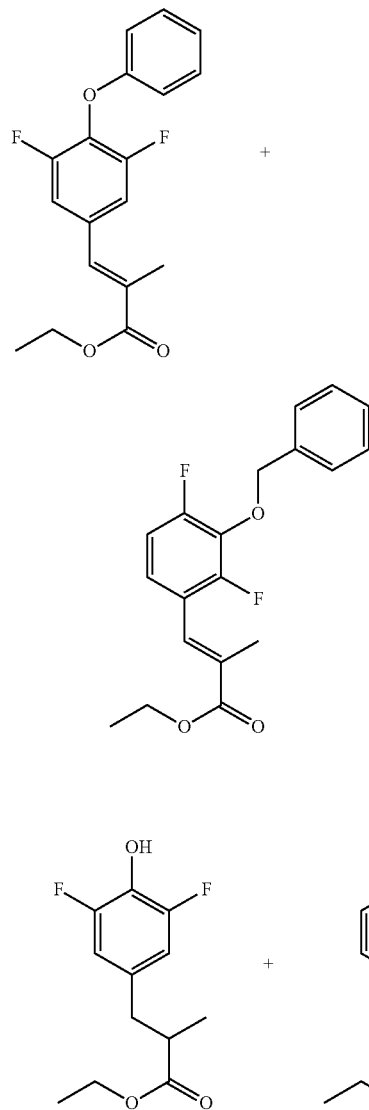

Into a 100-mL round-bottom flask, was placed a solution of ethyl (2E)-3-[3-(benzyloxy)-2,4-difluorophenyl]-2-methylprop-2-enoate and ethyl (2E)-3-[4-(benzyloxy)-3,5-difluorophenyl]-2-methylprop-2-enoate (4 g, 12.04 mmol, 1.00 equiv) in EtOAc (50 ml) and palladium carbon (2.5 g). Into the resulting mixture was then introduced H$_2$(g). The resulting solution was stirred overnight at 25° C. The solids were filtered out and the resulting mixture was concentrated under vacuum. The resulting residue was applied onto a silica gel column with ethyl acetate/petroleum ether (1:4) to yield ethyl 3-(3,5-difluoro-4-hydroxyphenyl)-2-methylpropanoate and ethyl 3-(3-(benzyloxy)-2,4-difluorophenyl)-2-methylpropanoate as colorless oil.

Example 73

Ethyl 1-(4-chlorophenyl)-3-(trifluoromethyl)-1H-pyrrole-2-carboxylate

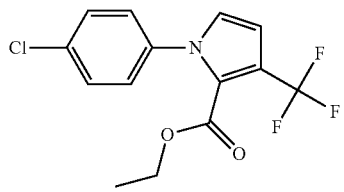 [SMILES: CCOC(=O)c1c(C(F)(F)F)ccn1-c1ccc(Cl)cc1]

Step A: Ethyl 2-((4-chlorophenyl)amino)acetate

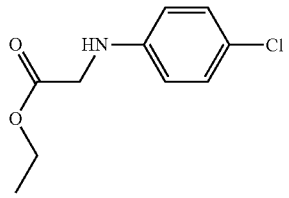

A mixture of 4-chloroaniline (12.8 g, 100.3 mmol), ethyl bromoacetate (12.2 mL, 110.4 mmol). and potassium carbonate (13.9 g, 100.3 mmol) in acetonitrile (330 mL) was heated overnight at 80° C. The resulting mixture was cooled to room temperature and filtered. The filtrate was concentrated and triturated DCM and the resulting solid was filtered to yield ethyl 2-((4-chlorophenyl)amino)acetate.
$^1$H NMR (CHLOROFORM-d) δ: 7.10-7.18 (m, 2H), 6.49-6.57 (m, 2H), 4.16-4.44 (m, 3H), 3.87 (s, 2H), 1.30 (t, J=7.2 Hz, 3H).

Step B: (E)-Ethyl 2-((4-chlorophenyl)(4,4,4-trifluoro-3-oxobut-1-en-1-yl)amino)acetate

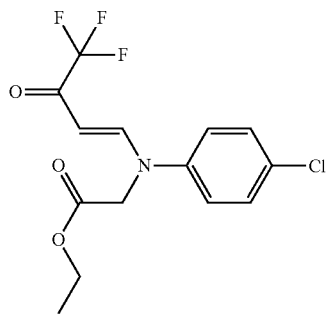 [SMILES: CCOC(=O)CN(/C=C/C(=O)C(F)(F)F)c1ccc(Cl)cc1]

A mixture of ethyl 2-((4-chlorophenyl)amino)acetate (10.0 g, 46.8 mmol) and (E)-4-ethoxy-1,1,1-trifluorobut-3-en-2-one (11.0 g, 65.5 mmol) in DCM (150 mL) was heated overnight at 50° C. The resulting mixture was concentrated and then triturated with 20% EtOAc/heptane and the resulting solid filtered and washed with heptane to yield (E)-ethyl 2-((4-chlorophenyl)(4,4,4-trifluoro-3-oxobut-1-en-1-yl)amino)acetate.

$^1$H NMR (CHLOROFORM-d) d: 8.10 (br, 1H), 7.40 (d, J=8.1 Hz, 2H), 7.21 (d, J=7.6 Hz, 2H), 5.48 (br, 1H), 4.39 (s, 2H), 4.28 (q, J=7.1 Hz, 2H), 0.85-0.91 (m, 3H).

Step C: Ethyl 1-(4-chlorophenyl)-3-(trifluoromethyl)-1H-pyrrole-2-carboxylate

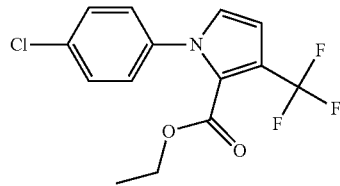

To a solution of (E)-ethyl 2-((4-chlorophenyl)(4,4,4-trifluoro-3-oxobut-1-en-1-yl)amino)acetate (0.95 g, 2.83 mmol) in EtOAc (20 mL) was added DBU (0.85 mL, 5.66 mmol) and the resulting mixture heated in a sealed tube for 90 min at 120° C. The resulting mixture was cooled to room temperature, diluted with EtOAc (80 mL) and washed with 5% KHSO$_4$ (2×80 mL) and brine (80 mL). The organic layer was concentrated and the residue purified by elution from a 25-g silica cartridge with 0-20% EtOAc/heptane to yield ethyl 1-(4-chlorophenyl)-3-(trifluoromethyl)-1H-pyrrole-2-carboxylate as a white solid.

$^1$H NMR (CHLOROFORM-d) d: 7.40-7.45 (m, 2H), 7.21-7.25 (m, 2H), 6.85 (d, J=2.5 Hz, 1H), 6.58 (d, J=2.5 Hz, 1H), 4.20 (q, J=7.1 Hz, 2H), 1.22 (t, 3H). $^{19}$F NMR (CHLOROFORM-d) d: −57.08. Mass spectrum (ESI, m/z): Calcd. for $C_{14}H_{11}ClF_3NO_2$, 318.0 (M+H), found 318.1

Biological Example 1

In Vitro Assay

Human GPR120 DiscoveRx PathHunter β-Arrestin Assay

Assay Principle:

The binding of an agonist (medium/long chain fatty acids or small molecule agonists) to the G-protein-coupled receptor GPR120 activates phospholipase C, leading to release of intracellular $Ca^{+2}$ through the generation of inositol 1,4,5-trisphosphate (InsP3 or IP3). GPR120 activation can also trigger intracellular signaling via recruitment of β-Arrestin. In the present method, agonist-induced activation of the human GPR120 receptor is monitored through the use of PathHunter CHO-K1 GPR120 β-Arrestin Cell Line engineered by DiscoveRx, as detailed below. The cell lines are designed to co-express both the ProLink/Enzyme Donor (PK)-tagged GPCR and the Enzyme Activator (EA)-tagged Beta-Arrestin fusion proteins. Upon GPR120 receptor stimulation/activation, the EA-tagged β-Arrestin portion is translocated to the tagged receptor, where the two enzyme fragments are brought within close proximity. Under these conditions, these fragments can interact and form an active Beta-gal enzyme complex through Enzyme Fragment Complementation (EFC). This active Beta-gal complex can enzymatically hydrolyse the substrate to produce a detectable light signal; therefore, activation as a function of agonist concentration can be expressed as an $EC_{50}$ value to determine relative compound activities. This in vitro assay therefore serves to assess compound agonist activity of the GPR120.

Procedure β-Arrestin A:

In Procedure β-arrestin A, the cell used were PathHunter CHO-K1 GPR120 β-Arrestin Cell Line, expressing the long form of human GPR120 (Genbank accession number NM__181745), with 3000 cells per well.

Procedure β-Arrestin B:

In Procedure β-arrestin B the cells used were PathHunter CHO-K1 GPR120 β-Arrestin Cell Line, expressing the short form of the GPR120 receptor (Accession #NM__181745), with 5000 cells/well.

Assay Procedure:

The selected CHO-K1 GPR120 β-Arrestin cells were cultured in Ham's F12 media supplemented with 10% fetal bovine serum (FBS), 1% Glutamine, 1×p/s, 800 μg/ml G418 and 300 μg/ml Hygromycin B (for selection). Cell stocks were maintained and grown in a sub-confluent state using standard cell culture procedures. The day before the experiment, the cells were harvested with non-enzymatic cell dissociation buffer and re-suspended in complete growth media at the desired concentration. A Corning 384-plate was then seeded with the proper number of cells in a volume of 25 μL, per well. The seeded plates were incubated overnight at 37° C.

On the day of the experiment, the Assay Buffer containing (a) HBSS with $Ca^{++}$ and $Mg^{++}$, (b) 20 mM HEPES, and (c) 0.1% BSA stabilizer (pH 7.4) was prepared. The growth medium was gently removed from the cell plates and 20 μL of Assay Buffer added to each well. The plate was then incubated at 37° C. for 60 mins. Test compounds were serially diluted in Assay Buffer to desired concentrations (more particularly, to one or more of the following μM concentrations: 25 μM, 12.5 μM, 6.25 μM, 3.125 μM, 1.562 μM, 0.781 μM, 0.391 μM, 0.195 μM, 0.098 μM, 0.049 μM, 0.024 μM, 0.012 μM). Five μl of compound dilution was then added to each well and the plate incubated at 37° C. for 90 mins. The detection reagents were prepared according to the manufacture's instruction. Twelve μL of the detection reagents were added to each well and the plate incubated at room temperature for 60 mins.

The plates were read on an EnVision instrument, using Protocol name: Luminescence, Plate type: 384 Costar, Measurement height: 3 mm, Measurement time: 1 s, Aperture: 384 Plate aperture. The % activity relative to the positive control was calculated using the following equation:

$$\% \text{ Activity} = \frac{Count_{compound} - Count_{vehicle}}{Count_{postivite\ control} - Count_{vehicle}} \times 100\%$$

The % Activity values were plotted versus the concentration of test compound and fitted to a sigmoidal dose-response curve with a Hill slope=1 (fixed value) using nonlinear regression with GraphPad Prism 5.0 to calculate the $EC_{50}$ values. The Fitting Equation was: Y=Bottom+(Top−Bottom)/(1+10^((Log $EC_{50}$−X)*HillSlope)), where X is the log of the concentration and Y is the response.

Biological Example 2

In Vitro Assay

Human GPR120 in Calcium Flux Assay

Assay Principle

This in vitro assay serves to assess test compound agonist activity against the short splice variant (SVS with Accession number NM_001195755.1 confirmed by sequencing data) of the GPR120 receptor. The Human Short splice variant #2 (NM_001195755.1) is missing an in-frame coding exon compared to variant 1 (the Human Long splice variant NM_181745.3), resulting in a shorter isoform (GPR120-S) lacking a 16 aa protein segment compared to isoform GPR120-L. The assay platform utilizes HEK-293 cells stably transfected to express the Human GPR120 short form. These cells are first loaded with the $Ca^{+2}$ sensitive dye, Fluo-4 NW. Upon stimulation, intracellular released $Ca^{+2}$ can bind to the dye and alter its fluorescence intensity. This increase in fluorescence signal, and thus the flux in intracellular $[Ca^{2+}]$, is detected and quantitated by fluorescence imaging using a FLIPR reader. The effect of the agonist is measured as a function of concentration and used to calculate an $EC_{50}$ based upon a response curve.

Procedure Calcium A:

In this procedure 2500 cells/well were employed.

Procedure Calcium B:

In this procedure 4200 cells/well were employed.

Assay Procedure:

A Human GPR120 clone (Genbank accession number NM_001195755.1) was placed into the pcDNA3.1 mammalian expression vector carrying the neomycin resistance gene. A stable mammalian cell was generated by placing the above clone into a HEK293 background. Clonal cells responding to long chain fatty acids had expression levels of GPR120 confirmed by RT-qPCR. Human HEK-GPR120 cells were cultured in Dulbecco's Modified Eagle's Medium (DMEM)/F12 medium supplemented with 10% fetal bovine serum (FBS), 1% L-Glutamine and 1% penicillin/streptomycin and 0.5 mg/ml G-418. Cells were split 2 times a week to keep the cells in the log-phase growth.

In preparation for the assay, HEK cells stably transfected with Human GPR120 (2.5K cells per well in 25 uL growth medium) were seeded into 384-well plates and then incubated overnight (37° C., 5% $CO_2$). The next day, the media was changed to 20 µl assay buffer and the cell starved for 1 h at 37° C. The dye loading solution (2× dye) was prepared using 10 ml assay buffer, 100 µl of 250 mM probenecid, 1 bottle of Component A, and 20 µl of dye in DMSO. Twenty µl of the 2× dye loading buffer was then added to each well. The plates were incubated at 37° C. for 30 min, then at room temperature for an additional 15 minutes, before performing the assay on FLIPR.

Test compounds were prepared in assay buffer (2 µl of test compound+198 µl assay buffer, final DMSO in assay plate is 0.2%) at the desired concentration, more particularly at 100 µM, 50 µM, 25 µM, 12.5 µM, 6.25 µM, 3.125 µM, 1.562 µM, 0.781 µM, 0.391 µM, 0.195 µM, 0.098 µM, 0.049 µM, 0.024 µM and 0.012 µM.

The assay was performed on a FLIPR plate reader using the following parameters. Baseline was read for 10 seconds at 1 sec intervals. The program was set to transfer 10 µL of ligand from compound plate to cell plate after baseline reading. Aspiration was executed at: 10 µl/sec speed, 4.6 µl height; Dispensing was executed at: 30 µl/sec speed, 45 µl height. After compound addition, each well was read for 300 sec, with measurements collected at 1 sec intervals.

The kinetic data from the FLIPR was based upon a 5 minute window for data collection. The fluorescence of each sample well was used for individual calculations of a normalized RFU value, which was defined as maximum response minus the minimum response. The normalized fluorescence reading (RFU) was calculated as follows:

$RFU = Fmax - Fmin$

The data were fitted to a sigmoidal dose-response curve with a variable Hill slope (<2) using nonlinear regression with GraphPad Prism 5.0 to calculate the $EC_{50}$ values. The Fitting Equation was: $Y = Bottom + (Top - Bottom)/(1 + 10^{\wedge}((Log\ EC_{50} - X) * HillSlope))$, where X is the log of the concentration and Y is the response.

Representative compounds of formula (I) were tested according to procedure as described in Biological Example 1 and 2 above, with results as listed in Table 3 below.

TABLE 3

| | GPR120 $EC_{50}$ (µM) | | | |
|---|---|---|---|---|
| ID No. | β-arrestin A $EC_{50}$ (µM) | B-arrestin B $EC_{50}$ (µM) | Calcium A $EC_{50}$ (µM) | Calcium B $EC_{50}$ (µM) |
| 1 | 1.035 | | 0.353 | |
| 2 | | | >19.9986 | |
| 3 | 0.592 | | 1.042 | 0.164 |
| 4 | | | >19.9986 | |
| 5 | 0.130 | | 0.435 | 0.368 |
| 6 | 0.730 | | 0.819 | 0.161 |
| 7 | | | 1.731 | 1.173 |
| 8 | 1.004 | | 0.528 | 0.173 |
| 9 | | | 3.709 | 1.365 |
| 10 | 0.258 | | 1.087 | 0.740 |
| 11 | 0.859 | | 0.934 | 0.161 |
| 12 | | | 4.255 | 1.139 |
| 13 | | | 1.556 | 0.899 |
| 14 | | | 2.890 | 1.396 |
| 15 | 1.104 | | 0.993 | 0.088 |
| 16 | 0.639 | | 0.836 | 0.091 |
| 17 | 0.238 | | 1.089 | 0.533 |
| 18 | | | 1.305 | 0.611 |
| 19 | 0.283 | | 0.843 | 0.261 |
| 20 | | | 1.267 | 0.289 |
| 21 | 0.087 | | 0.709 | 0.282 |
| 22 | | | 1.516 | 0.112 |
| 23 | | | 1.114 | 0.199 |
| 24 | 0.308 | | 0.931 | 0.227 |
| 25 | 0.203 | | 0.608 | 0.413 |
| 26 | 0.249 | | 0.916 | 0.230 |
| 27 | 0.046 | | 0.218 | 0.054 |
| 28 | 0.221 | | 0.641 | 0.108 |
| 29 | 0.053 | 0.063 | 1.006 | 0.162 |
| 30 | 0.025 | | 0.427 | 0.246 |
| 31 | 0.061 | | 0.222 | 0.067 |
| 32 | 0.357 | | 0.402 | 0.117 |
| 33 | 0.048 | | 0.434 | 0.082 |
| 34 | 0.171 | 0.179 | 0.517 | 0.040 |
| 35 | 0.201 | | 0.507 | 0.063 |
| 36 | 0.120 | | 0.444 | 0.145 |
| 37 | 0.016 | | 0.119 | 0.028 |
| 38 | 0.678 | | 0.450 | 0.101 |
| 39 | 0.264 | 0.219 | 0.306 | 0.050 |
| 40 | | | 1.920 | 0.896 |
| 41 | | | 1.264 | 0.247 |
| 42 | 0.293 | | 0.810 | 0.084 |
| 43 | 0.359 | | 0.558 | 0.063 |
| 44 | 0.098 | | 0.432 | 0.050 |
| 45 | | | 1.442 | 0.512 |
| 46 | 0.099 | | 0.621 | 0.043 |
| 47 | 0.241 | | 0.375 | 0.066 |
| 48 | 0.098 | | 0.098 | 0.030 |
| 49 | 1.242 | | 0.870 | 0.289 |
| 50 | | | 0.395 | 0.058 |
| 51 | | | 0.675 | 0.197 |
| 52 | | | 0.285 | 0.071 |
| 53 | | | 1.990 | 0.428 |
| 54 | | | 0.497 | 0.115 |
| 55 | | | 0.215 | 0.034 |
| 56 | | | 1.409 | 0.877 |
| 57 | | | 0.840 | 0.077 |
| 58 | 0.932 | | 0.882 | 0.162 |
| 59 | | 0.417 | | 0.290 |
| 60 | | 0.549 | | 0.186 |
| 61 | | 0.639 | | 0.236 |
| 62 | | 0.096 | | 0.262 |

TABLE 3-continued

| | GPR120 EC$_{50}$ (μM) | | | |
|---|---|---|---|---|
| ID No. | β-arrestin A EC$_{50}$ (μM) | B-arrestin B EC$_{50}$ (μM) | Calcium A EC$_{50}$ (μM) | Calcium B EC$_{50}$ (μM) |
| 63 | | | | 1.151 |
| 64 | | 0.264 | | 0.212 |
| 65 | | 0.809 | | 0.547 |
| 66 | | 0.412 | | 0.315 |
| 67 | | 0.206 | | 0.368 |
| 68 | | 0.311 | | 0.357 |
| 69 | | 0.630 | | 0.488 |
| 70 | | 0.069 | | 0.080 |

Biological Example 3

In Vivo Assay

GPR120 DIO Mice OGTT Screening 18-22 week old, C57Bl6 mice on a high fat diet (60% HFD) for 12-16 weeks (ave. body weight ~37-41 g) were fasted for 6 hr, with removal of food occurring at 7 am on the morning of the study. The animals were sorted into treatment groups the day before the study by body weight. Animals outside the bounds of ~30-50 g were left out of the study. The animals had been handled and shammed a total of 5-8 days (1-3 days immediately prior to the study). Glucose (in 1 ml syringes) was drawn up the morning of the study. Test compounds were kept spinning and were only drawn into 1 ml syringes prior to study commencement. Animals were bled via tail snip to determine basal glucose levels prior to dosing of treatments. An Ascensia BREEZE Blood Glucose Monitoring System by Bayer was used for determining glucose levels.

Animals were moved into the testing room at ~9-11 am, to yield them time to acclimate. The bleeds and dosing started at approximately 1 pm in 30-second intervals per animal. All groups were dosed 30 minutes prior to glucose administration at a dose volume of 10 ml/kg (the dose volume was calculated separately for each individual animal). Test compounds were administered at two or more of the following dosages: 0.1 mg/kg, 0.3 mg/kg, 1 mg/kg, 3 mg/kg, 10 mg/kg and 30 mg/kg.

Thirty minutes after the first dose (with test compound) animals were bled again for a second baseline, or T=0, and immediately dosed with glucose (20% solution; TEKNOVA, 250 ml sterile bottle w/ catalogue number G0525) via a PO injection. The exact dose volume for glucose was also calculated separately for each individual animal.

Blood glucose was measured at 15, 30, 45, 60, and 90 minutes post-glucose administration via the snipped tail. If an animal reached a value of "HI", the upper limit of the glucometer (600 mg/dl) was substituted as the blood glucose value and the study was analyzed as normal with no exclusions. If 50% or more of any treatment group reaches a "HI" value at least once, the study was considered invalid and repeated. Glucose values were typed into an EXCEL spreadsheet where they were used to calculate glucose AUC and delta AUC post-compound and post-glucose. The glucose excursion curves and the different versions of the AUC's were graphed in GraphPad Prism 5.

Statistical Methods:

Note: All statistics completed in this study were completed using the statistical software package GraphPad Prism 5. Standard procedures for analyzing data sets from screening GPR120 compounds in DIO mouse OGTT's were as listed here below. In addition to the statistics that were run using GraphPad Prism 5, Microsoft Excel was used to calculate the percent changes in AUC from vehicle groups as detailed below.

Change from −30 to 0 BSLN Glucose, Raw Glucose AUC −30 to 90 min, Delta Glucose AUC −30 to 90 min, Raw Glucose AUC 0 to 90 min, Delta Glucose AUC 0 to 90 min were analyzed using Column Statistics Analysis, with mean values used to calculate % change from the vehicle mean group, as well as mean, SEM and/or % change from vehicle, where appropriate; and using One-Way ANOVA w/ a Tukey Post-Test (Comparing All Pairs of Columns) with each treatment group examined to see if it was statistically significant compared to vehicle (*=P<0.05, =P<0.01, *=P<0.001).

Representative compounds of the present invention were tested according to the procedure as described in Biological Example 3, with results as listed in Table 3-4, below.

TABLE 3

| GPR120 DIO OGTT Results | | |
|---|---|---|
| | DIO Lowering Glucose AUC | |
| ID No. | 10 mg/kg | 3 mg/kg |
| 34 | −50% | −27% |
| 39 | −68% | −59% |
| 70 | −82% | −79% |

The DIO dose response was measured for Compound #70, with results as listed in Table 4, below:

TABLE 4

| DIO Dose Response, Compound #70 | |
|---|---|
| Dose | Lowering Glucose AUC |
| 3.0 mg/kg | −73% |
| 1.0 mg/kg | −54% |
| 0.3 mg/kg | −8% |
| 0.1 mg/kg | 9% |

Biological Example 4

In Vivo Assays

A: GPR120 C57bl6 Mouse IPGTT

Male, C57bl/6J Mice were ordered in at 8 weeks of age from Jackson Labs. Individual mice weighed anywhere in the range of 25-30 grams on study day. The mice were fasted, with removal of food occurring at 7 am on the morning of the study. Animals were moved into the room at 10:00 am, to give them time to acclimate. Glucose (insulin syringes) was drawn up either the night before or the morning of the study. Glucose was dosed (IP) at 1.5 g/kg at 7.5 ml/kg (20% glucose straight TEKNOVA, 250 ml sterile bottle w/ catalogue number G0525). Test compounds were kept spinning and were only drawn into the syringes prior to study commencement. Animals were bled via tail snip to determine basal glucose levels prior to dosing of treatments. An Ascensia BREEZE Blood Glucose Monitoring System by Bayer (using unique 10-test disks) was used for determining glucose levels. The bleeds started at approximately 12:45 pm and dosing started, at 1-minute intervals, immediately after. All groups were dosed 30 minutes prior to glucose administration at a dose volume of 10 ml/kg (the dose volume was calculated separately for each individual animal). Thirty minutes after the first dose animals were bled again for a second baseline, or T=0, and immediately dosed with glucose via an i.p. injection. The exact dose volume for glucose was also calculated separately for each individual animal. Glucose measurements were taken at −30 min prior to compound dose, at t=0 (immediately prior to glucose dose), and at 15, 30, 45, 60, 90 min post glucose dose.

Glucose values were entered into an Excel sheet and graphed in GraphPad Prism. The following were calculated from Prism: Change from −30 to 0 BSLN Glucose, Raw Glucose AUC −30 to 90 min, Delta Glucose AUC −30 to 90 min, Raw Glucose AUC 0 to 90 min, Delta Glucose AUC 0 to 90 min.

B: C57bl6 Mouse OGTT:

The assay design is the same as that described above for the C57bl6 mouse IPGTT. The difference is that glucose was dosed PO at 3 g/kg, 7.5 ml/kg of 40% glucose.

Representative compounds of the present invention were tested according to the procedures as described in Biological Example 4, above with results as listed in Table 5 below.

TABLE BIO-5

| GPR120 C57bl6 Mouse IPGTT Results | | |
|---|---|---|
| ID No. | 10.0 mg/kg | 30.0 mg/kg |
| 1 |  | not different from vehicle |
| 27 | −16 |  |
| 29 | −14 |  |
| 29 | −15 |  |
| 30 | −53 |  |
| 31 | −43 |  |
| 33 | −26 |  |
| 37 | −30 |  |

The C57bl6 Mouse IPGTT dose response was measured for representative compounds of the present invention, with results as listed in Table 6, below.

TABLE 6

| C57bl6 Mouse IPGTT dose response | | |
|---|---|---|
| Dose | Compound #30 | Compound #31 |
| 10 mg/kg | −48% | −44% |
| 3 mg/kg | −14% | −39% |
| 1 mg/kg | 1% | 2% |

Formulation Example 1 (Prophetic Example)

Solid, Oral Dosage Form

As a specific embodiment of an oral composition, 100 mg of the Compound #70, prepared as in Example 1, above is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the according to claims and their equivalents.

We claim:

1. A compound of formula (I)

wherein $R^1$ is selected from the group consisting of phenyl and pyridinyl; wherein the phenyl or pyridinyl is optionally substituted with one to three substituents independently selected from the group consisting of halogen, cyano, carboxy, —C(O)O—($C_{1-4}$alkyl), —C(O)—($C_{1-4}$alkyl), $C_{1-4}$alkyl, fluoro substituted $C_{1-4}$alkyl, $C_{1-4}$alkoxy and fluoro substituted $C_{1-4}$alkoxy;

$R^2$ is selected from the group consisting of hydrogen, halogen, cyano, $C_{1-4}$alkyl and fluoro substituted $C_{1-4}$alkyl;

a is in integer from 0 to 3;

each $R^3$ is independently selected from the group consisting of halogen, $C_{1-4}$alkyl, fluoro substituted $C_{1-4}$alkyl, and cyano;

provided that when a is 2 or 3, then only one $R^3$ can be cyano;

$R^4$ is selected from the group consisting of hydrogen and methyl;

$R^5$ is selected from the group consisting of —$CH_2OH$ and —C(O)OH;

or a pharmaceutically acceptable salt thereof.

2. A compound as in claim 1, wherein $R^1$ is selected from the group consisting of phenyl and pyridinyl; wherein the phenyl is optionally substituted with one to two substituents independently selected from the group consisting of halogen, $C_{1-4}$alkyl, fluoro substituted $C_{1-4}$alkyl, $C_{1-4}$alkoxy and fluoro substituted $C_{1-4}$alkoxy; and wherein the pyridinyl is optionally substituted with one substituent selected from the group consisting of $C_{1-4}$alkyl and $C_{1-4}$alkoxy;

$R^2$ is selected from the group consisting of hydrogen, halogen, cyano, $C_{1-4}$alkyl and fluoro substituted $C_{1-4}$alkyl;

a is 2;

each $R^3$ is independently selected from the group consisting of halogen and $C_{1-2}$alkyl;

$R^4$ is selected from the group consisting of hydrogen and methyl;

$R^5$ is selected from the group consisting of —$CH_2OH$ and —C(O)OH;

or a pharmaceutically acceptable salt thereof.

3. A compound as in claim 2, wherein $R^1$ is selected from the group consisting of phenyl and pyridin-3-yl; wherein the phenyl is optionally substituted with one to two substituents independently selected from the group consisting of halogen, $C_{1-2}$alkyl, fluoro substituted $C_{1-2}$alkyl, $C_{1-2}$alkoxy and fluoro substituted $C_{1-2}$alkoxy;

$R^2$ is selected from the group consisting of hydrogen, halogen, cyano, $C_{1-2}$alkyl and fluoro substituted $C_{1-2}$alkyl;

a is 2;

each $R^3$ is independently selected from the group consisting of halogen and $C_{1-2}$alkyl; and wherein the $R^3$ groups are the same and are bound at the 2- and 3- or at the 3- and 5-positions;

R⁴ is selected from the group consisting of hydrogen and methyl;
R⁵ is selected from the group consisting of —CH₂OH and —C(O)OH;
or a pharmaceutically acceptable salt thereof.

4. A compound as in claim 1, wherein
R¹ is selected from the group consisting of phenyl, 4-chlorophenyl, 4-fluorophenyl, 4-bromophenyl, 4-methylphenyl, 4-ethylphenyl, 4-methoxyphenyl, 3-fluoro-4-chloro-phenyl, 3-fluoro-4-methyl-phenyl, 6-methyl-pyridin-3-yl, 6-ethyl-pyridin-3-yl and 6-methoxy-pyridin-3-yl;
R² is selected from the group consisting of hydrogen, chloro, bromo, cyano, trifluoromethyl and pentafluoroethyl;
a is 2;
R³ is selected from the group consisting of 2,3-difluoro, 2,3-dimethyl and 3,5-difluoro;
R⁴ is selected from the group consisting of hydrogen and methyl;
R⁵ is selected from the group consisting of —CH₂OH and —C(O)OH;
or a pharmaceutically acceptable salt thereof.

5. A compound as in claim 4, wherein
R¹ is selected from the group consisting of phenyl, 4-chlorophenyl, 4-bromophenyl, 4-methylphenyl, 4-ethylphenyl, 4-methoxyphenyl, 3-fluoro-4-chloro-phenyl, 3-fluoro-4-methyl-phenyl, 6-methyl-pyridin-3-yl, 6-ethyl-pyridin-3-yl and 6-methoxy-pyridin-3-yl;
R² is selected from the group consisting of hydrogen, chloro, bromo and trifluoromethyl;
a is 2;
R³ is selected from the group consisting of 2,3-difluoro, 2,3-dimethyl and 3,5-difluoro;
R⁴ is selected from the group consisting of hydrogen and methyl;
R⁵ is selected from the group consisting of —CH₂OH and —C(O)OH;
or a pharmaceutically acceptable salt thereof.

6. A compound as in claim 4, wherein
R¹ is selected from the group consisting of phenyl, 4-chlorophenyl, 4-bromophenyl, 4-methylphenyl, 4-ethylphenyl, 4-methoxyphenyl, 6-methyl-pyridin-3-yl, 6-ethyl-pyridin-3-yl and 6-methoxy-pyridin-3-yl;
R² is selected from the group consisting of hydrogen, chloro, bromo and trifluoromethyl;
a is 2;
R³ is selected from the group consisting of 2,3-difluoro, 2,3-dimethyl and 3,5-difluoro;
R⁴ is selected from the group consisting of hydrogen and methyl;
R⁵ is selected from the group consisting of —CH₂OH and —C(O)OH;
or a pharmaceutically acceptable salt thereof.

7. A compound as in claim 4, wherein
R¹ is selected from the group consisting of phenyl, 4-chlorophenyl, 4-methylphenyl, 4-ethylphenyl, 4-methoxyphenyl, 6-methyl-pyridin-3-yl, 6-ethyl-pyridin-3-yl and 6-methoxy-pyridin-3-yl;
R² is trifluoromethyl;
a is 2;
R³ is selected from the group consisting of 2,3-difluoro, 2,3-dimethyl and 3,5-difluoro;
R⁴ is hydrogen;
R⁵ is selected from the group consisting of —CH₂OH and —C(O)OH;
or a pharmaceutically acceptable salt thereof.

8. A compound as in claim 4, wherein
R¹ is selected from the group consisting of 4-chlorophenyl, 4-methylphenyl, 4-ethylphenyl, 6-methyl-pyridin-3-yl and 6-ethyl-pyridin-3-yl;
R² is trifluoromethyl;
a is 2;
R³ is selected from the group consisting of 2,3-difluoro and 3,5-difluoro;
R⁴ is hydrogen;
R⁵ is selected from the group consisting of —CH₂OH and —C(O)OH;
or a pharmaceutically acceptable salt thereof.

9. A compound as in claim 4, selected from the group consisting of
3-(4-{[1-(4-Chlorophenyl)-3-(trifluoromethyl)-1H-pyrrol-2-yl]methoxy}-2,3-dimethylphenyl)propanoic acid;
3-(4-{[1-(4-Ethylphenyl)-3-(trifluoromethyl)-1H-pyrrol-2-yl]methoxy}-2,3-difluorophenyl)propanoic acid;
3-(3,5-Difluoro-4-{[1-(4-methylphenyl)-3-(trifluoromethyl)-1H-pyrrol-2-yl]methoxy}phenyl)propanoic acid;
3-(2,3-Dimethyl-4-{[1-(4-methyl phenyl)-3-(trifluoromethyl)-1H-pyrrol-2-yl]methoxy}phenyl)propanoic acid;
3-(4-{[1-(4-Chlorophenyl)-3-(trifluoromethyl)-1H-pyrrol-2-yl]methoxy}-3,5-difluorophenyl)propan-1-ol;
3-(2,3-Difluoro-4-{[1-(6-methoxypyridin-3-yl)-3-(trifluoromethyl)-1H-pyrrol-2-yl]methoxy}phenyl)propanoic acid;
3-(4-{[1-(4-Chlorophenyl)-3-(trifluoromethyl)-1H-pyrrol-2-yl]methoxy}-3,5-difluorophenyl)propanoic acid;
and pharmaceutically acceptable salts thereof.

10. A compound as in claim 9, selected from the group consisting of
3-(4-{[1-(4-Ethylphenyl)-3-(trifluoromethyl)-1H-pyrrol-2-yl]methoxy}-2,3-difluorophenyl)propanoic acid;
3-(3,5-Difluoro-4-{[1-(4-methylphenyl)-3-(trifluoromethyl)-1H-pyrrol-2-yl]methoxy}phenyl)propanoic acid;
3-(4-{[1-(4-Chlorophenyl)-3-(trifluoromethyl)-1H-pyrrol-2-yl]methoxy}-3,5-difluorophenyl)propanoic acid;
and pharmaceutically acceptable salts thereof.

11. A pharmaceutical composition comprising a pharmaceutically acceptable carrier and a compound of claim 1.

12. A pharmaceutical composition made by mixing a compound of claim 1 and a pharmaceutically acceptable carrier.

13. A process for making a pharmaceutical composition comprising mixing a compound of claim 1 and a pharmaceutically acceptable carrier.

14. A method of treating a disorder modulated by the GPR120 receptor, comprising administering to a subject in need thereof a therapeutically effective amount of the compound of claim 1.

15. The method of claim 14, wherein the disorder modulated by the GPR120 receptor is selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

16. A method of treating a disorder selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders comprising administering to a subject in need thereof a therapeutically effective amount of the composition of claim 11.

17. A method of treating a condition selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders comprising administering to a subject in need thereof, a therapeutically effective amount of the compound of claim 1.

18. A compound as in claim 1 for use as a medicament.

19. A compound as in claim 1 for use in the treatment of a disorder modulated by the GPR120 receptor.

20. A compound as in claim 1, for use in the treatment of a disorder modulated by the GPR120 receptor, selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

21. A composition comprising a compound as in claim 1, for use in the treatment of a disorder modulated by the GPR120 receptor.

22. A composition comprising a compound as in claim 1, for use in the treatment of a disorder modulated by the GPR120 receptor selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders.

\* \* \* \* \*